US012011220B2

(12) United States Patent
Emmons et al.

(10) Patent No.: US 12,011,220 B2
(45) Date of Patent: *Jun. 18, 2024

(54) MICROWAVE TREATMENT DEVICES AND METHODS

(71) Applicant: MicroCube, LLC, Fremont, CA (US)

(72) Inventors: Clarence Emmons, Capitola, CA (US); Chun Yiu Chu, Oakland, CA (US); Amrish J. Walke, Milpitas, CA (US); Dinesh I. Mody, San Jose, CA (US); Ketan Shroff, Pleasanton, CA (US)

(73) Assignee: MicroCube, LLC, Fremont, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/652,718

(22) Filed: Feb. 28, 2022

(65) Prior Publication Data

US 2022/0249163 A1 Aug. 11, 2022

Related U.S. Application Data

(63) Continuation of application No. 16/038,921, filed on Jul. 18, 2018, now Pat. No. 11,291,503, which is a (Continued)

(51) Int. Cl.
*A61B 18/18* (2006.01)
*A61B 18/00* (2006.01)
(Continued)

(52) U.S. Cl.
CPC .......... *A61B 18/1815* (2013.01); *A61N 7/022* (2013.01); *A61B 2018/00005* (2013.01); (Continued)

(58) Field of Classification Search
CPC ................ A61B 18/18; A61B 18/1815; A61B 2018/00005; A61B 2018/0023; (Continued)

(56) References Cited

U.S. PATENT DOCUMENTS 4,583,556 A 4/1986 Hines et al.
4,658,836 A 4/1987 Turner
(Continued)

FOREIGN PATENT DOCUMENTS

EP 1145686 10/2001
EP 1298542 4/2003
(Continued)

*Primary Examiner* — Ronald Hupczey, Jr.
(74) *Attorney, Agent, or Firm* — Levine Bagade Han LLP

(57) ABSTRACT

The present invention discloses medical systems and methods adapted for the delivery of various medical components such as microwave antennas within or on a body for performing one or more medical procedures. Several embodiments herein disclose medical systems comprising a combination of one or more medical components and one or more elongate steerable or non-steerable arms that are adapted to mechanically manipulate the one or more medical components. Several embodiments of microwave antennas are disclosed that comprise an additional diagnostic or therapeutic modality located on or in the vicinity of the microwave antennas.

19 Claims, 43 Drawing Sheets

Related U.S. Application Data continuation of application No. 14/462,434, filed on Aug. 18, 2014, now abandoned, which is a continuation-in-part of application No. 12/603,134, filed on Oct. 21, 2009, now Pat. No. 8,808,281.

(60) Provisional application No. 61/222,409, filed on Jul. 1, 2009, provisional application No. 61/180,133, filed on May 21, 2009, provisional application No. 61/162,241, filed on Mar. 20, 2009, provisional application No. 61/107,252, filed on Oct. 21, 2008.

(51) Int. Cl.
*A61B 18/02* (2006.01)
*A61B 18/20* (2006.01)
*A61N 7/02* (2006.01)

(52) U.S. Cl.
CPC .............. *A61B 2018/00023* (2013.01); *A61B 2018/00029* (2013.01); *A61B 2018/00184* (2013.01); *A61B 2018/00351* (2013.01); *A61B 2018/00404* (2013.01); *A61B 2018/00422* (2013.01); *A61B 2018/0044* (2013.01); *A61B 2018/00452* (2013.01); *A61B 2018/00488* (2013.01); *A61B 2018/00494* (2013.01); *A61B 2018/005* (2013.01); *A61B 2018/00511* (2013.01); *A61B 2018/00517* (2013.01); *A61B 2018/00523* (2013.01); *A61B 2018/00529* (2013.01); *A61B 2018/00541* (2013.01); *A61B 2018/00547* (2013.01); *A61B 2018/00559* (2013.01); *A61B 2018/00577* (2013.01); *A61B 2018/00642* (2013.01); *A61B 2018/00702* (2013.01); *A61B 2018/00726* (2013.01); *A61B 2018/00761* (2013.01); *A61B 2018/00785* (2013.01); *A61B 2018/00791* (2013.01); *A61B 2018/00827* (2013.01); *A61B 2018/00839* (2013.01); *A61B 2018/00863* (2013.01); *A61B 2018/00875* (2013.01); *A61B 2018/00892* (2013.01); *A61B 2018/00904* (2013.01); *A61B 2018/00982* (2013.01); *A61B 2018/00994* (2013.01); *A61B 2018/0212* (2013.01); *A61B 2018/1846* (2013.01); *A61B 2018/1853* (2013.01); *A61B 2018/1861* (2013.01); *A61B 2018/1869* (2013.01); *A61B 18/20* (2013.01)

(58) Field of Classification Search
CPC .. A61B 2018/0029; A61B 2018/00124; A61B 2018/00184; A61B 2018/00351; A61B 2018/00404; A61B 2018/0042; A61B 2018/0044; A61B 2018/00452; A61B 2018/00488; A61B 2018/00494; A61B 2018/005; A61B 2018/00511; A61B 2018/00517; A61B 2018/00523; A61B 2018/00529; A61B 2018/00541; A61B 2018/00547; A61B 2018/00549; A61B 2018/00577; A61B 2018/00642; A61B 2018/00702; A61B 2018/00726; A61B 2018/00761; A61B 2018/00785; A61B 2018/00791; A61B 2018/00827; A61B 2018/00839; A61B 2018/00863; A61B 2018/00875; A61B 2018/00892; A61B 2018/00904; A61B 2018/0212; A61B 2018/1846; A61B 2018/1853; A61B 2018/1861; A61B 2018/1869

See application file for complete search history.

(56) References Cited

U.S. PATENT DOCUMENTS

| | | | |
|---|---|---|---|
| 4,700,716 | A | 10/1987 | Kasevich et al. |
| 5,007,437 | A | 4/1991 | Sterzer |
| 5,057,106 | A | 10/1991 | Kasevich et al. |
| 5,129,396 | A | 7/1992 | Rosen et al. |
| 5,277,201 | A | 1/1994 | Stern |
| 5,449,380 | A | 9/1995 | Chin |
| 5,603,697 | A | 2/1997 | Grundy et al. |
| 5,741,249 | A | 4/1998 | Moss et al. |
| 5,769,880 | A | 6/1998 | Truckai et al. |
| 5,788,692 | A | 8/1998 | Campbell et al. |
| 5,861,021 | A | 1/1999 | Thome et al. |
| 5,902,251 | A | 5/1999 | vanHooydonk |
| 5,928,145 | A | 7/1999 | Ocali et al. |
| 5,957,969 | A | 9/1999 | Warner et al. |
| 6,210,367 | B1 | 4/2001 | Carr |
| 6,287,302 | B1 | 9/2001 | Berube |
| 6,306,132 | B1 | 10/2001 | Moorman et al. |
| 6,381,483 | B1 | 4/2002 | Hareyama et al. |
| 6,471,696 | B1 | 10/2002 | Berube et al. |
| 6,503,247 | B2 | 1/2003 | Swartz et al. |
| 6,635,055 | B1 | 10/2003 | Cronin |
| 6,663,625 | B1 * | 12/2003 | Ormsby ............ A61B 18/1815 606/41 |
| 6,813,520 | B2 | 11/2004 | Truckai et al. |
| 6,817,999 | B2 | 11/2004 | Berube et al. |
| 6,929,642 | B2 | 8/2005 | Xiao et al. |
| 7,197,363 | B2 | 3/2007 | Prakesh et al. |
| 7,226,446 | B1 | 6/2007 | Mody et al. |
| 7,864,160 | B2 | 1/2011 | Geaghan et al. |
| 8,808,281 | B2 * | 8/2014 | Emmons ................ A61B 18/18 606/33 |
| 8,968,287 | B2 | 3/2015 | Shroff et al. |
| 9,615,882 | B2 | 4/2017 | Shroff et al. |
| 9,980,774 | B2 | 5/2018 | Chu et al. |
| 9,993,293 | B2 | 6/2018 | Chu et al. |
| 10,299,859 | B2 | 5/2019 | Chu et al. |
| 10,470,819 | B2 | 11/2019 | Chu et al. |
| 10,869,720 | B2 | 12/2020 | Chu et al. |
| 11,147,619 | B2 | 10/2021 | Chu et al. |
| 11,219,484 | B2 | 1/2022 | Chu et al. |
| 11,291,503 | B2 * | 4/2022 | Emmons ................ A61B 18/14 |
| 11,684,418 | B2 | 6/2023 | Chu et al. |
| 2003/0057413 | A1 | 3/2003 | Kim et al. |
| 2003/0109868 | A1 | 6/2003 | Chin |
| 2003/0163128 | A1 | 8/2003 | Patil et al. |
| 2003/0195499 | A1 | 10/2003 | Prakash et al. |
| 2004/0002703 | A1 | 1/2004 | Xiao et al. |
| 2005/0240173 | A1 * | 10/2005 | Palti ........................ A61B 18/12 606/37 |
| 2006/0200119 | A1 | 9/2006 | Vaska et al. |
| 2006/0293652 | A1 | 12/2006 | van der Weide |
| 2007/0066972 | A1 * | 3/2007 | Ormsby ............ A61B 18/1492 606/41 |
| 2007/0139294 | A1 | 6/2007 | Dunn et al. |
| 2007/0179552 | A1 | 8/2007 | Dennis et al. |
| 2007/0203480 | A1 | 8/2007 | Mody et al. |
| 2007/0213583 | A1 | 9/2007 | Kim et al. |
| 2008/0082093 | A1 | 4/2008 | Prakash et al. |
| 2008/0167664 | A1 | 7/2008 | Payne et al. |
| 2009/0146439 | A1 | 6/2009 | Watts |
| 2010/0121319 | A1 | 5/2010 | Chu et al. |
| 2010/0125269 | A1 | 5/2010 | Emmons et al. |
| 2010/0137857 | A1 | 6/2010 | Shroff et al. |
| 2010/0137860 | A1 | 6/2010 | Demarais et al. |
| 2011/0004205 | A1 | 1/2011 | Chu et al. |
| 2011/0040300 | A1 | 2/2011 | Brannan |
| 2011/0257641 | A1 | 10/2011 | Hastings |
| 2012/0116486 | A1 | 5/2012 | Naga et al. |
| 2014/0290830 | A1 | 10/2014 | Brannan |
| 2014/0358140 | A1 | 12/2014 | Emmons et al. |
| 2015/0313670 | A1 | 11/2015 | Shroff et al. |
| 2018/0036080 | A1 | 2/2018 | Dickhans et al. |
| 2018/0303547 | A1 | 10/2018 | Chu et al. |
| 2018/0318005 | A1 | 11/2018 | Chu et al. |
| 2018/0325592 | A1 | 11/2018 | Emmons et al. |

(56) References Cited

U.S. PATENT DOCUMENTS

| | | |
|---|---|---|
| 2018/0344397 A1 | 12/2018 | Chu et al. |
| 2019/0380776 A1 | 12/2019 | Chu et al. |
| 2020/0121388 A1 | 4/2020 | Chu et al. |
| 2020/0405389 A1 | 12/2020 | Shroff et al. |
| 2021/0205014 A1 | 7/2021 | Chu et al. |
| 2022/0000553 A1 | 1/2022 | Chu et al. |
| 2024/0000505 A1 | 1/2024 | Chu et al. |

FOREIGN PATENT DOCUMENTS

| | | |
|---|---|---|
| EP | 1511315 | 3/2005 |
| JP | 2001-231790 | 8/2001 |
| JP | 2002-017745 | 1/2002 |
| JP | 2005-512668 | 5/2005 |
| JP | 2005-312807 | 11/2005 |
| JP | 2005-534352 | 11/2005 |
| JP | 2007-535369 | 12/2007 |
| KR | 10-2018-0095832 | 8/2018 |
| WO | WO 1997/006739 | 2/1997 |
| WO | WO 2002/011445 | 2/2002 |
| WO | WO 2003/053259 | 7/2003 |
| WO | WO 2003/088858 | 10/2003 |
| WO | WO 2006/004585 | 1/2006 |
| WO | WO 2008/071914 | 6/2008 |
| WO | WO 2009/146439 | 12/2009 |
| WO | WO 2010/048334 | 4/2010 |
| WO | WO 2010/048335 | 4/2010 |
| WO | WO 2010/053700 | 5/2010 |
| WO | WO 2012/003232 | 1/2012 |
| WO | WO 2013/149245 | 10/2013 |
| WO | WO 2020/264209 | 12/2020 |

\* cited by examiner

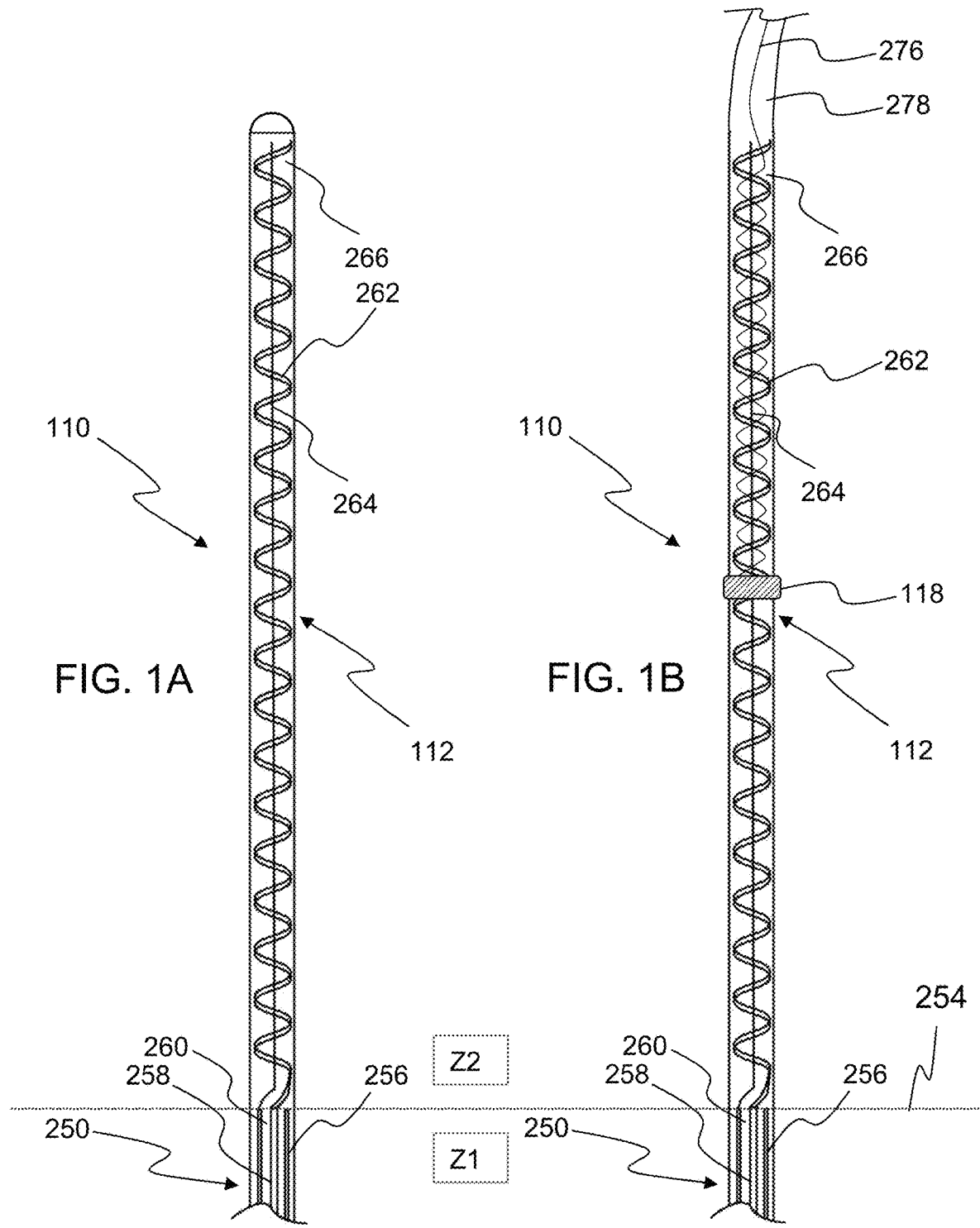

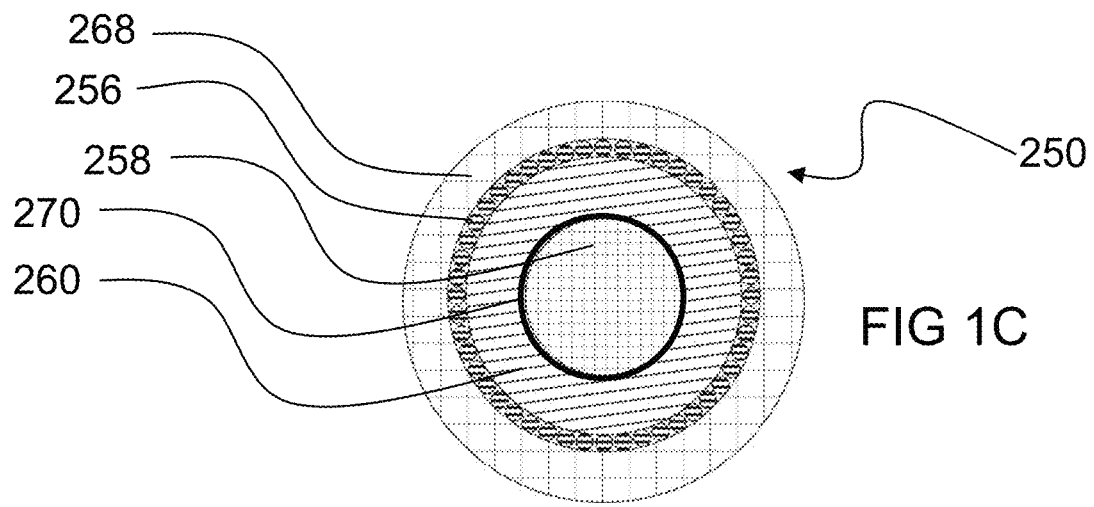
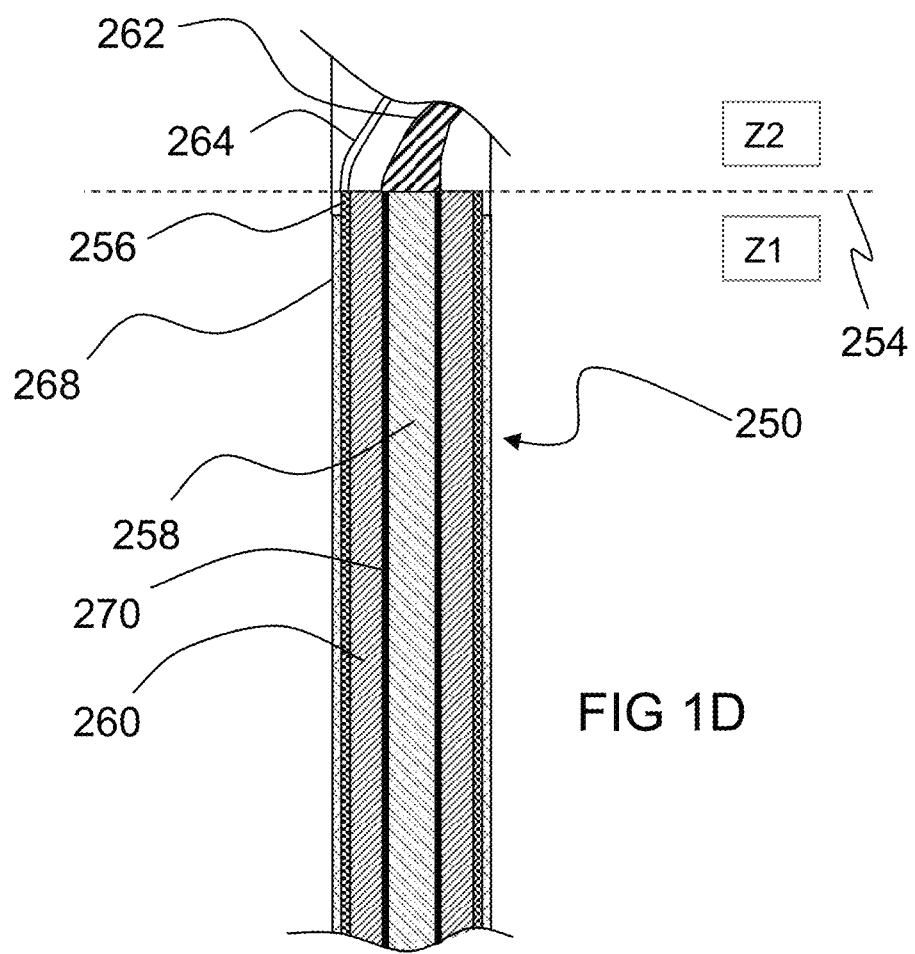

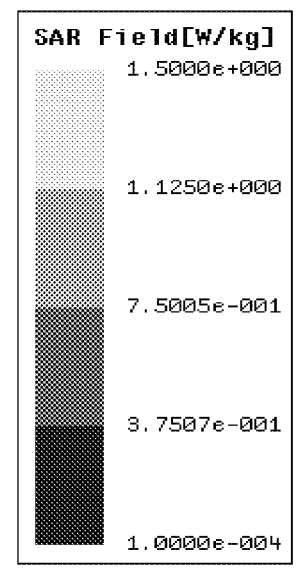
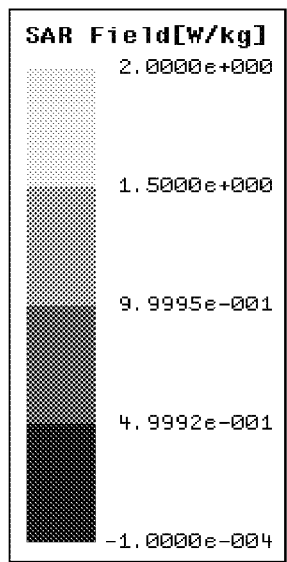
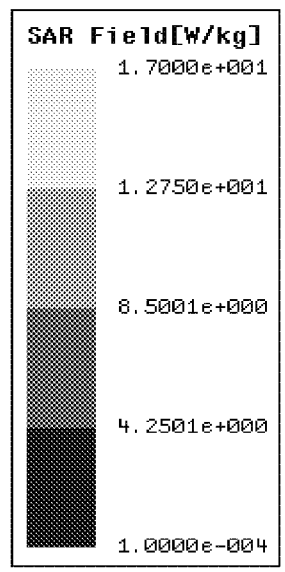
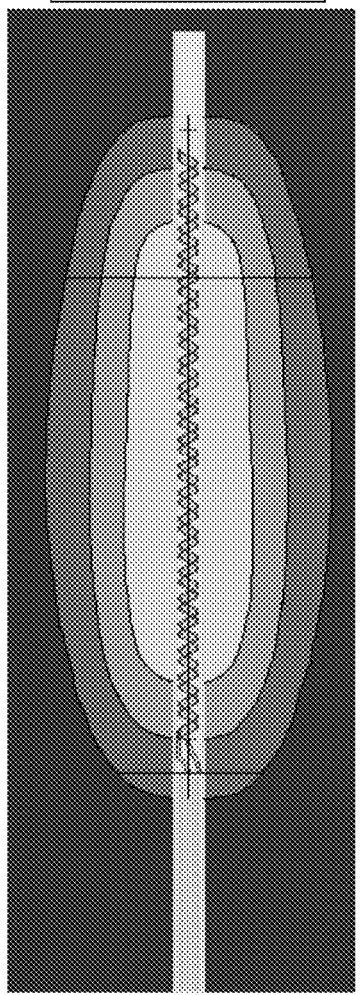
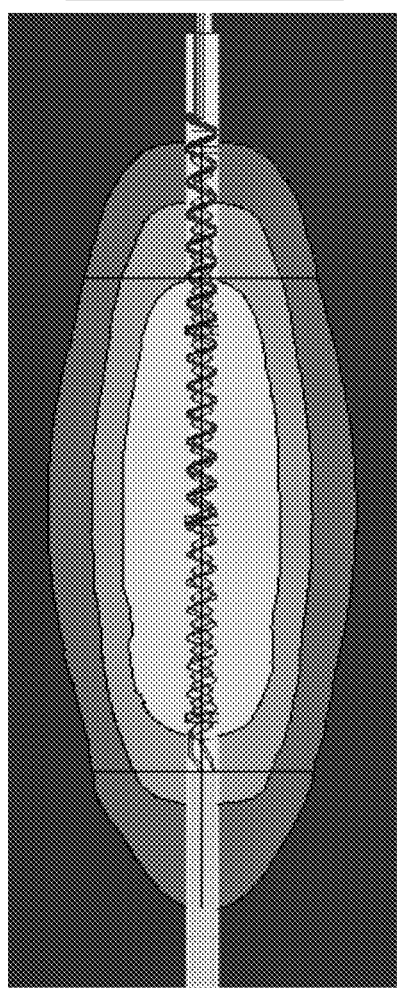
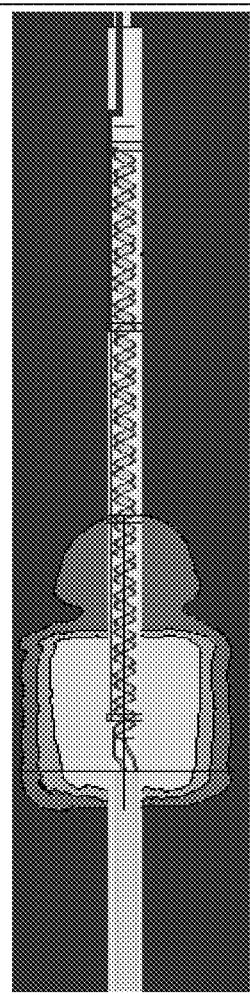
FIG 1P  FIG 1Q  FIG 1R

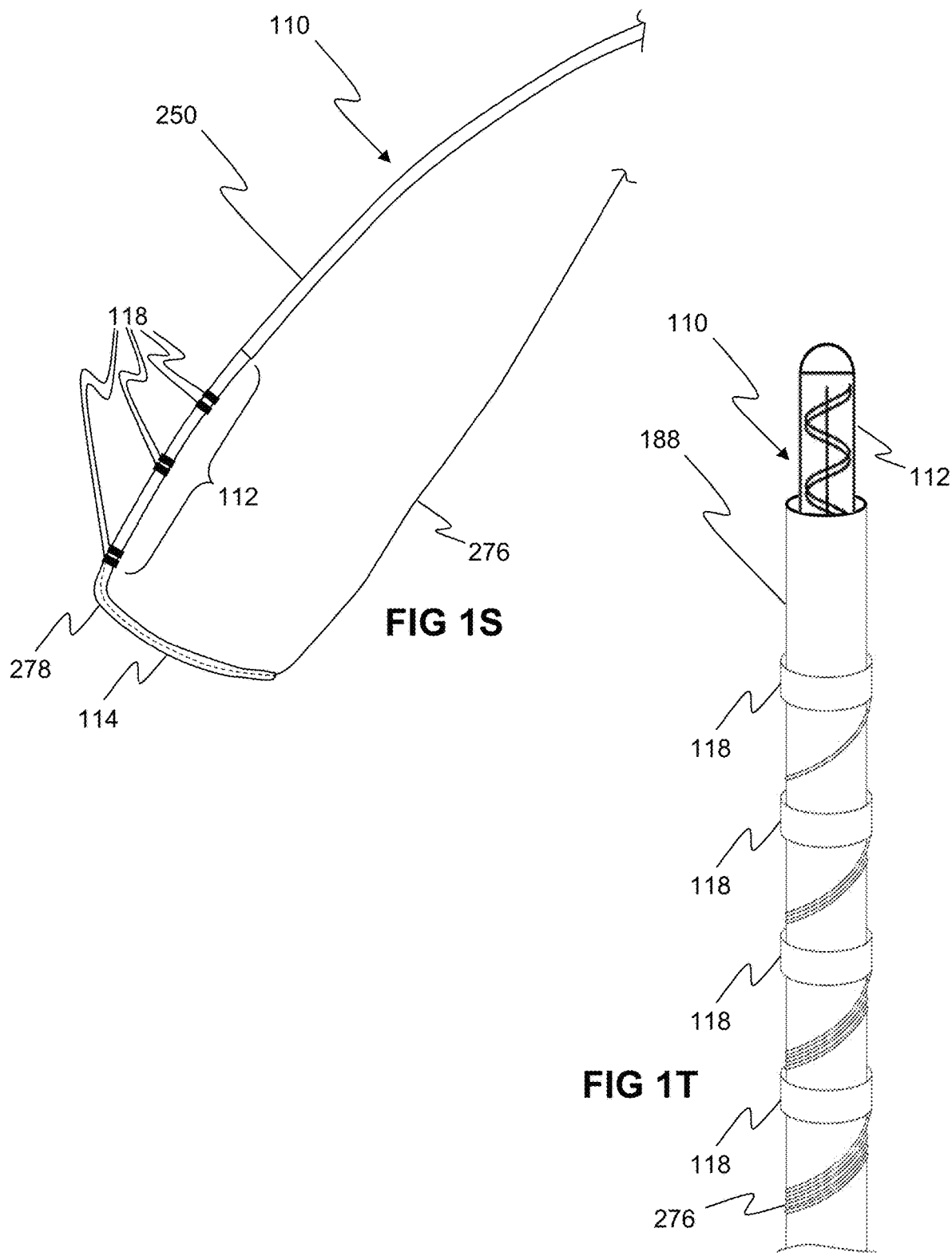

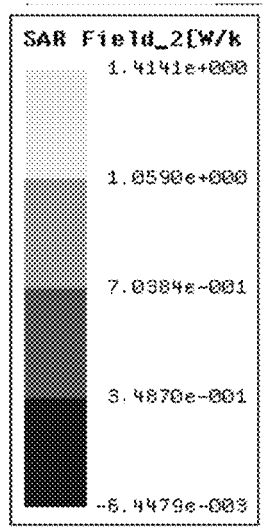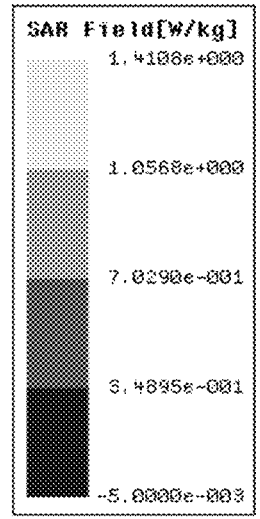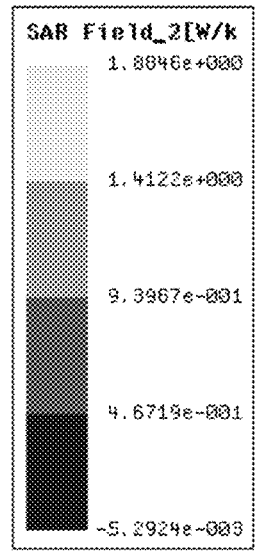
FIG 1U  FIG 1V  FIG 1W

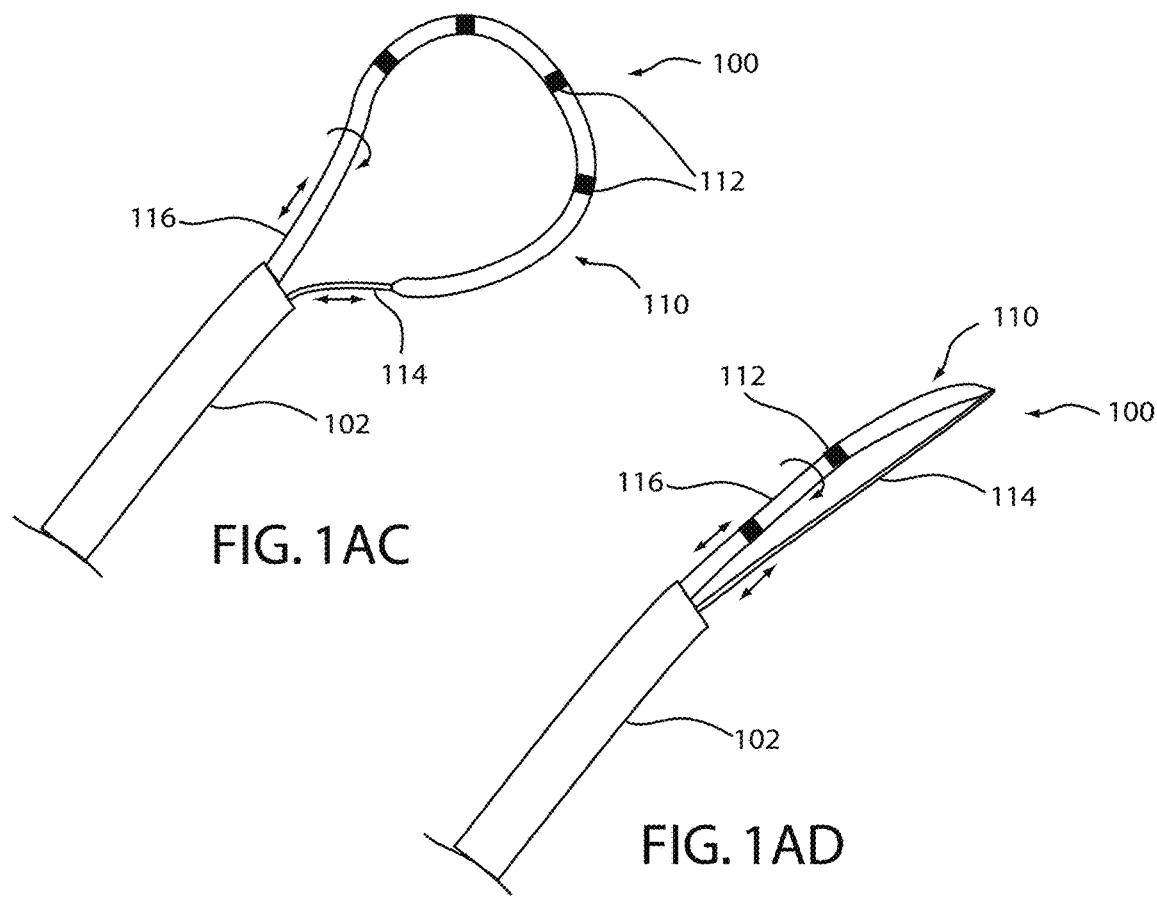
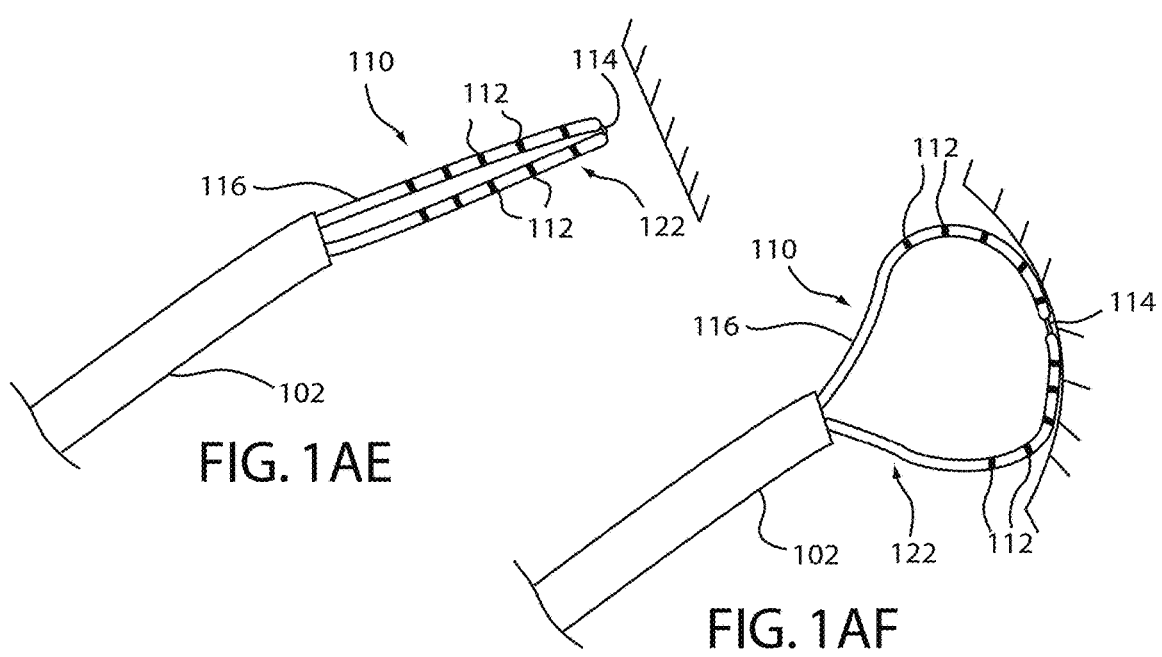

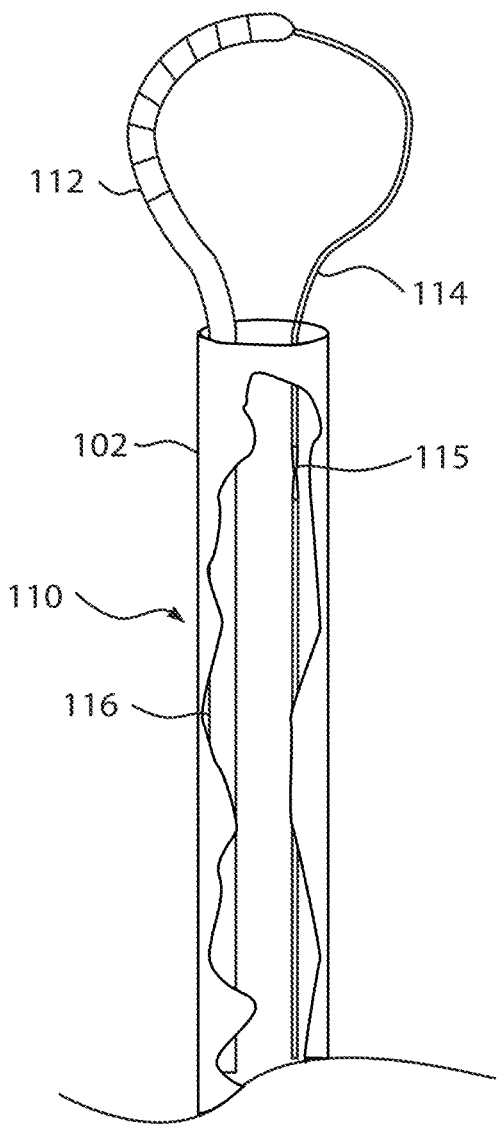
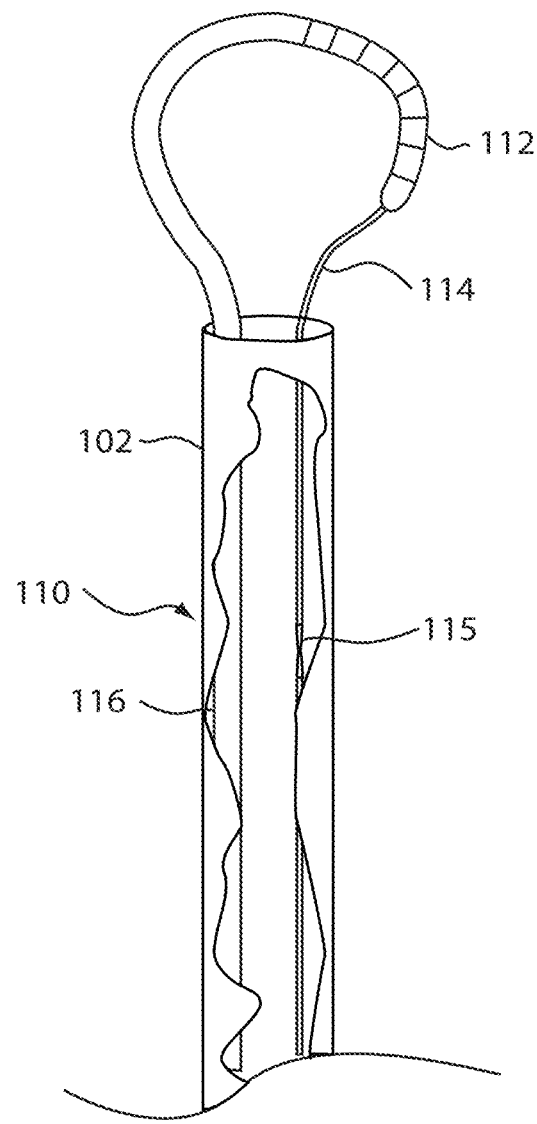
FIG. 1AJ    FIG. 1AK

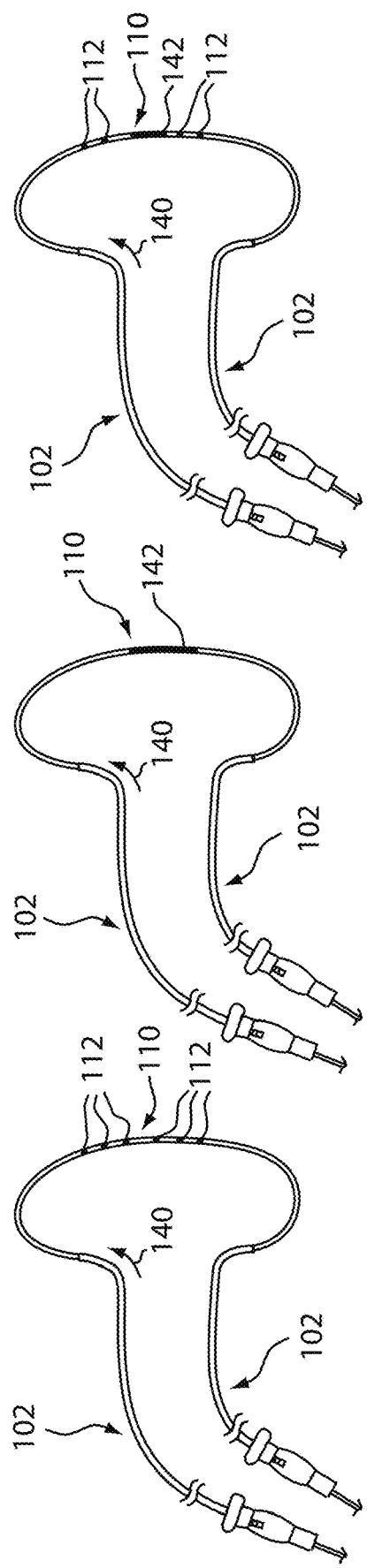
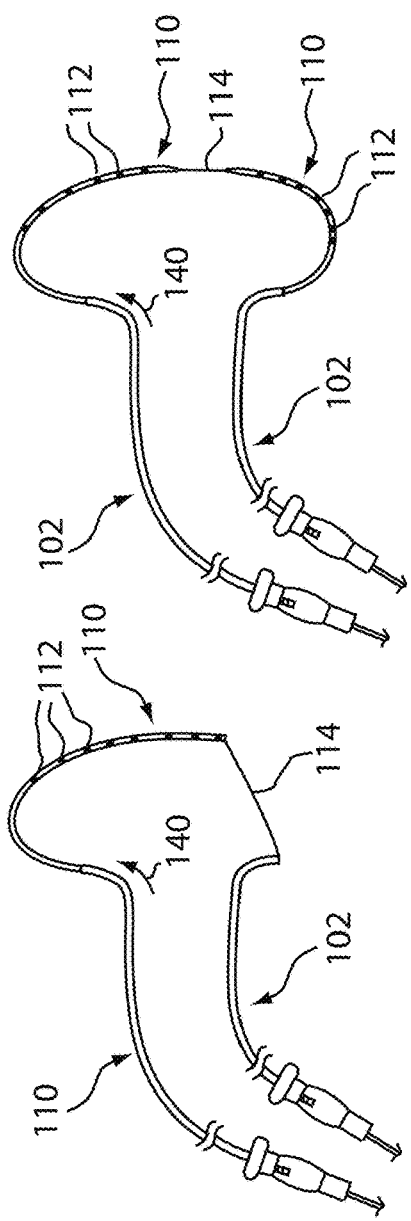

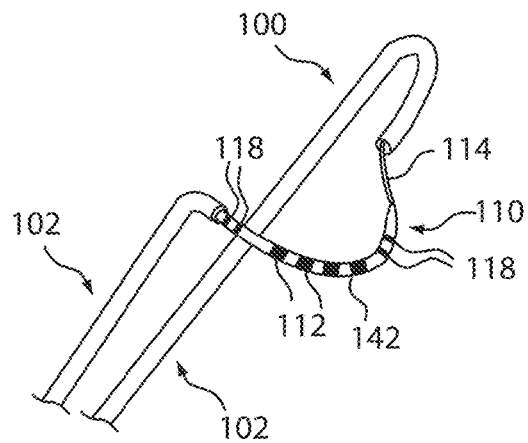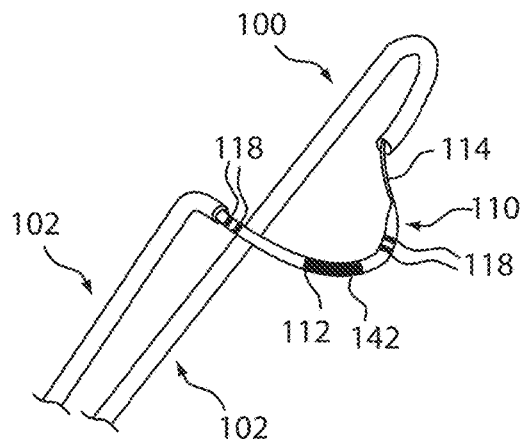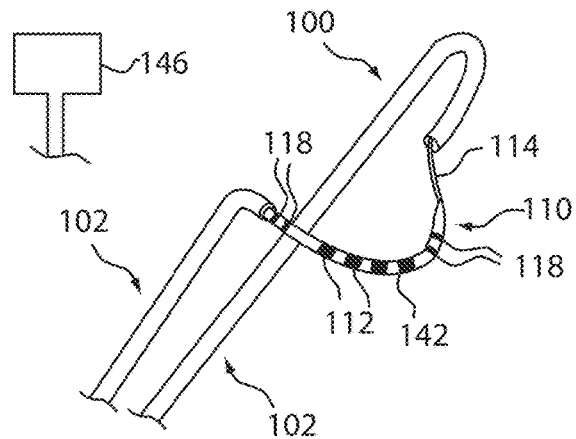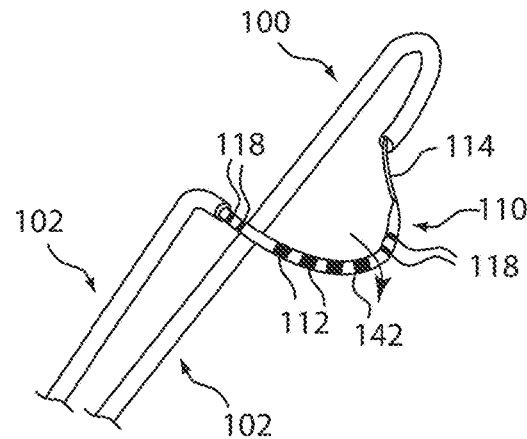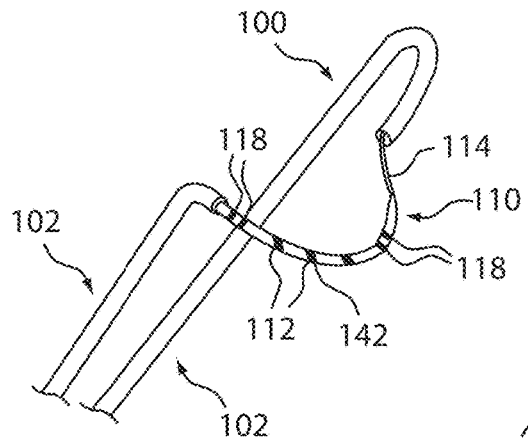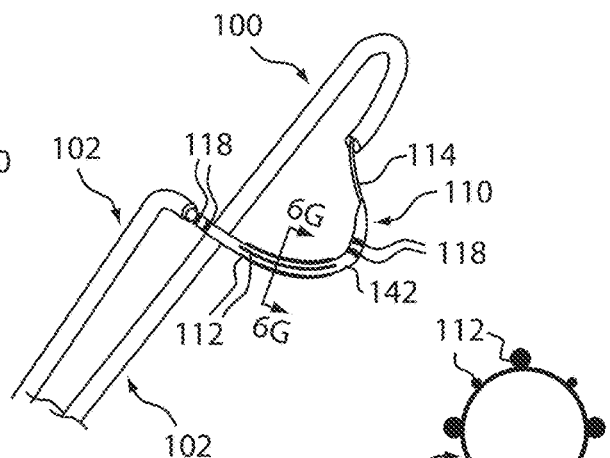

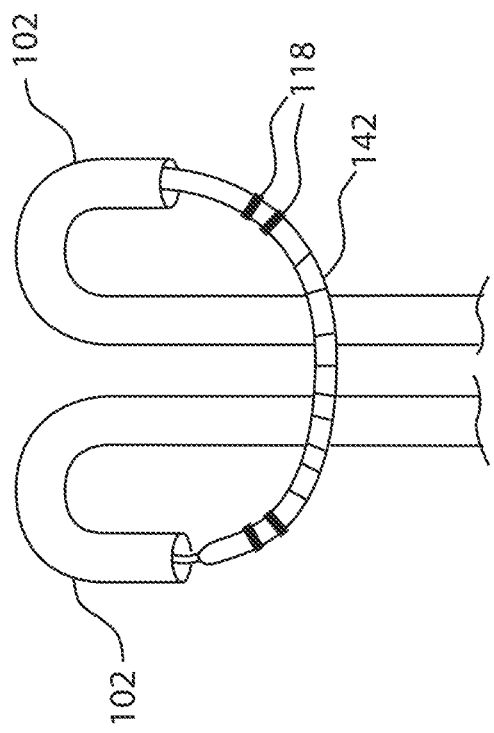
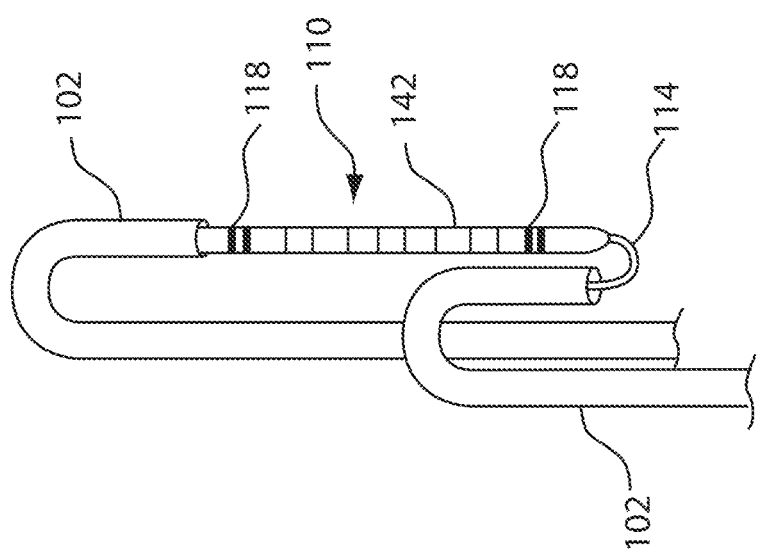

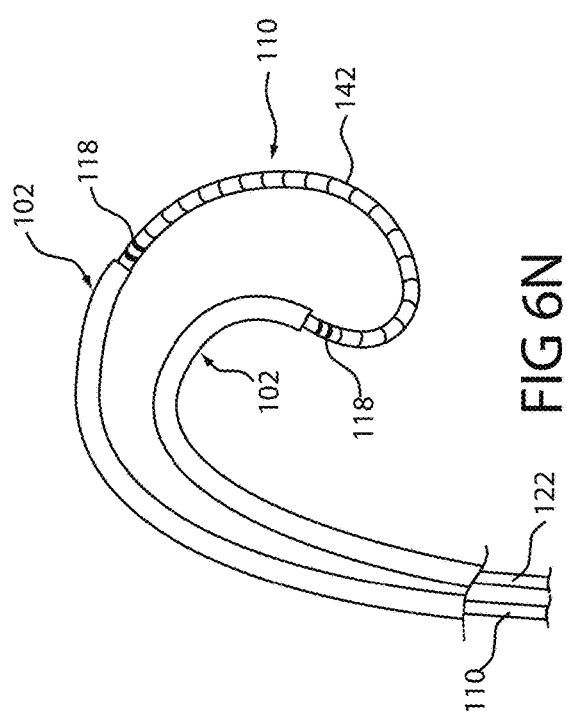
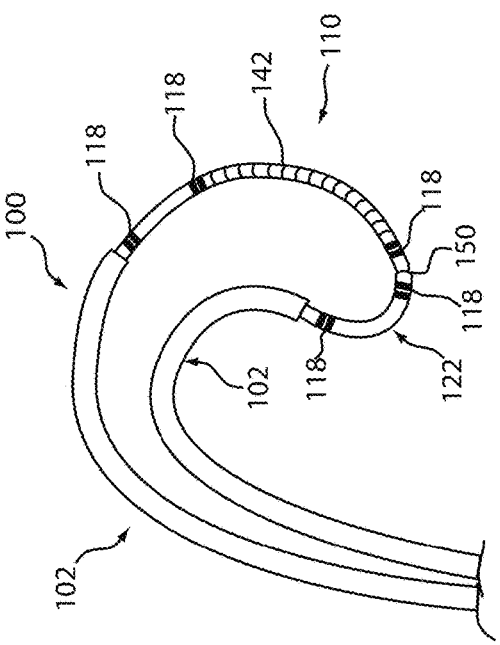
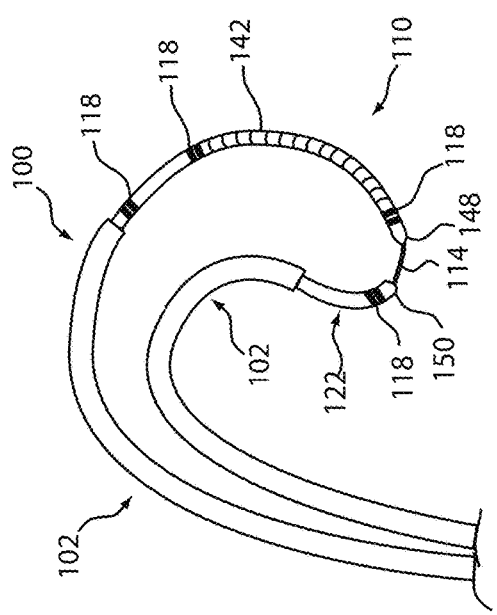

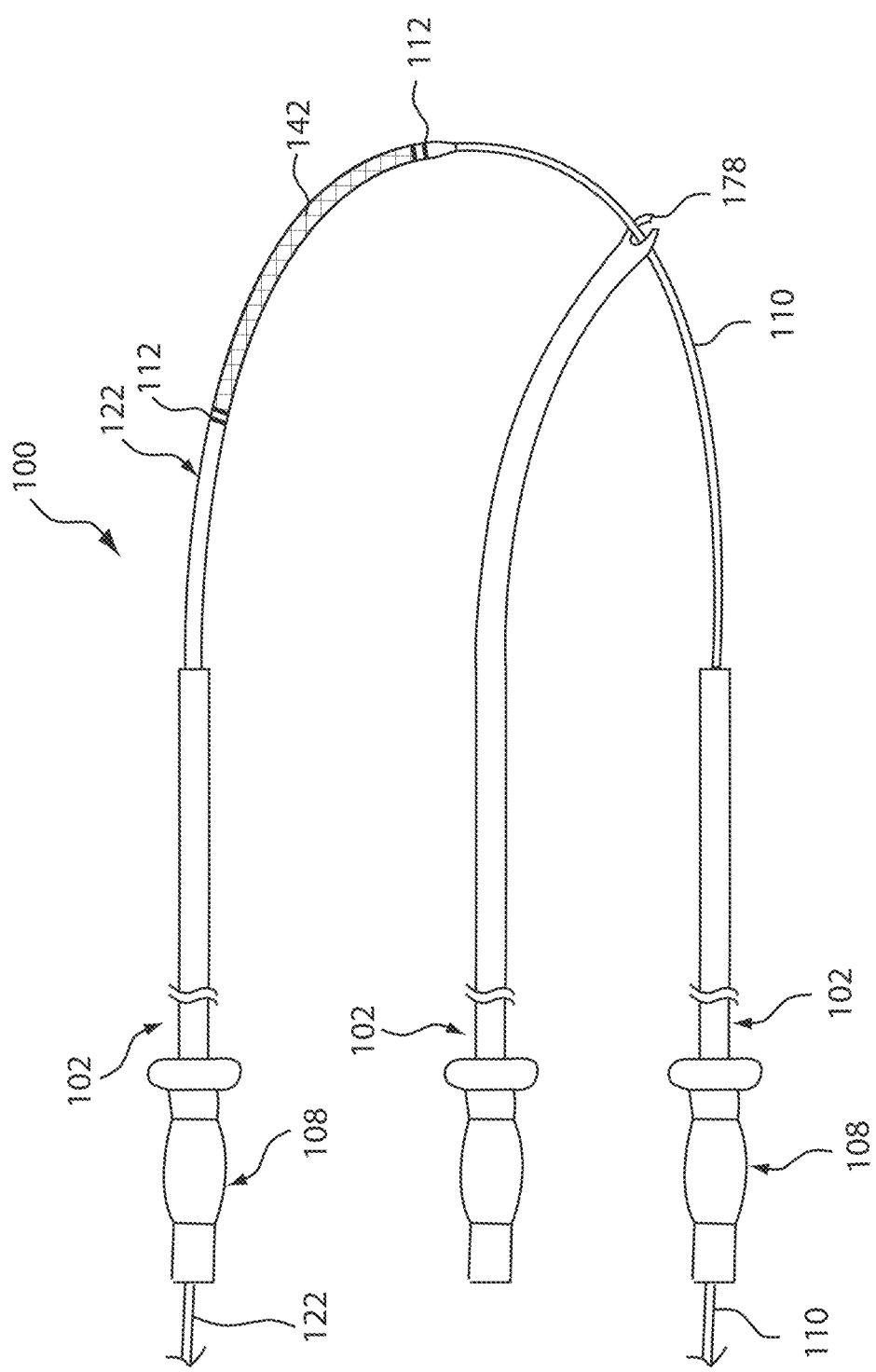

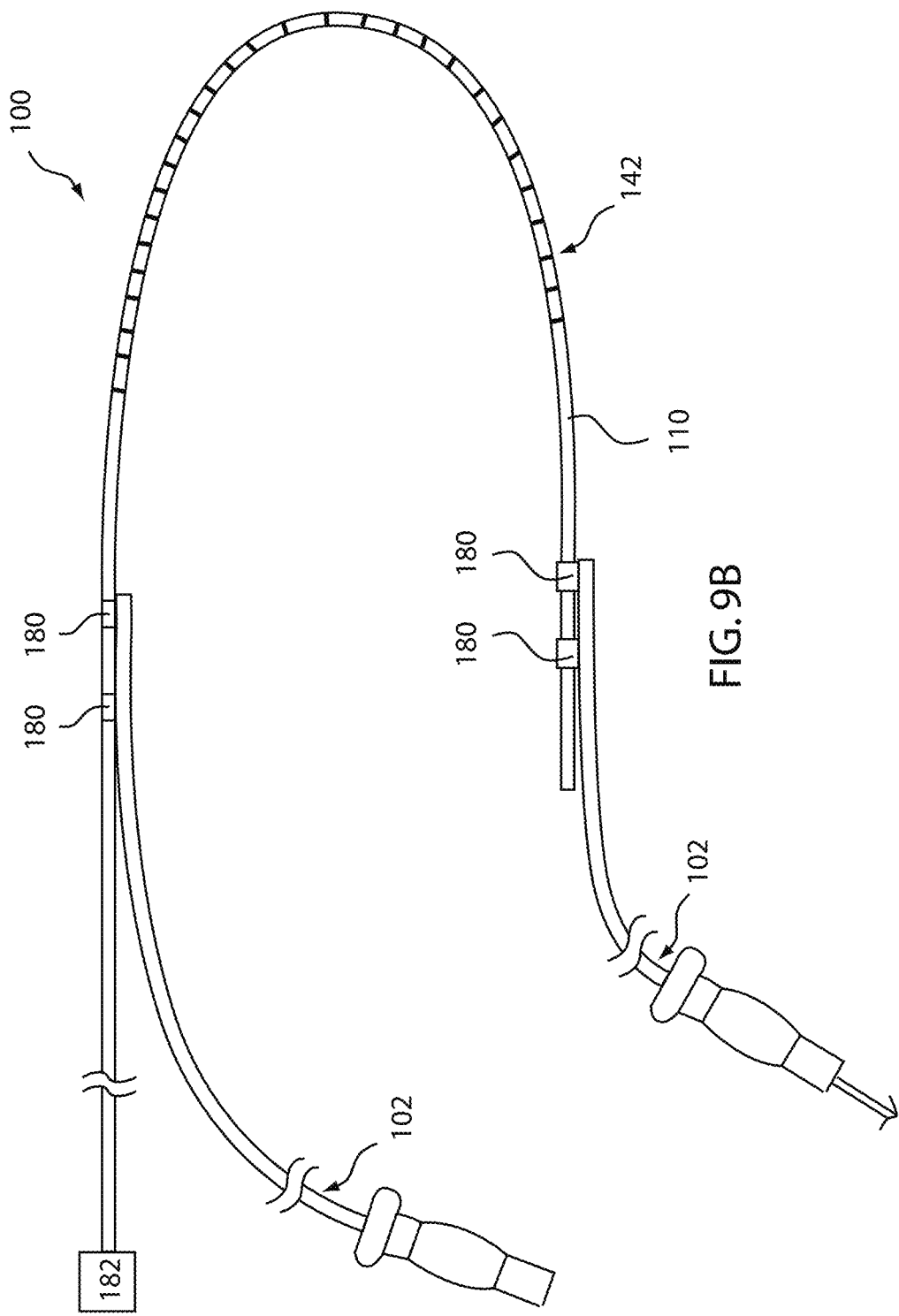

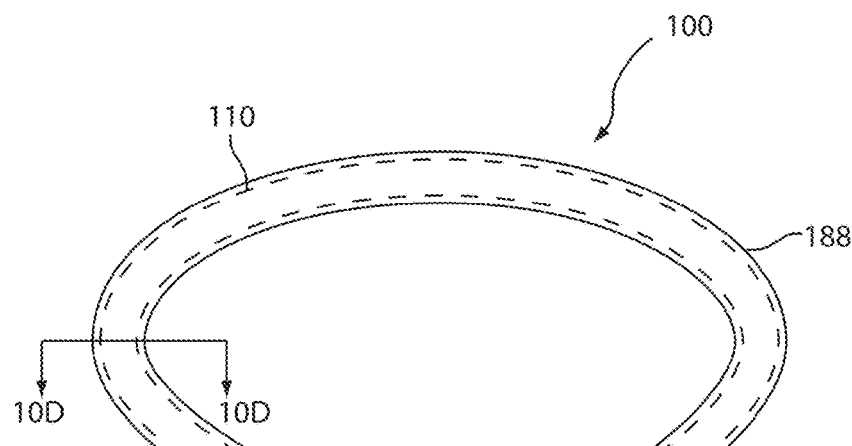
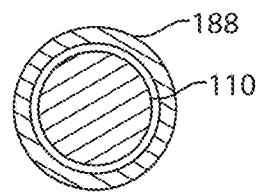
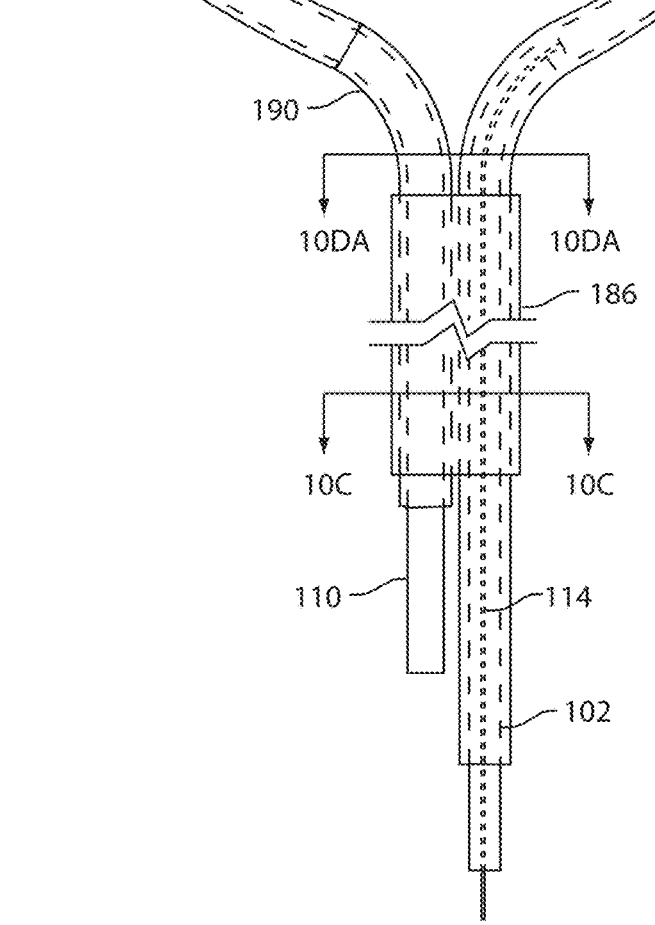
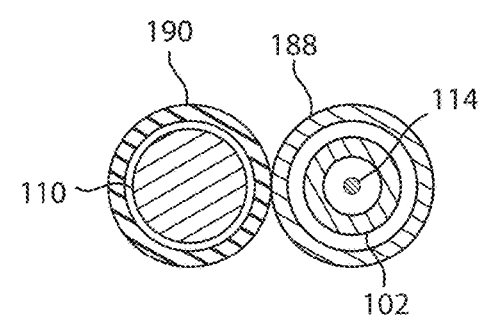
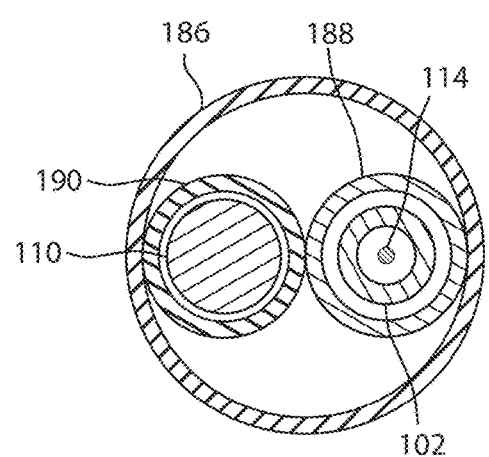
FIG. 10A
FIG. 10C
FIG. 10D
FIG. 10DA

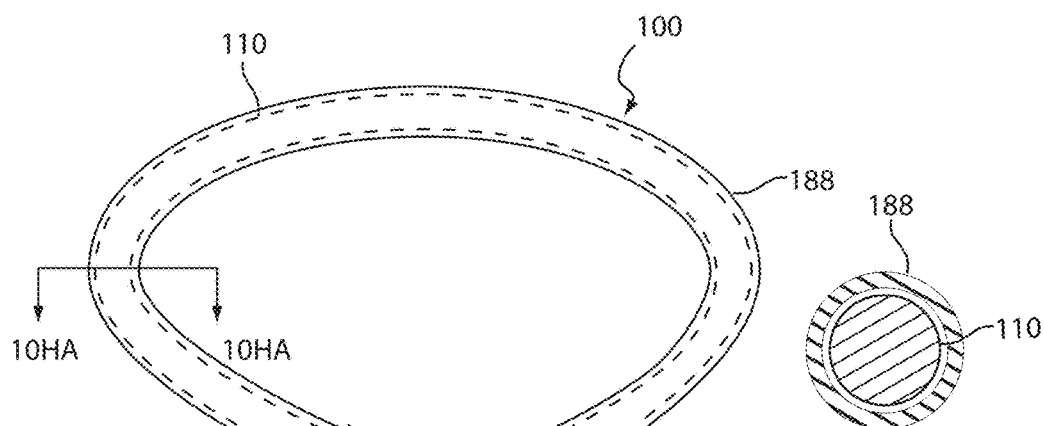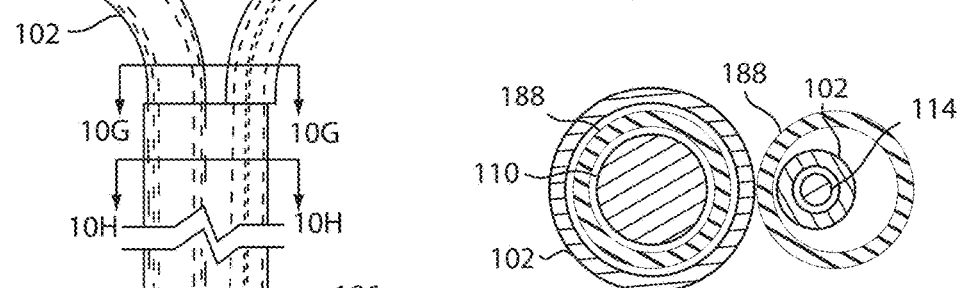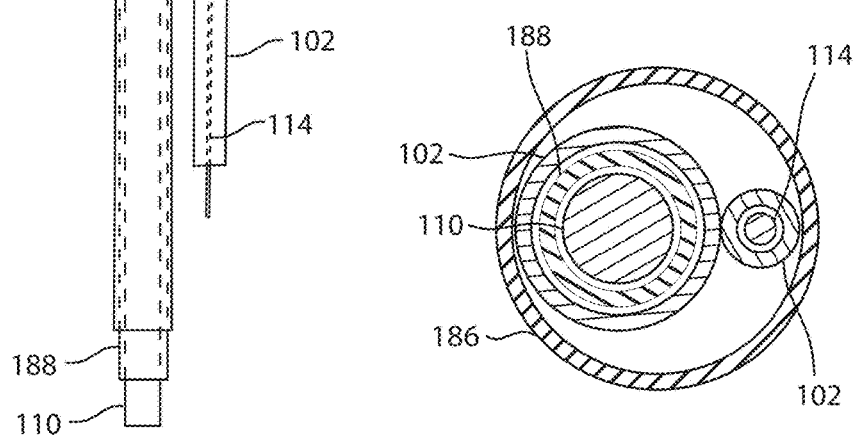
FIG. 10E
FIG. 10HA
FIG. 10G
FIG. 10H

MICROWAVE TREATMENT DEVICES AND METHODS

CROSS-REFERENCE TO RELATED APPLICATIONS

This application is a continuation of U.S. patent application Ser. No. 16/038,921 filed Jul. 18, 2018, which is a continuation of U.S. patent application Ser. No. 14/462,434 filed Aug. 8, 2014, which is a continuation-in-part of U.S. patent application Ser. No. 12/603,134, filed on Oct. 21, 2009, now U.S. Pat. No. 8,808,281 issued Aug. 19, 2014, which claims benefit of U.S. patent Provisional application Nos: 61/107,252 filed on Oct. 21, 2008, 61/162,241 filed on Mar. 20, 2009, 61/180,133 filed on May 21, 2009, and 61/222,409 filed on Jul. 1, 2009 the content of each of which are incorporated herein by reference in their entirety.

FIELD OF THE INVENTION

This invention relates to microwave antennas and delivery systems suitable for positioning various medical components such as microwave antennas within a patient's body.

BACKGROUND OF THE INVENTION

Microwave antennas have been designed to treat various medical conditions by microwave energy delivery. Such microwave antennas may be used for ablating or otherwise modifying tissue. For example, microwave antennas have been used for ablating cardiac tissue to treat cardiac arrhythmias. In several applications of microwave antennas including cardiac ablations, it is very advantageous to have an additional modality located on the microwave antenna. For example, it is very advantageous to have one or more electrophysiological mapping electrodes located on or near a microwave antenna used for cardiac ablation. Such a design enables the user to ablate cardiac tissue using the microwave antenna and also detect electrophysiological signals using the mapping electrodes. Simply adding an additional modality such as mapping electrodes and the conductive wires over a microwave antenna may create a microwave antenna that is unsuitable for clinical use. The additional modality and the conductive wires may absorb microwave energy and become hot. This in turn may cause problems such as burning or charring of tissue, creation of undesirable blood clots and adherence of the microwave antenna to tissue. In addition, additional modality and the conductive wires connected to the additional modality may change the shape of the microwave field emitted by the microwave antenna. This in turn may create a shaped microwave field that is no longer clinically useful. Such a shaped microwave field may also create additional safety issues by undesired microwave energy delivery to healthy tissue. The microwave field may also affect the functioning of the additional modality. Thus, there is a need for microwave antennas that comprise such additional modality such that the safety and the performance of such antennas is not compromised.

Medical diagnostic and surgical procedures generally require that physicians perform many increasingly complex functions within the body. In many of these procedures, the physicians must properly access tissue locations and precisely orient a medical component to perform a diagnostic or surgical procedure. In an ever increasing number of modern surgical procedures, elongate devices are introduced into the target tissue through surgically created access openings or natural openings in the body. Physicians deliberately keep such access openings small to minimize the trauma and the healing burden on the patient. For example, in many catheter-based cardiac procedures, a physician will access internal cardiac tissue by navigating a device through the vasculature until the device can engage the cardiac tissue (e.g. a chamber of the heart). In another example, a physician may create an opening (or rely upon a natural body opening) to access organs and tissues requiring a medical procedure. Traditionally, the desire to minimize trauma to the patient often comes at the expense of the maneuverability of the medical component when compared to a similar open surgical procedure. For instance, a physician working with his hands and having full access to a target site such as during an open surgery has much greater freedom to manipulate one or more medical devices to access target tissue and position and orient the medical devices as needed to perform many functions. Yet, such freedom is lost during minimally invasive procedures and in some open surgical procedures where the physician's access to the target site is limited due to obstructing tissue or organs (such as accessing the interior of an organ through a wall of the organ).

Many conventional approaches attempt to overcome these limitations on maneuverability by providing a device with a steerable distal end. However, these existing devices are unable to provide the optimal amount of articulation and/or manipulation needed within the body, especially when the procedure is performed under fluoroscopy.

To illustrate this point, consider the situation in an open surgical procedure, where a physician is able to use one or both arms to directly manipulate a treatment device onto or along a body structure. The numerous degrees of freedom offered by a single arm (including the hand, the wrist and fingers) enables satisfactory placement of the treatment device. When the physician attempts the same procedure through a limited access (either a smaller incision, use of access ports, intravascularly or even through dissection of other tissues/organs), conventional steerable devices do not provide sufficient maneuverability. For example, catheter-based interventional endocardiac ablations for treating Atrial Fibrillation suffer from shortcomings due to a lack of access to all target regions within the atria. For a successful procedure, it is critical to access specific target regions within the left atrium and create a series of ablations in a specific pattern. Existing steering devices are inadequate in providing this function. This reduces the efficacy of the procedure, increases the procedure times and necessitates the use of very expensive accessory devices such as surgical navigation systems.

In view of the above, there remains a need for a device or system that offers improved positioning of one or more medical device components in various medical procedures. There also remains a need for a device or system that allows a physician the capability to position an appropriate medical component readily and predictably at all desired locations (where the locations may be 2 or 3 dimensional structures) for performing the required procedure such as catheter based cardiac ablation.

BRIEF SUMMARY OF THE INVENTION

The systems and methods described herein are useful in a variety of medical procedures including various diagnostic and therapeutic procedures. In addition, the invention is also useful in open surgical procedures, minimally invasive procedures, as well as procedures performed through natural body openings such as NOTES procedures.

In a significant amount of the disclosure, the heart is used an example of a target organ and cardiac ablation procedures are used as an example of procedures that may be performed using the current invention. However, it should be noted that the various methods and devices disclosed herein may also be used in medical procedures ranging from endovascular cardiac, thoracic cardiac, bronchial, lung, neurological, gynecological, gastro-intestinal, spinal, ENT, laparoscopic, arthroscopic and other endoscopic procedures, robotic including tele-robotic, oncological, etc. In several embodiments herein, portions of the heart are accessed by minimally invasive approach through the inferior vena cava or the superior vena cava. However, one or more portions of the heart may also be accessed through a sub-xiphoid approach (e.g. by penetrating a region such as the apex of a heart ventricle or after accessing the pericardial space) or through a Natural Orifice Transluminal Endoscopic access (e.g. through the stomach or esophagus) or through an open surgical approach (e.g. after a thoracotomy or a sternotomy). One or more portions of the medical systems herein may be introduced into a heart chamber through an atrial appendage of the heart.

In one example, the present disclosure describes methods of delivering microwave energy to tissue. Such methods can include positioning an elongate microwave antenna adjacent to a first region of tissue wherein the antenna comprises a proximal end, a distal end and an antenna axis and the electrode is located over the antenna and between the antenna and the first region of tissue where the wire is connected to the electrode and is electrically isolated from the antenna and wherein a first portion of the wire is exposed to the microwave field emitted by the antenna such that every section of the first portion of the wire is oriented non-parallel to the axis of the antenna; delivering microwave energy to the first location of tissue through the elongate microwave antenna to generate a microwave field where the position of the conductive wire reduces a distortion of the microwave field otherwise resulting from the electrode and to create a first lesion; applying energy through the electrode to diagnose or treat the tissue while maintaining a position of the antenna.

Devices for use in as described herein include microwave emitting systems for delivering microwave energy. In one example such a system includes a transmission line coupleable to a microwave energy source; an elongate microwave antenna having a proximal end, a distal end and an antenna axis, wherein the proximal end of the antenna is electrically coupled to the distal end of the transmission line and where the elongate microwave antenna generates a microwave field upon application of the microwave energy to the transmission line; an electrode positioned along the microwave antenna and between the proximal end and the distal end of the antenna, wherein the electrode is exposed to the microwave field emitted by the antenna and is electrically isolated from the antenna, where the electrode is coupleable to a second power supply; a conductive wire coupled to the electrode wherein the wire is electrically isolated from the antenna and wherein a first portion of the wire exposed to the microwave field emitted by the antenna is disposed relative to the antenna axis such that every section of the first portion of the wire is non-parallel to the axis of the antenna such that arrangement of the conductive wire relative to the antenna reduces distortion of the microwave field due to the electrodes.

Some of the embodiments herein may be broadly described as microwave devices comprising a transmission line such as a coaxial cable and an antenna connected to the coaxial cable. Further, an electrode is located adjacent to or over the antenna. The antenna comprises 1. a radiating element, 2. one or more shaping elements and 3. one or more antenna dielectrics covering one or more portions of the radiating element and/or the shaping element. The electrode can be any diagnostic or treatment modality that allows for a separate application of energy to the tissue region intended for treatment by the antenna.

In embodiments wherein transmission line is a coaxial cable, the radiating element may be a continuation of the inner conductor of the coaxial cable or may be an additional conductive element electrically connected to the inner conductor of the coaxial cable. The radiating element radiates a microwave field that is characteristic of its specific design. The radiated microwave field causes agitation of polarized molecules, such as water molecules, that are within target tissue. This agitation of polarized molecules generates frictional heat, which in turn raises the temperature of the target tissue. Further, the microwave field radiated by the radiating element may be shaped or otherwise redistributed by one or more shaping element(s) in the antenna. In one embodiment, the shaping element(s) are made of an electrically conductive material (e.g. one or more metallic objects of various sizes, shapes, orientations, etc.). In this embodiment, the shaping element(s) may be electrically connected to the outer conductor or shielding element of the transmission line (e.g. the outer conductor of a coaxial cable). In an alternate embodiment, the shaping element(s) are not in direct electrical conduction with the outer conductor or shielding element of the transmission line e.g. the outer conductor of a coaxial cable. The one or more antenna dielectrics may cover one or more portions of one or both of: radiating element and shaping element. The antenna dielectrics may be used for changing the propagation of the microwave field from one or both of: radiating element and shaping element to the surrounding. The antenna dielectrics may be used for changing the matching of the antenna.

The one or more diagnostic or treatment modalities may be a part of the microwave device or may be located on an additional device that is located around the microwave device. One or more conductive wires may be connected to the diagnostic or treatment modalities that connect the diagnostic or treatment modalities to an external circuit. The diagnostic or treatment modalities and the conductive wires connected to the diagnostic or treatment modalities are located within the microwave field emitted by the antenna. The novel configuration and placement of such diagnostic or treatment modalities and their conductive wires ensures that the temperature of the additional modality and the conductive wires does not exceed a safe level during clinical use. Further, the presence of the additional modalities and the conductive wires does not affect or minimally affects the shape of the microwave field emitted by the microwave antenna. This in turn ensures that the safety and the performance of such antennas is not compromised.

Various additional features may be added to the devices disclosed herein to confer additional properties to the devices disclosed herein. Examples of such features include, but are not limited to one or more lumens, ability to apply a vacuum or suction to the target anatomy, ability to visualize one or more regions of the target anatomy, ability to limit the depth of insertion into the target anatomy, ability to deploy the antenna, ability to connect to a source of energy, etc.

The dimensions or other working parameters of the devices disclosed herein may be adjustable or programmable based on user inputs. The user input may be based on factors such as patient's anatomical data including anatomical dimensions and the desired level of safety and efficacy.

The various microwave antennas and the microwave engineering principles disclosed herein may be also used in a variety of non-medical applications. The near field of the microwave antennas disclosed herein may be used on target materials such as food, industrial products, semiconductors, etc. The near field of the microwave antennas disclosed herein may be used for cooking or heating foods, in industrial processes for drying and curing products, in semiconductor processing techniques to generate plasma for processes such as reactive ion etching and plasma-enhanced chemical vapor deposition (PECVD).

The device and methods disclosed herein may be used with or without modifications to create one or more point, linear, area or volumetric lesions. The present invention discloses various embodiments of flexible, low-profile devices that can be inserted non-invasively or minimally invasively into or near the target tissue.

The present invention also comprises medical systems for steering medical components or devices in the anatomy. In one embodiment, the medical system comprises at least a first and second arm, each arm having a maneuverable distal portion and a proximal portion, where manipulation of the respective arm's proximal portion permits articulation of the arm's maneuverable distal portion independently of the other respective arm, and a medical component coupled to the first arm and extendable from the first arm's maneuverable distal portion, the medical component being engageable with the second arm's maneuverable distal portion, such that when coupled to both arms, movement of either maneuverable distal portion alters a profile or position of the medical component allowing for positioning of the medical component to perform the medical procedure.

In another embodiment, the invention includes a medical system for performing a medical procedure on or in a patient, the system comprising a first arm having a maneuverable distal portion and a proximal portion, wherein manipulation of the arm's proximal portion permits articulation of the arm's maneuverable distal portion and a medical component coupled to the first arm and extendable from the first arm's maneuverable distal portion. Movement of the maneuverable distal portion alters a profile or position of the medical component allowing for positioning of the medical component to perform the medical procedure.

In some variations, the medical components extend through an arm in a concentric or coaxial manner. However, the invention also includes components that extend parallel to the arm, or that extend along the arm or a portion thereof in a non-concentric manner. One or more arms may be removably coupled to the medical component(s) via a grasping structure. An example of such grasping structure includes a releasable hook, ring, or jaws. The arms can fully or partially hollow. One or more arms may be concentric with each another. One or more arm may be introduced via one or more access ports and pathways.

For purposes of this specification, the term medical component is intended to include a medical device or portion thereof that is adapted to provide a visual, diagnostic, or treatment procedure. For example, and as described below, in one variation, the system can include a first medical component comprising an energy delivery device configured to deliver energy (e.g. microwave, radiofrequency, DC, ultrasound, laser, a cryogenic field) to or from tissue and a second medical component (such as a guidewire, rail, tether, etc.) that is used to direct the energy delivery device towards a target site. The first and second medical component can be parts of the same device or can be separate medical devices.

Examples of medical components, include, but are not limited to, therapeutic devices such as ablation devices for imparting a treatment relative to a target tissue, diagnostic devices such as mapping catheters for providing physiological information regarding a target tissue; positioning devices which include elements for providing additional positioning of additional functional devices (e.g., guidewires, rails, tethers, introducer catheters, sheaths, etc.), imaging devices, or non-imaging feedback devices (such as a Doppler catheter). The medical component need not have a specific physical structure, for example the arms of the inventive system can be adapted to deploy a simple tube that administers a chemical ablating agent at a desired location or deploy an additional fluid used during, and in support of, the medical procedure, for example deployment of contrast agent to provide a clearer view of the anatomy in support of a procedure performed within a patient's heart. In yet additional variations, the medical components can include separate components used to provide a single diagnostic procedure or medical of the same medical procedure. For instance, when using a radiofrequency energy modality, the medical component could include a first electrode while the second component can include a second electrode (either the opposite or same polarity).

The tether member may consist of a string or wire like structure that is used to simply pull the medical component through one or both arms. In additional variations, the tether member can include a flexible tether member that, when deflected, assumes a curvilinear shape based on the structural characteristics of the tether. As discussed below, this allows the medical component to assume a "U" shaped configuration that can assist in performing the medical procedure. The tether member may also comprise one or more conductive wires connected to one or more diagnostic or therapeutic modalities. In one embodiment, the one or more conductive wires are a part of the tether. In one embodiment, the one or more conductive wires extend along the tether and are attached to the tether at one or more regions. In one embodiment, the one or more conductive wires extend along the tether and are unattached to the tether.

Another aspect of the system is the ability to control movement of the distal portions of the arms from the proximal portions. In one embodiment, the arms include handle portions on the proximal end. The handle portions can include one or more steering control mechanisms. The movement of the arms can occur in any three dimensional space.

In an additional embodiment, the devices and method described herein include a medical system for performing a medical procedure on or in a patient, the system comprising a medical component, a first arm having a distal portion and a proximal portion, where manipulation of the first arm's proximal portion permits articulation of the first arm's distal portion and where the medical component is coupled to and advanceable relative to the distal portion of the arm, a second arm having a distal portion and a proximal portion, where manipulation of the second arm's proximal portion allows for articulation of the second arm's distal portion, a rail member or tether coupled to the medical component and extending through the second arm, and where the first and second arms are configured to be manipulated independently, and where manipulation of the first or second arm alters a profile or position of the medical component allowing for positioning of the medical component.

BRIEF DESCRIPTION OF THE SEVERAL VIEWS OF THE DRAWINGS

FIG. 1B shows a side view of an embodiment of a microwave antenna comprising one or more electrophysiological mapping or pacing or RF ablation electrodes.

FIG. 1C shows a section through an embodiment of coaxial cable usable for the ablation device of FIGS. 1A, 1B and for other ablation devices disclosed herein.

FIG. 1D shows a longitudinal section of the embodiment of the ablation device of FIG. 1A through the distal end of the coaxial cable.

FIG. 1P shows a side view of a simulated SAR profile generated by an antenna similar to the antenna of FIG. 1A.

FIG. 1Q shows a side view of a simulated SAR profile generated by an antenna similar to the antenna of FIG. 1A but having four extra electrodes spaced at regular intervals along the length of the antenna wherein each electrode is connected to a conductive wire arranged in a first configuration.

FIG. 1R shows a side view of a simulated SAR profile generated by an antenna similar to the antenna of FIG. 1A but having four extra electrodes spaced at regular intervals along the length of the antenna wherein each electrode is connected to a conductive wire arranged in a second configuration.

FIG. 1S shows a view of the distal region of the ablation device similar to the ablation device used in FIGS. 1K, 1M and 1O.

FIG. 1T shows an antenna similar to the antenna in FIG. 1A being slidably introduced through the lumen of a functional tube.

FIG. 1U shows a side view of a simulated SAR profile generated by a 915 MHz monopole antenna.

FIG. 1V shows a side view of a simulated SAR profile generated by a monopole antenna similar to the antenna of FIG. 1U but having four extra electrodes spaced at regular intervals along the length of the antenna wherein each electrode is connected to a conductive wire arranged in a first configuration.

FIG. 1W shows a side view of a simulated SAR profile generated by a monopole antenna similar to the antenna of FIG. 1U but having four extra electrodes spaced at regular intervals along the length of the antenna wherein each electrode is connected to a conductive wire arranged in a second configuration.

FIG. 1AA shows an embodiment of a medical system comprising a sheath or arm that is used to introduce and position a medical component.

FIG. 1AB shows an embodiment of a working model of the medical system similar to that shown in FIG. 1A.

FIGS. 1AC and 1AD show two configurations of an embodiment of a medical system comprising a medical component introduced in the anatomy through an arm.

FIGS. 1AE and 1AF show two configurations of an embodiment of a medical system wherein a medical component and a second medical component are introduced in the anatomy through an arm.

FIGS. 1AG-1AK show various steps of a method of introducing a medical component comprising a bendable or foldable region into the anatomy through an arm.

FIG. 4F-4G shows a medical system comprising two arms with pre-shaped distal portions used to manipulate a medical component.

FIG. 4C shows an alternate embodiment of the medical system of FIG. 4A showing a first medical component comprising six functional elements.

FIG. 4D shows an alternate embodiment of the medical system of FIG. 4A showing a first medical component comprising a long, linear active region.

FIG. 4E shows an alternate embodiment of the medical system of FIG. 4A showing a first medical component comprising a centrally located active region and multiple functional elements on both sides of the active region.

FIG. 4F shows an alternate embodiment of the medical system of FIG. 4A showing a first medical component comprising multiple functional elements and a tether or spline.

FIG. 4G shows an alternate embodiment of the medical system of FIG. 4A showing an assembly comprising two medical components comprising multiple functional elements joined at their distal ends by a tether or spline.

FIGS. 6A-6G show various alternate embodiments of the medical system of FIG. 4A comprising an active region comprising one or more one or more functional elements in the form of radiofrequency electrodes.

FIGS. 6H-6K show some examples of a medical system with several possible orientations of regions of a medical component.

FIGS. 6L and 6M illustrate an embodiment of a medical component and a second medical component having respective mating portions.

FIG. 6N illustrates an embodiment of a medical system comprising a single medical component extending between adjacent arms.

FIG. 9A shows an example of a medical system comprising a second medical component that advances over a first medical component.

FIG. 9B illustrates an embodiment of the present invention wherein a medical component is coupled adjacent to two arms via coupling portions rather than being introduced through the arms as shown in some of the previous figures.

FIGS. 10A-10DA show various views of a first embodiment of a medical system comprising a hollow tube through which an elongate looped medical component is slidably introduced.

FIGS. 10E-10HA show various views of a second embodiment of a medical system comprising a hollow tube through which an elongate looped medical component is slidably introduced.

DETAILED DESCRIPTION OF THE INVENTION

Figure 1E:
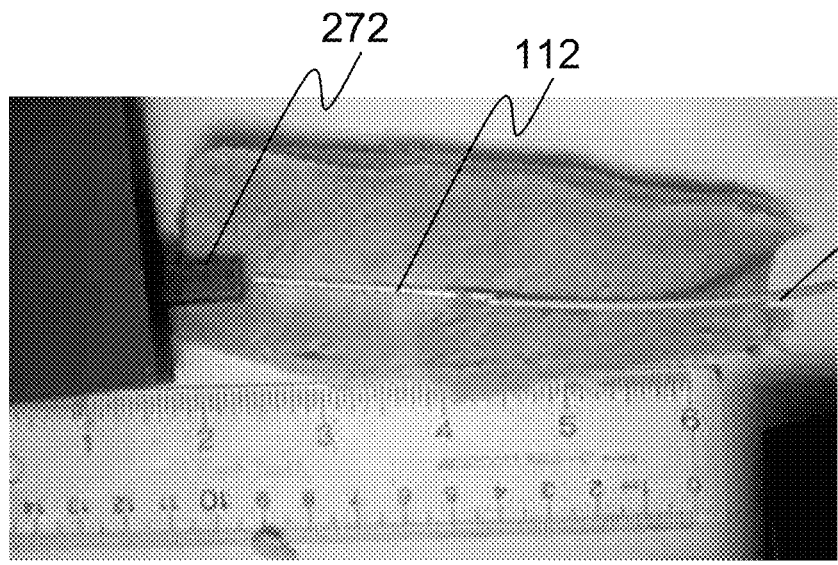
FIGS. 1E-1G show the method steps of a method of creating two overlapping lesions in a tissue.

The present invention discloses devices and methods for treating tissue with microwave energy. In several method embodiments, microwave energy is used for ablating tissue e.g. for treating atrial fibrillation by controlled ablation of left atrial tissue, etc. The systems and methods described herein are useful in a variety of medical procedures including various diagnostic and surgical procedures. In addition, the invention is also useful in open surgical procedures, minimally invasive procedures, as well as procedures performed through natural body openings.

In a significant amount of the disclosure, the heart is used as an example of a target organ and cardiac ablation procedures are used as an example of procedures that may be performed using the current invention. However, it should be noted that the various methods and devices disclosed herein may also be used in medical procedures including, but not limited to: endovascular cardiac, thoracic cardiac, bronchial, lung, gynecological, gastro-intestinal, spinal, ENT, laproscopic, arthroscopic procedures, etc.

Microwave thermal ablation does not depend on the conduction of electricity to tissue unlike RF ablation. Thus, devices using microwave thermal ablation such as some of the devices disclosed herein don't need good contact with tissue. They can function well even without perfect contact with the target tissue. Thus, the devices disclosed herein do not require extremely precise placement in tissue, thereby reducing the dependence of procedure outcome on physician skills. In some embodiments, the devices herein are designed to have a proximal shaft and a distal microwave emitting portion comprising an antenna. The proximal shaft comprises a transmission line such as a flexible coaxial cable that delivers microwave energy from a microwave generator to the microwave emitting portion. The shaft can be designed to be slim (e.g. <3 mm in diameter) to enable the introduction of the ablation device through narrow openings. The shaft can be designed to be flexible such that minimal forces are exerted on bodily tissues during the introduction of the ablation devices into the anatomy. The flexible nature of the shaft enables the shaft to take the natural shape of passage during introduction instead of distorting the passage by the shaft of the device. The designs of the coaxial cables disclosed herein confer sufficient flexibility to the device shaft such that the device shaft is capable of bending by more than 45 degrees when it experiences distorting forces by the anatomy. If desired, the device shaft may be made stiffer by adding one or more coatings, coverings, stylets and other stiffening elements.

Several of the experiments herein were performed at 0.915 GHz or 2.45 GHz ISM band. Antennas, methods, etc. disclosed herein may be used with or without modifications at other frequencies including, but not limited to ISM bands of 0.433 GHz, 5.8 GHz, etc. The microwave power generator may be magnetron based or solid state. The microwave power generator may be single or multi-channel. The microwave power generator used for the experiments comprised a Vector Network Analyzer (Agilent 8753 series) and amplifier modules build in-house using transistors from Freescale Semiconductor (Austin, Texas). The power measurement was made using a power meter (ML2438A Power Meter, Anritsu Company, Richardson, TX). Similar devices and components can be used to design the microwave generator for clinical use with the devices and methods disclosed herein.

In the experiments, where desired, a fiber optic thermometry system (FOT Lab Kit by LumaSense Technologies, Santa Clara, CA) was used to measure the temperature at several locations in the tissue. The fiber optic thermometry system was used since it has no metallic components that might interfere with the microwave field. Similar non-interfering thermometry may be used to measure the temperature at one or more locations during an ablation procedure.

Several devices and methods described herein provide a physician with an improved ability to remotely position one or more medical components on or in a target tissue location. The ability to position such medical components allows the physician to perform one or more medical procedures with improved accuracy and efficiency where direct use of the physician's arms is not possible. Although variations of the system described below primarily discuss placement of one or more energy delivery devices on tissue, such variations are for exemplary purposes only. The features of the system can be used to position any number or type of medical components including, but not limited to: implants or implant delivery devices, diagnostic devices, imaging devices, biopsy devices, radiation emitting devices, drug delivery devices, radio-opaque markers, valvular annuloplasty devices, suturing devices, etc.

The system could also be used as a stable platform to perform minimally invasive surgical procedures. In such procedures, the devices and methods disclosed herein may be used to cut, suture, coagulate or remove tissue for example. Any suitable imaging modality may be used to visualize the anatomy and/or one or more of the devices disclosed herein while performing any of the procedures disclosed herein. Examples of such imaging modalities include, but are not limited to endoscopes (e.g. colonoscopes, laparoscopes, thoracoscopes, bronchoscopes, cystoscopes, colposcopes, hysteroscopes, arthroscopes, etc.), X-rays, Computed tomography (CT), fluoroscopy, ultrasound imaging including intravascular and intracardiac ultrasound imaging, intra-cardiac electrophysiological three dimensional mapping, MRI, PET, near infra-red imaging, etc.

Figure 1F:
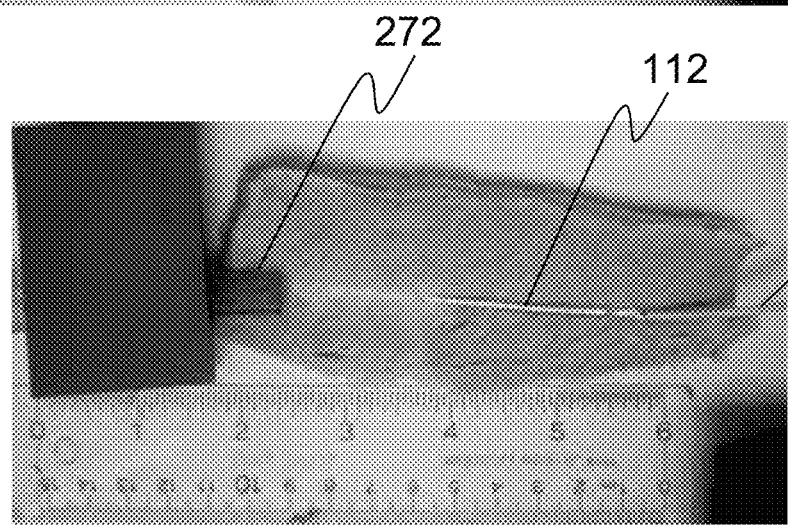
Figure 1G:
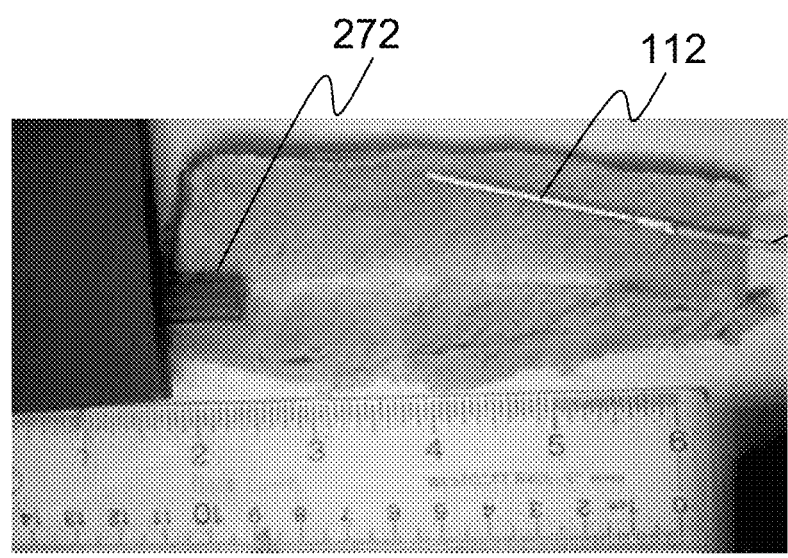
Figures 1H, 1I:
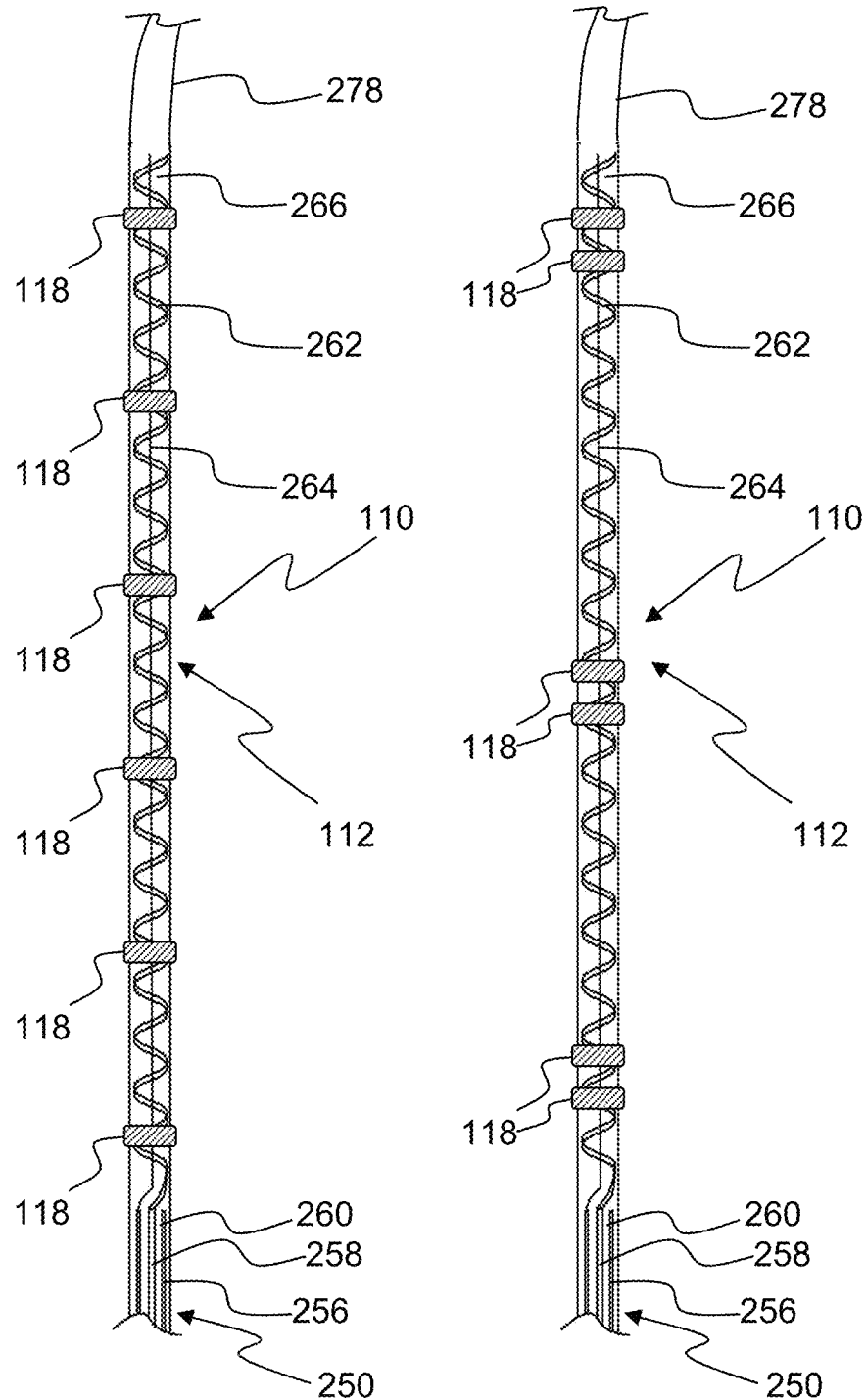
FIG. 1H shows a side view of an embodiment of a microwave antenna comprising multiple electrophysiological mapping or pacing electrodes that are spaced in regular intervals along the length of the antenna.
FIG. 1I shows a side view of an embodiment of a microwave antenna comprising multiple electrophysiological mapping or pacing electrodes that are spaced in pairs along the length of the antenna.
Figure 1J:
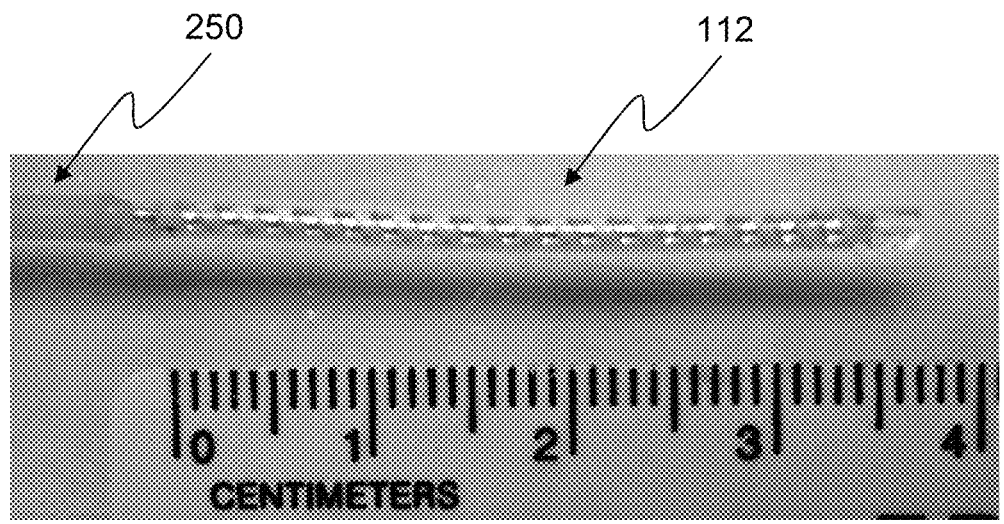
FIG. 1J shows a side view of a functional microwave antenna with a design similar to the design shown in FIG. 1A.
Figure 1K:
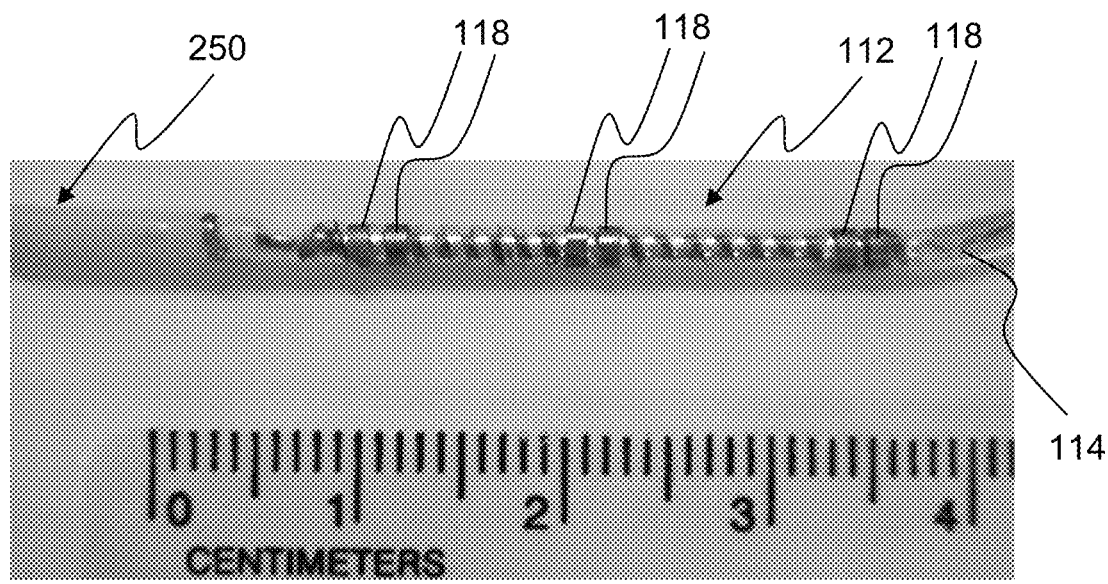
FIG. 1K shows a side view of a functional microwave antenna having additional electrodes.
Figure 1L:
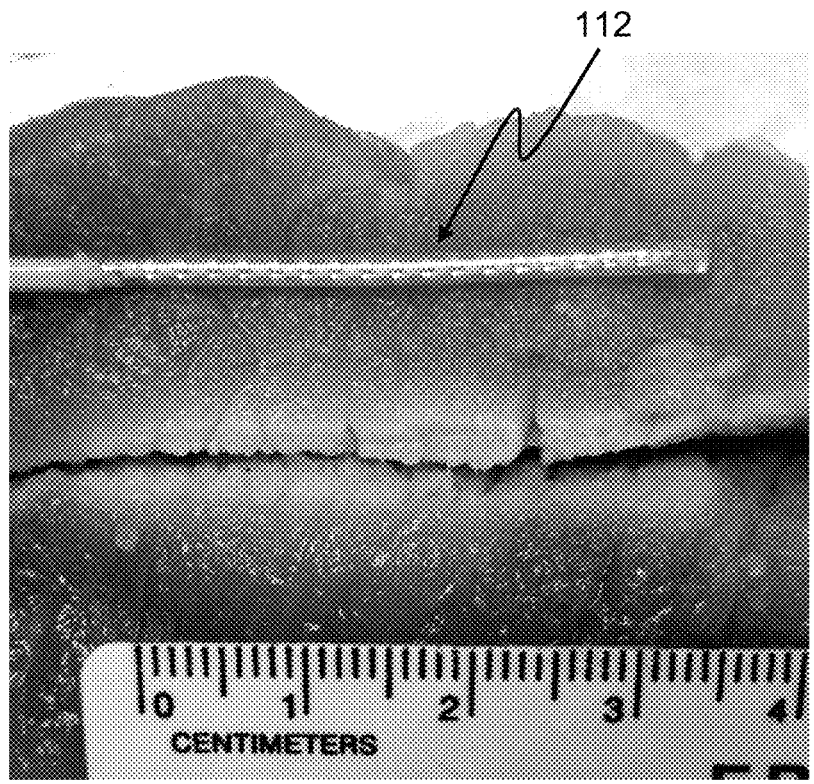
FIGS. 1L and 1M show surface images of lesions obtained by ablating the surface of porcine muscle tissue using the antennas shown in FIGS. 1J and 1K respectively.
Figure 1M:
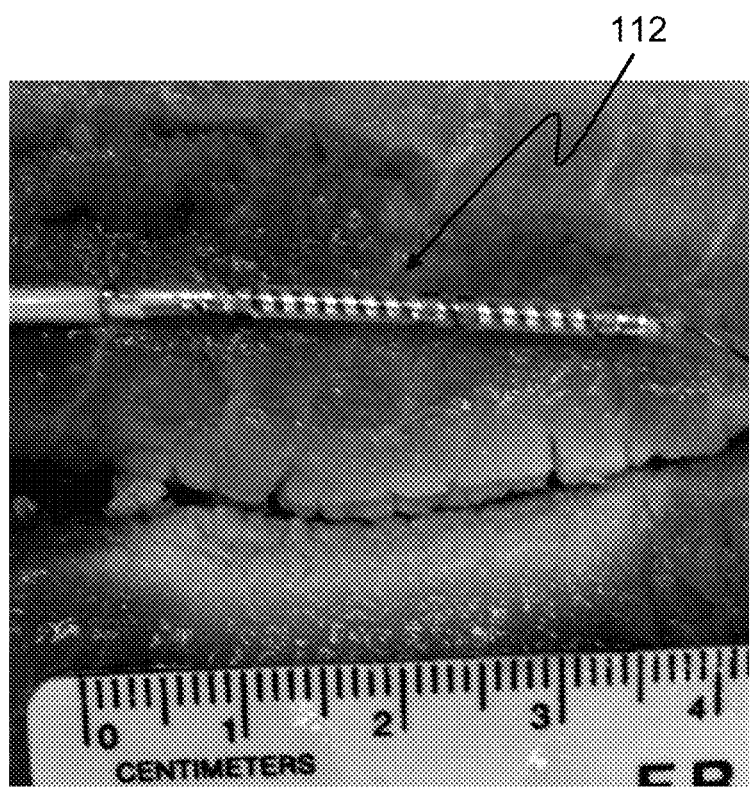
Figure 1N:
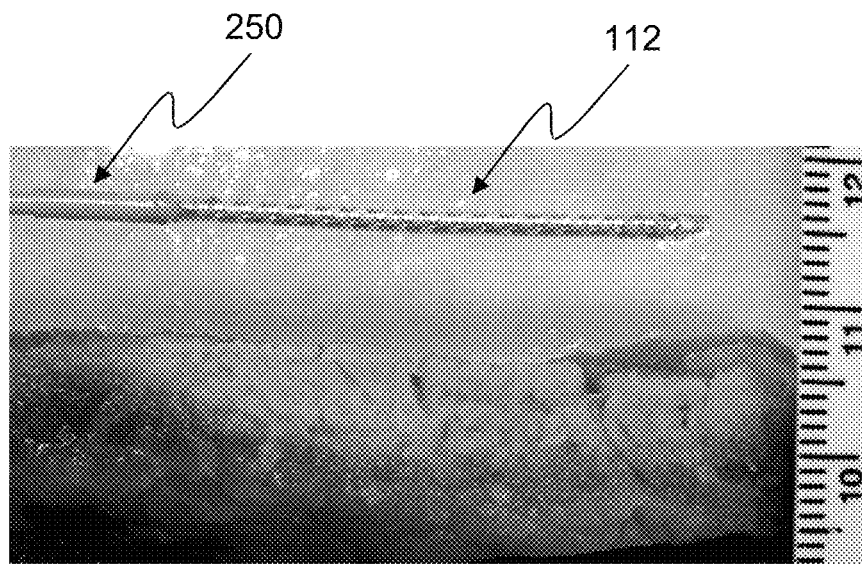
FIGS. 1N and 1O show sections of the porcine tissue in FIGS. 1L and 1M showing the depth of the lesions obtained by the antennas in FIGS. 1J and 1K respectively.
Figure 1O:
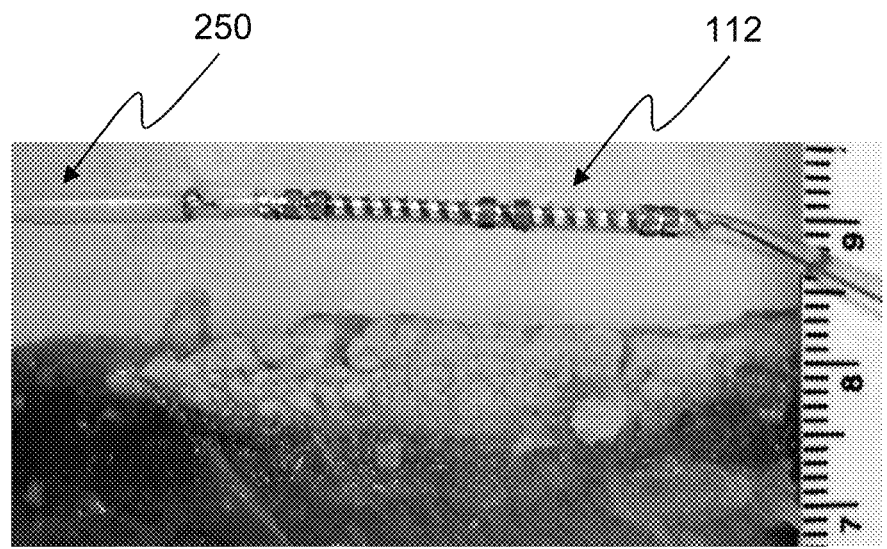
Figure 1A:
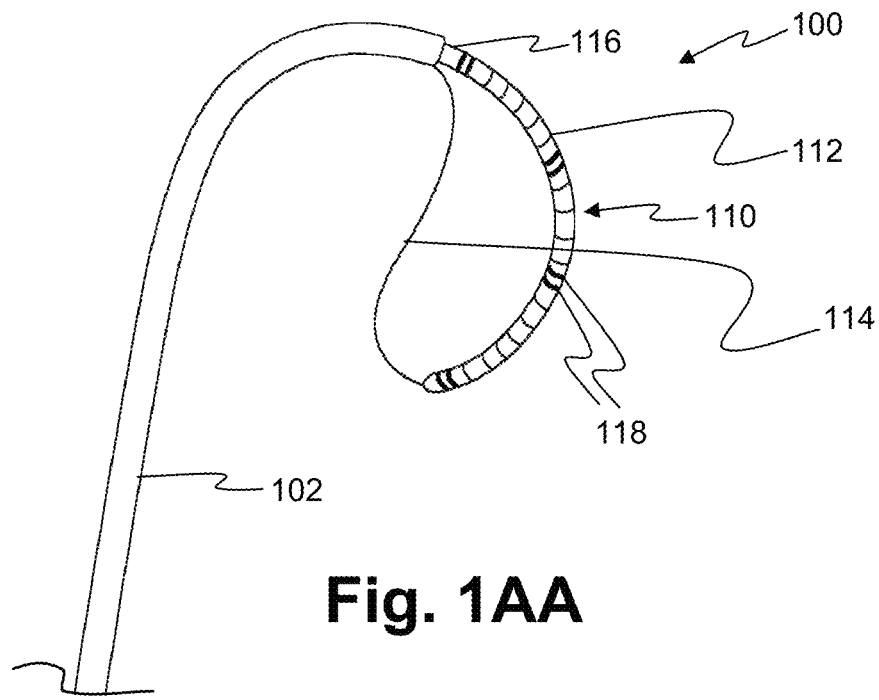
FIG. 1A shows a side view of an embodiment of a linear microwave antenna of the present invention comprising a radiating element and a microwave field shaping element.
Figure 1A:
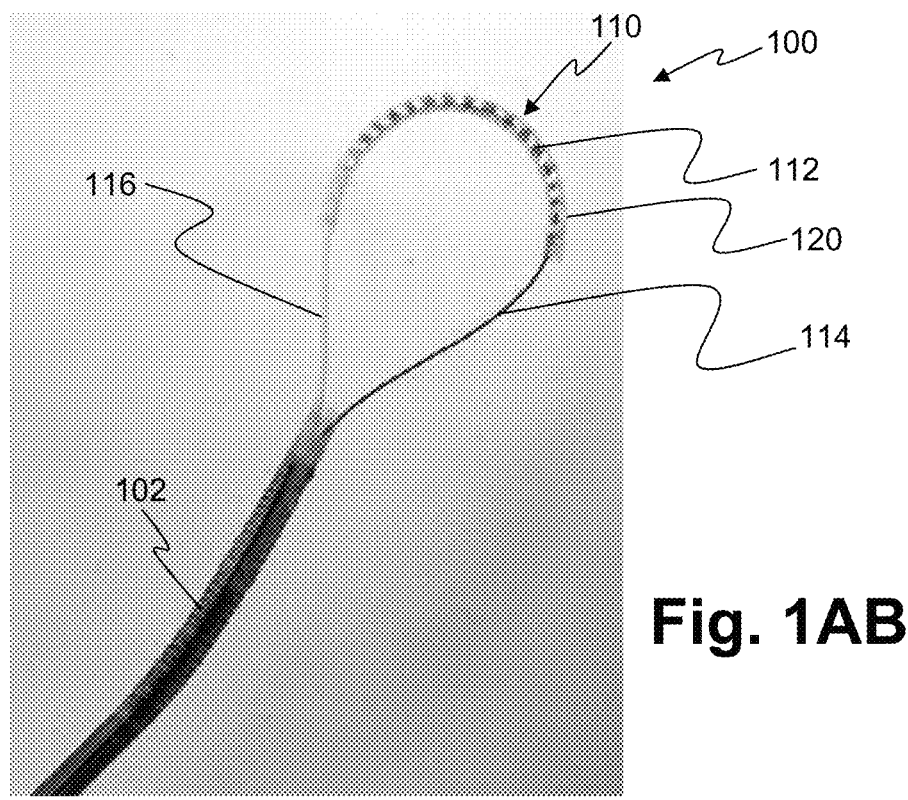
Figure 1A:
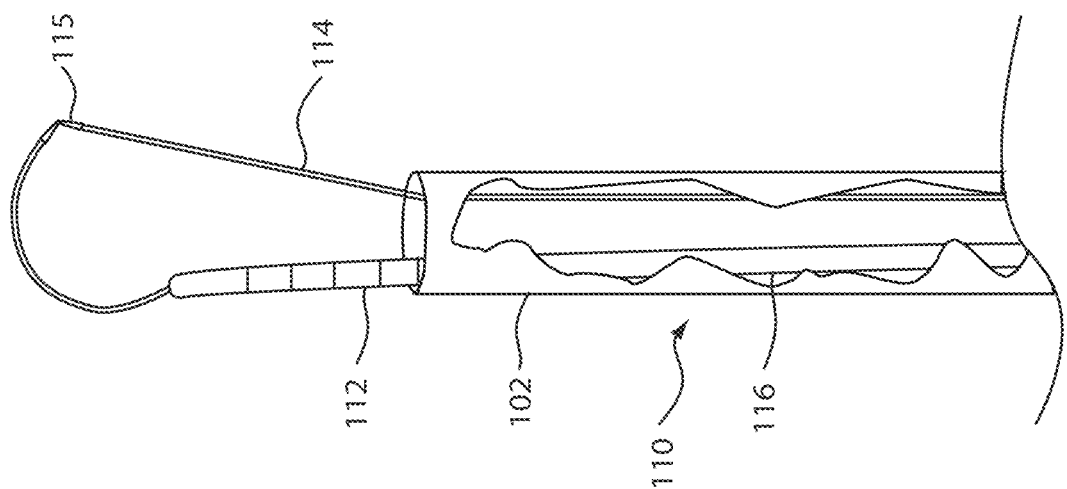
Figure 1A:
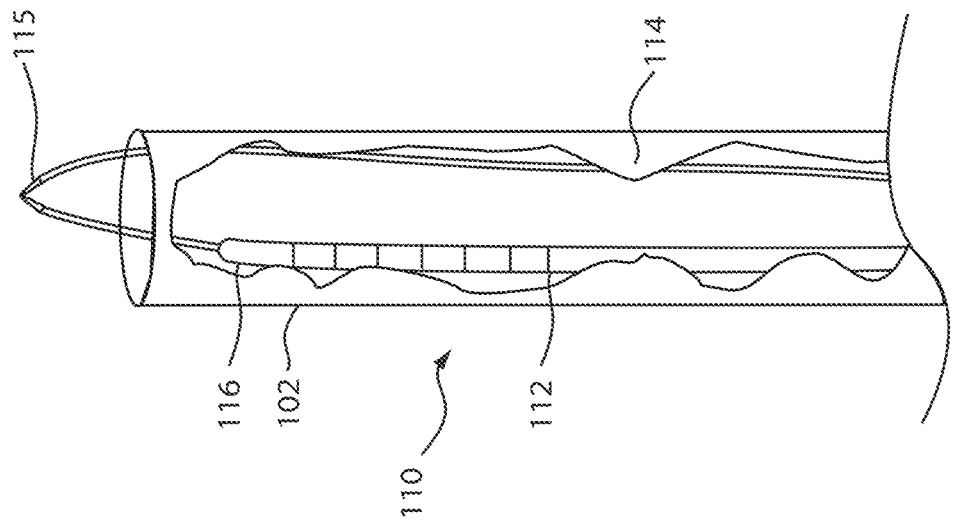
Figure 1A:
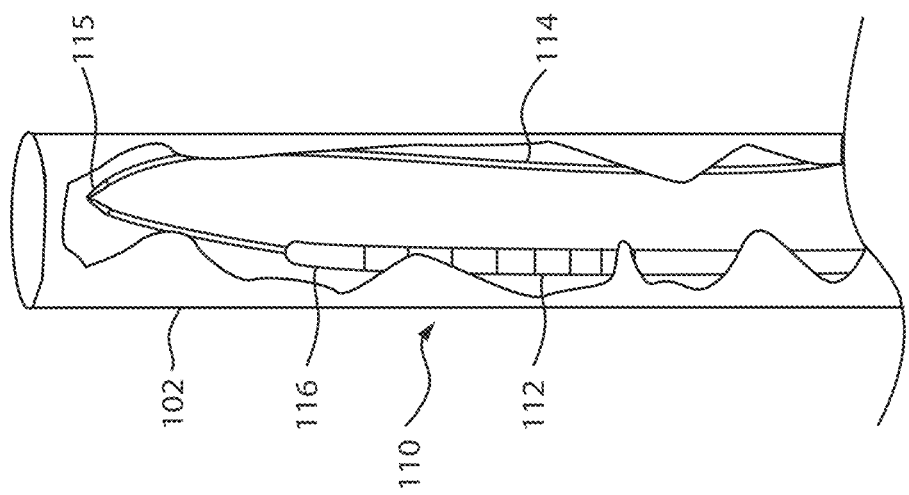

In FIG. 1A, microwave ablation device 110 comprises a transmission line such as a coaxial cable 250. A working element 112 such as an antenna 112 is connected to the distal end of coaxial cable 250. FIG. 1A shows microwave ablation device 110 divided into a first zone Z1 and a second zone Z2 by an imaginary transition line 254. First zone Z1 is proximal to second zone Z2. Transition line 254 is defined by the distal end of coaxial cable 250 and is substantially perpendicular to the axis of coaxial cable 250 at the distal end of coaxial cable 250. In the embodiment shown in FIG. 1A, the distal region of coaxial cable 102 lies entirely within first zone Z1 and antenna 112 lies entirely within second zone Z2. In one embodiment, a single microwave signal is fed to antenna 112 through coaxial cable 250. Antenna 112 generates a microwave field. The near field of the microwave field generated by antenna 112 may be used for tissue ablation.

In FIG. 1A, antenna 112 comprises a radiating element 262 and a shaping element 264. Radiating element 262 may be made of a variety of conducting materials e.g. metals, conductive polymers, materials with embedded conductive particles, etc. When microwave energy is delivered through coaxial cable 250 to antenna 112, a first microwave field is emitted by radiating element 262. The first microwave field interacts with shaping element 264. This interaction induces a leakage current on shaping element 264. The leakage current in turn creates a second microwave field. The first microwave field and the second microwave field together combine to produce a unique shaped microwave field of antenna 112 that is clinically more useful that the unshaped microwave field generated by an antenna 112 comprising only radiating element 262. Thus the original microwave field is redistributed by the design of shaping element 264.

Shaping element 264 alone is not capable of functioning as an antenna; rather shaping element 264 shapes or redistributes the electromagnetic or microwave field emitted by radiating element 262 to produce a clinically improved microwave field. It should be noted that there is no direct electrical conduction between radiating element 262 and shaping element 264. Antenna 112 further comprises one or more antenna dielectrics 266 covering one or more portions of one or both of: radiating element 262 and shaping element 264. In FIG. 1A, an antenna dielectric 266 covers the entire radiating element 262. Any of the antenna dielectrics 266 disclosed herein may be used to shape the microwave field and to optimize the performance of antenna 112. Any of the antenna dielectrics 266 disclosed herein may be replaced by one or more conducting polymers.

A microwave field couples to the nearest conductive path. In prior art monopole antennas, the nearest conductive path is provided by the shielding element of the transmission line (e.g. the outer conductor 256 of the feeding coaxial cable 250). This causes a strong concentration of the microwave field in the junction between antenna 112 and transmission line 250. However, in several embodiments of antenna 112 disclosed herein, the nearest conductive path is provided by shaping element 264. Thus the microwave field couples to shaping element 264 instead of coupling to the shielding element of the transmission line (e.g. the outer conductor 256 of the feeding coaxial cable 250). Therefore, minimal microwave field is coupled proximally to the shielding element of the transmission line. This in turn creates a unique, shaped or redistributed microwave field that does not significantly extend proximally to antenna 112 as shown in FIGS. 1P and 1Q. Further, the combination of radiating element 262 and shaping element 264 improves the power deposition of antenna 112.

Antennas disclosed herein may comprise one or more shaping elements 264 made of a variety of conducting materials e.g. metals, conductive polymers, materials with embedded conductive particles, etc. Such shaping elements 264 may comprise one or more dielectrics layers to insulate the shaping element 264 from surrounding tissue. Examples of such shaping elements 264 include, but are not limited to: straight or curved segments of metallic elements, elements with a circular or oval shape, elements with a polygonal shape (e.g. triangular, square, rectangular, pentagonal, etc.), multiple elements joined together by one or more electrically conducting joint(s), multiple elements joined together by a non-electrically conducting joint(s), elements with multiple curves, symmetrically arranged segments of elements, non-symmetrically arranged segments of elements, etc.

In one embodiment, radiating element 262 is a continuation of the inner conductor 258 of a coaxial cable 250. In one embodiment, shaping element 264 is made of an electrically conductive material e.g. a metal and is electrically connected to a region of outer conductor 256 of coaxial cable 250. In an alternate embodiment, antenna 112 comprises one or more conductive shaping elements 264 that are electrically isolated from outer conductor 256. In this embodiment, one or more shaping elements 264 function as passive radiators or parasitic elements of antenna 112. In one embodiment, shaping element 264 is designed to act as a microwave shielding element and/or a microwave reflecting element.

Further, antenna 112 may be designed to be sufficiently flexible such that during and after introduction and deployment of antenna 112 in the anatomy, the anatomy experiences only slight forces from antenna 112. This may be achieved by designing an antenna 112 comprising one or more flexible radiating elements 262, one or more flexible shaping elements 264 and one or more flexible antenna dielectric materials. Sufficiently flexible antennas may reduce damage to healthy tissue as well as potentially reduce the pain experienced by the patient during the introduction and deployment. Antenna 112 may be introduced through a small lumen. This enables the introduction of antenna 112 through narrow catheters, shafts, introducers and other introducing devices. Further, this enables the introduction of antenna 112 through small natural or artificially created openings in the body. Further, antenna 112 may be designed to have an atraumatic distal end to reduce the risk of perforation of tissue. The flexible nature of antenna 112 enables antenna 112 to take the natural shape of an introduction passage during introduction instead of distorting the passage. In one embodiment, the length of straightened radiating element 262 measured along the radiating element 262 from the distal end of coaxial cable 250 or other transmission line until the distal end of radiating element 262 is an odd multiple of one quarter of the effective wavelength at one of: 433 MHz ISM band, 915 MHz ISM band, 2.45 GHz ISM band and 5.8 GHz ISM band. For example, the length of radiating element 262 may be three quarters of the effective wavelength at the 915 MHz ISM band. The effective wavelength is dependent on the medium surrounding the antenna and the design of a dielectric covering on the radiating element 262. The design of the dielectric covering includes features such as the type of dielectric(s) and thickness of the dielectric layer(s). The exact length of the radiating element 262 may be designed to get good impedance matching.

In any of the embodiments herein, one or more outer surfaces of radiating element 262 may be covered with one or more layers of antenna dielectrics 266. The thickness and type of antenna dielectrics 266 along the length of radiating element 262 may be designed to modify and optimize the microwave properties of the antenna 112. For example, one or more antenna dielectrics 266 covering radiating element 262 may be used to shape the microwave field and to optimize the performance of antenna 112. The one or more antenna dielectrics 266 covering radiating element 262 may be used to shape the microwave field by changing the local dielectric environment in the region adjacent to radiating element 262. Examples of dielectric materials that can be used to design one or more embodiments disclosed herein include, but are not limited to EPTFE, PTFE, FEP and other floropolymers, Silicone, Air, PEEK, polyimides, cyanoacrylates, epoxies, natural or artificial rubbers and combinations thereof. In one embodiment, entire radiating element 262 is covered with a silicone dielectric. The layer of silicone used to coat a distal portion of radiating element 262 may be thinner than the layer of silicone used to coat a proximal portion of radiating element 262. The thinner silicone dielectric may be used to compensate for the lower field strength that normally exists at the distal portion of a microwave antenna. Thus, the microwave field is made more uniform along the length of radiating element 262.

In any of the embodiments herein, the shape of radiating element 262 may be that same or different from the shape of shaping element 264. Further in any of the embodiments herein, both radiating element 262 and shaping element 264 may be non-linear. Further, in any of the embodiments herein, radiating element 262 and shaping element 264 may be non-parallel to each other.

FIG. 1A shows a side view of an embodiment of a linear microwave antenna of the present invention having a microwave antenna comprising a radiating element and a microwave field shaping element. In the embodiment shown in FIG. 1A, the novel microwave field shaping technique of the present invention is used to improve the performance of a helical antenna. The resultant antenna can be used to create a uniform lesion along the length of the antenna without adversely affecting tissues surrounding the transmission line. In the embodiment shown in FIG. 1A, the width of antenna 112 is substantially the same as the width of the coaxial cable 250.

In one embodiment, a single microwave signal is fed to antenna 112 through coaxial cable 250. Antenna 112 generates a microwave field. The near field of the microwave field generated by antenna 112 may be used for achieving the desired clinical outcome such as ablating tissue. In FIG. 1A, antenna 112 comprises a radiating element 262 and a shaping element 264. In one embodiment, radiating element 262 is a continuation of the inner conductor 258 of coaxial cable 250. Shaping element 264 shapes the microwave field emitted by radiating element 262. In one embodiment, shaping element 264 is made of an electrically conductive material e.g. a metal or a conductive polymer and is electrically connected to a region of outer conductor 256 of coaxial cable 250. In an alternate embodiment, a conductive shaping element 264 is electrically isolated from outer conductor 256. In this embodiment, shaping element 264 functions as a passive radiator or parasitic element of antenna 112. Shaping element 264 in this electrically isolated embodiment absorbs microwaves radiated from radiating element 262 and re-radiates microwaves.

It should be noted that there is no direct electrical conduction between radiating element 262 and shaping element 264. When microwave energy is delivered through coaxial cable 250 to antenna 112 in FIG. 1A, a first microwave field is emitted by radiating element 262. This first microwave field is a normal mode microwave field of a small diameter (antenna diameter D is much less than the microwave wavelength) helical antenna. The first microwave field interacts with shaping element 264. This interaction induces a leakage current on shaping element 264. The leakage current in turn creates a second microwave field. The second microwave field is an elongated, axial mode microwave field due to the elongate shape of shaping element 264. The first microwave field and the second microwave field together combine to produce a unique shaped microwave field of antenna 112 that is clinically more useful that the unshaped microwave field generated by an antenna 112 comprising only radiating element 262. Thus the original microwave field is redistributed by the design of shaping element 264. Shaping element 264 alone is not capable of functioning as an antenna; rather shaping element 264 shapes or redistributes the electromagnetic or microwave field emitted by radiating element 262 to produce a clinically improved microwave field. It should be noted that there is no direct electrical conduction between radiating element 262 and shaping element 264 in FIG. 1A.

Further, the specific design of shaping element 264 may be used to improve the power deposition of an antenna 112 comprising radiating element 262. Shaping element 264 may be made of one or more non-insulated or insulated conducting materials e.g. metals, conductive polymers, materials with embedded conductive particles, etc. The embodiments of the present invention may be designed wherein individual elements e.g. radiating element 262 have minimal or no sharp corners to avoid undesirable regions of concentrated microwave field.

Antenna 112 in FIG. 1A has a linear, elongate shape that is especially suited for the ablation of a linear region of tissue e.g. for the creation of a linear lesion in the left atrium.

In FIG. 1A, the surface of radiating element 262 is enclosed within one or more layers of dielectric materials. In this embodiment, every portion of radiating element 262 is covered with some dielectric material such that no metallic surface of radiating element 262 is exposed to tissue. Thus, in this embodiment, radiating element 262 is electrically insulated from tissue. Thus, in this embodiment, radiating element 262 is able to transmit a microwave field into tissue, but unable to conduct electricity to tissue. Thus, in this embodiment, there is no electrical conduction and no conductive path between radiating element 262 and shaping element 264. Further, in this embodiment, there is no electrical conduction and no conductive path between radiating element 262 and the surrounding tissue. In one embodiment, the dielectric on a proximal portion of radiating element 262 is a continuation of the dielectric 260 of coaxial cable 250. The thickness of a dielectric on radiating element 262 may vary along the length of radiating element 262. Further, the crossection of a dielectric on radiating element 262 may not be radially symmetric.

In the embodiment of FIG. 1A, radiating element 262 is made of a helically arranged length of a metallic conductor. The helix may be symmetric with a constant pitch and a constant diameter along the length of the helix. In one embodiment, the straightened length of the conductor used for constructing radiating element 262 is about three quarters of the effective wavelength at 915 MHz. In alternate embodiments, this length may be an odd multiple of one quarter of the effective wavelength at one of: 433 MHz ISM band, 915 MHz ISM band, 2.45 GHz ISM band and 5.8 GHz ISM band. Although in FIG. 1A, radiating element 262 has about 19 turns, embodiments of ablation devices 110 may be constructed wherein radiating element 262 has about 1 to 30 turns. The pitch of a helical radiating element 262 may range between 0.3 mm and 20 mm. Radiating element 262 may be made from a metallic element or alloy selected from the group comprising Nitinol, stainless steel or copper. Radiating element 262 may comprise a plating of a conducting metal such as Ag or Au on the outer surface of radiating element 262. The metallic conductor used for constructing radiating element 262 may have a round, oval, rectangular or square crossection.

In one embodiment, the metallic conductor used for constructing radiating element 262 has a round crossection with a diameter of 0.5 mm+/−0.4 mm. In another embodiment, the metallic conductor used for constructing radiating element 262 has a rectangular crossection with crossectional dimensions of 10 mm+/−9.5 mm by 0.5 mm+/−0.4 mm. In another embodiment of a radiating element with a rectangular crossection, the crossectional dimensions are 1 mm+/−0.3 mm by 0.1 mm+/−0.05 mm. In an alternate embodiment, radiating element 262 is made of a length of a metallic conductor that is arranged in a substantially two dimensional configuration. For example, the length of a metallic conductor may be arranged in a substantially wavy or zigzag or serpentine configuration.

In the embodiment in FIG. 1A, radiating element 262 is arranged symmetrically around shaping element 264 and partially or fully encloses shaping element 264. Shaping element 264 may be made of a linear or helical length of a metallic conductor. The outer diameter of shaping element 264 may be uniform or may be non-uniform along the length of antenna 112. In the embodiment shown in FIG. 1A, shaping element 264 is made of a substantially linear length of a metallic conductor. Shaping element 264 may be made from a metallic element or alloy selected from the group comprising Nitinol, stainless steel or copper. Shaping element 264 may comprise a plating of a conducting metal such as Ag or Au on the outer surface of shaping element 264. The metallic conductor used for constructing shaping element 264 may have a round, oval, rectangular or square crossection. In one embodiment, the metallic conductor used for constructing shaping element 264 has a round crossection with a diameter of 0.5 mm+/−0.3 mm. In another embodiment, the metallic conductor used for constructing shaping element 264 has a rectangular crossection with dimensions of 0.5 mm+/−0.3 mm by 0.5 mm+/−0.3 mm. Antenna 112 further comprises one or more antenna dielectrics 266 between radiating element 262 and shaping element 264. In one embodiment, antenna dielectric 266 is sufficiently flexible to create a flexible antenna 112. The flexibility of antenna 112 allows antenna 112 to bend from a substantially linear configuration to a substantially non-linear configuration and vice-versa during clinical use. The flexibility of antenna 112 also allows antenna 112 to bend relative to the distal end of the transmission line during clinical use. This in turn allows a user to introduce antenna 112 to the target location through tortuous or non-linear introduction paths such as blood vessels. In one embodiment, antenna dielectric 266 is sufficiently stiff to create a sufficiently stiff antenna 112.

The stiffness of antenna 112 prevents antenna 112 from bending during clinical use. This in turn enables the user to use antenna 112 to puncture or penetrate through tissue such as tumor tissue. Examples of dielectrics that can be used between radiating element 262 and shaping element 264 include, but are not limited to EPTFE, PTFE, FEP and other floropolymers, Silicone, Air, PEEK, polyimides, natural or artificial rubbers and combinations thereof. Additionally the entire antenna 112 may be covered or encapsulated in a dielectric. Examples of dielectrics that can be used to cover or encapsulate antenna 112 include, but are not limited to EPTFE, PTFE, FEP and other floropolymers, Silicone, PEEK, polyimides, natural or artificial rubbers and combinations thereof. Antenna dielectric 266 may comprise one or more layers of such dielectrics. The dielectric used to cover or encapsulate antenna 112 may be porous or non-porous. In FIG. 1A, the length of antenna 112 is between 10 mm and 80 mm. In FIG. 1A, the width of antenna 112 is between 1 mm and 40 mm. In one particular embodiment, antenna 112 has a length of 45 mm+/−7 mm and a width of 2 mm+/−0.5 mm. Radiating element 262 is electrically connected to inner conductor 258 of coaxial cable 250. This may be done for example, by soldering or resistance welding radiating element 262 to inner conductor 258. Shaping element 264 is electrically connected to outer conductor 256 of coaxial cable 250. This may be done for example, by soldering or resistance welding shaping element 264 to outer conductor 256. Antenna 112 may be floppy, flexible or substantially rigid. Antenna 112 may be malleable or have shape memory or elastic or super-elastic properties. The distal end of antenna 112 may be atraumatic. Antenna 112 may be designed such that the length of antenna 112 is adjustable. For example, length of antenna 112 may be increased or reduced to increase or reduce the length of an ablation zone. In this embodiment, shaping element 264 may have a helical or substantially wavy or zigzag or serpentine configuration. The length of antenna 112 may be increased or reduced intra-operatively or pre-operatively. In one embodiment, one or both of radiating element 262 and shaping element 264 are a part of a flexible circuit and are manufactured using commonly known techniques for manufacturing flexible circuits.

In FIG. 1A, the shape of radiating element 262 is different from the shape of shaping element 264. Further in the embodiment in FIG. 1A, radiating element 262 is non-linear. Further in the embodiment in FIG. 1A, shaping element 264 is substantially linear. However radiating element 262 and shaping element 264 are generally oriented such that their axes are parallel to each other. Alternate embodiments of antenna 112 may be designed wherein radiating element 262 is substantially linear. Alternate embodiments of antenna 112 may be designed wherein shaping element 264 is substantially non-linear. Alternate embodiments of antenna 112 may be designed wherein radiating element 262 and shaping element 264 are generally oriented such that their axes are not parallel.

Although in the embodiment in FIG. 1A shaping element 264 is connected to the distal end of coaxial cable 250, other embodiments of antenna 112 may be designed wherein shaping element 264 is connected to coaxial cable 250 at a region other than the distal end of coaxial cable 250. For example, in one alternate embodiment, shaping element 264 is metallic and is electrically connected to a region of outer conductor 256 of coaxial cable 250 proximal to the distal end of the coaxial cable 250.

In FIG. 1A, since radiating element 262 is in electrical contact with inner conductor 258, there is a first electrically conductive path extending from inner conductor 258 till the distal end of radiating element 262. In the embodiments wherein shaping element 264 is made of a conductive material and is electrically connected to outer conductor 256 of coaxial cable 250, there is a second electrically conductive path extending from outer conductor 256 till the distal end of shaping element 264. In such embodiments, even though there are two conductive paths that extend from first zone Z1 to the second zone Z2, the designs, materials and the microwave properties of the two conductive paths may be significantly different in first zone Z1 and second zone Z2 as described before. In first zone Z1, outer conductor 256 of coaxial cable 250 is located symmetrically around inner conductor 258 and at a constant distance from inner conductor 258. However, in second zone Z2, radiating element 262 is located symmetrically around shaping element 264 and at a constant distance from shaping element 264. In first zone Z1, outer conductor 256 of coaxial cable 250 always acts as a shield for the microwave field in first zone Z1 whereas in second zone Z2, shaping element 264 may or may not act as a shield for the microwave field in second zone Z2.

FIG. 1C shows a section through an embodiment of coaxial cable 250 usable for ablation device 110 of FIG. 1A, 1B and for other ablation devices 110 disclosed herein. In one embodiment, coaxial cable 250 used herein is flexible and comprises an inner conductor 258 made of Nitinol with a Ni content of 56%+/−5%. The outer diameter of inner conductor 258 is 0.0172"+/−0.004". Inner conductor 258 has a cladding or plating 270 of a highly conductive metal such as Ag or Au. In one embodiment, inner conductor 258 comprises a silver cladding 270 of thickness 0.000250"+/−0.000050". Cladding 270 in turn is surrounded by dielectric material 260. In one embodiment, dielectric material 260 is made of expanded PTFE with an outer diameter of 0.046"+/−0.005". The dielectric material 260 in turn is surrounded by the outer conductor 256. Outer conductor 256 acts as a shielding element to the microwave signals transmitted by inner conductor 258. Further, outer conductor 256 shields the microwave signals transmitted by inner conductor 258 from external noise. In one embodiment, outer conductor 256 comprises multiple strands of Ag plated Cu. The multiple strands of outer conductor 256 are arranged such that the outer diameter of outer conductor 256 is 0.057"+/−0.005". Outer conductor 256 in turn is covered by an outer jacket 268. In one embodiment, outer jacket 268 is made of PTFE with an outer diameter of 0.065"+/−0.005". Thus, the outer diameter of coaxial cable 250 is less than about 2 mm. The low profile of flexible coaxial cable 250 has tremendous clinical advantages since it can be inserted through narrow and/or tortuous anatomical paths or introducing device lumens. In one embodiment, a shaft comprising coaxial cable 250 is stiffened or strengthened by adding one or more stiffening or strengthening elements such as enclosing stiffening devices jackets, braids, or stiffening layers over coaxial cable 250. In one embodiment, antenna 112 is stiffened or strengthened by adding one or more stiffening or strengthening elements such as jackets, braids or layers within or over antenna 112.

FIG. 1D shows a longitudinal section of the embodiment of ablation device 110 of FIG. 1A through the distal end of coaxial cable 250. In FIG. 1D, the identity of coaxial cable 250 ends at the distal end of outer conductor 256. Transition line 254 in FIG. 1D is located at the distal end of outer conductor 256 and is substantially perpendicular to the axis of coaxial cable 250 at the distal end of outer conductor 256. Outer jacket 268 of coaxial cable 250 terminates a small distance proximal to the distal end of outer conductor 256. A conductive element attached to the distal end of inner conductor 258 forms radiating element 262. In one embodiment, the proximal end of radiating element 262 is electrically connected to the distal end of inner conductor 258. In one embodiment, the proximal end of radiating element 262 is soldered to inner conductor 258. In another embodiment, the proximal end of radiating element 262 is laser welded to inner conductor 258. The proximal end of radiating element 262 may be electrically connected to inner conductor 258 in various configurations including, but not limited to lap joint and butt joint. The proximal end of shaping element 264 is electrically connected to a region of outer conductor 256. In one embodiment, the proximal end of shaping element 264 is electrically connected to the distal end of outer conductor 256. In one embodiment, the proximal end of shaping element 264 is soldered to outer conductor 256. In another embodiment, the proximal end of shaping element 264 is laser welded to outer conductor 256. The proximal end of shaping element 264 may be electrically connected to outer conductor 256 in various configurations including, but not limited to lap joint and butt joint.

FIG. 1B shows a side view of an embodiment of a microwave antenna comprising one or more electrophysiological mapping or pacing or RF ablation electrodes. Antenna 112 in FIG. 1B is similar in design to antenna 112 of FIG. 1A. Antenna 112 in FIG. 1B has a proximal end connected to the distal end of the transmission line 250, a distal end and an antenna axis. However, antenna 112 in FIG. 1B further comprises one or more electrodes 118. Electrode 118 may be used for one or more of: sensing and/or measuring electrophysiological signals, electrically pacing a tissue and ablating an anatomical region. In the embodiment wherein antenna 112 is used to treat or ablate tissue, electrode 118 may be used for one or more of: identifying the site of treatment, confirming successful treatment and monitoring progress of the treatment. In one method embodiment, ablation device 110 introduced percutaneously into the heart and is used to ablate cardiac tissue to treat an arrhythmia such as atrial fibrillation, flutter, ventricular tachycardia, etc. In such methods, electrodes 118 are used for one or more of: identifying the site of the arrhythmia, identifying site(s) to be ablated, confirming successful ablation of the cardiac tissue, confirming uni-directional or bi-directional block and monitoring progress of the ablation. Thus electrodes 118 confer a clinical advantage to the physician since ablation and sensing can be done by a single slim and flexible device.

Electrodes 118 are made of a metallic material and are exposed to the surrounding tissue. In FIG. 1B, electrode 118 is located in the microwave field generated by antenna 112. Electrode 118 is connected by an elongate conductive wire 276 that electrically connects electrode 118 to an external circuit. Wire 276 is located in the microwave field generated by antenna 112. If improperly placed, both electrode 118 and wire 276 can cause unwanted coupling with the microwave field which in turn can cause unwanted distortion of the microwave field. FIG. 1B shows one embodiment of conductive wire 276 that are designed to cause minimal or no interference with the microwave energy emitted by antenna 112. In FIG. 1B, electrode wire 276 is arranged in a helical configuration around shaping element 264. This novel arrangement or conductive wire 276 reduces the coupling between the conductive wire 276 and the microwave field which in turn reduces the heating of conductive wire 276. Conductive wire 276 may be made of one or more conductive materials. Examples of such materials include, but are not limited to: stainless steel (with or without a coating of copper or gold or silver), copper, gold, silver and alloys thereof and other conductive materials. The diameter of the conductive wire 276 helix in FIG. 1B is substantially uniform along the length of antenna 112. Further, the pitch (distance between adjacent turns) is substantially similar to the pitch of radiating element 262. Further, the axis of the conductive wire 276 helix in FIG. 1B is oriented substantially parallel to the axis of antenna 112. In one embodiment, the diameter of the helical arrangement of conductive wire 276 is less than the diameter of radiating element 262.

In an alternate embodiment, conductive wire 276 is substantially straight and is arranged non-parallel to the length of antenna 112. In one embodiment, the axis of helically disposed conductive wire 276 is substantially parallel to the axis of one or both of: radiating element 262 and shaping elements 264. In FIG. 1B, if conductive wire 276 is defined as a series of curved segments, all of the curved segments are oriented such that they are non-parallel to the axis of antenna 112. The portion of wire 276 located on antenna 112 has about 9 turns. In alternate embodiments, the portion of wire 276 located on antenna 112 has about 0.5 to 30 turns. In another embodiment, coupling between the microwave field and conductive wire 276 is reduced by spacing conductive wire 276 from radiating element 262 by a sufficient amount of a dielectric material. In one embodiment, coupling between the microwave field and conductive wire 276 is used to purposely modify the shape and/or the size of the microwave field. In one embodiment, one or more conductive wires 276 pass along the proximal end of antenna 112.

In one such embodiment, one or more conductive wires 276 are routed over and along coaxial cable 250 i.e. proximally from antenna 112. In another embodiment, one or more conductive wires 276 pass along the distal end of antenna 112. In one such embodiment, one or more conductive wires 276 are routed distally from antenna 112 through a distal dielectric 278 as shown in FIG. 1B. Distal dielectric 278 is located on the distal end of ablation device 110. In one embodiment, one or more conductive wires 276 are embedded in distal dielectric 278. Distal dielectric 278 may or may not form a part of a pull wire or tether 114 arrangement located on the distal region of ablation device 110 as shown in FIGS. 1AA and 1AB. In one embodiment, conductive wires 276 themselves are designed to be tethers 114 or pull wires. In another embodiment, a separate flexible tether 114 is attached to the distal region of ablation device 110 and conductive wires 276 are arranged along tether 114 such that there is no or minimal tension on conductive wires 276 during clinical use.

Electrode 118 is designed to be as small as possible. In one embodiment, electrode 118 is made of a metallic cylindrical ring with an outer diameter between 0.5-5 mm and a length between 0.1-4 mm. In one embodiment, coupling between the microwave field and electrode 118 is reduced by placing electrode 118 in a region of antenna 112 where the microwave field is relatively weak. In another embodiment, coupling between the microwave field and electrode 118 is reduced by spacing electrode 118 from radiating element 262 by a sufficient amount of a dielectric material. Although only a single electrode 118 is shown in FIG. 1B for clarity, embodiments of ablation device 110 may be designed that comprise more than one electrode 118. In one embodiment, an antenna 112 comprising multiple electrodes 118 is designed such that even though individual electrodes 118 may interact with and slightly distort the microwave field, the combined effect of multiple electrodes 118 causes minimal or no net microwave field distortion.

FIGS. 1E-1G show the method steps of a method of creating two overlapping lesions in a tissue. In FIGS. 1E-1G, the method is demonstrated in an experimental setup for demonstrating the utility of antenna 112 of FIG. 1A for intra-cardiac ablation and other applications. The experimental setup comprised a slice of porcine muscle tissue is kept in a water bath maintained at 37 C. Further, water is pumped in the water bath from a nozzle 272 and is continuously circulated through the water bath using a pump (not shown). This is to simulate the effect of blood flow within the heart chambers. In FIG. 1E, a linear antenna 112 similar in design to antenna 112 of FIG. 1A is placed in contact with the porcine tissue as shown. Thereafter, microwave power at 0.915 GHz is delivered to ablation device 110 at 80 W for 60 s.

FIG. 1E shows a first ablation created around antenna 112. In FIG. 1F, antenna 112 is moved to a new location. Thereafter, microwave power is delivered to ablation device 110 at 80 W for 60 s to create a second lesion as shown in FIG. 1G. In FIG. 1G, antenna 112 is being moved away after creating the second lesion. The tissue shows two overlapping lesions that overlap lengthwise. Various patterns of multiple lesions may thus be created by repositioning any of the antennas 112 disclosed herein. Any of the antennas 112 disclosed herein may be repositioned by one or more of: rotating around an axis, moving proximally or distally, moving sideways, revolving around an axis, increasing or reducing in size, engaging a steering or deflecting mechanism on ablation device 110 and engaging a steering or deflecting mechanism on an accessory device. Further, any of the antennas 112 disclosed herein may be designed and used such that during clinical use the forces exerted by a flexible antenna 112 on surrounding tissues do not distort the surrounding tissue. In one embodiment, two lesions are created that do not intersect each other. In another embodiment, two elongate lesions are created that are joined lengthwise. In another embodiment, two elongate lesions are created that are joined breadthwise. In another embodiment, two elongate lesions are created that intersect each other to form an approximately X-shaped resulting lesion.

The lesions created in FIG. 1G were deep and overlapping lesions. The length of the combined lesion was about 9 cm and the visual depth of the lesion varied from 1-1.5 cm. Thus, long, deep lesions may be created by antenna 112. The lesions may be created such that they span the entire thickness of the tissue such as a heart wall. Thus antenna 112 can be used to create trans-mural lesions. Further, there is a complete absence of charring in the lesion. Also, long, deep lesions were created even in the presence of flowing fluid. Thus antenna 112 may be used to create lesions in anatomical regions that contain flowing blood such as the vasculature (veins, arteries, etc.) and the heart chambers.

FIG. 1H shows a side view of an embodiment of a microwave antenna comprising multiple electrophysiological mapping or pacing electrodes that are spaced in regular intervals along the length of antenna 112. Embodiments of ablation device 110 may be designed that comprise 1-64 such electrodes 118. Electrodes 118 may be spaced at regular intervals or at non-regular intervals along the length of antenna 112. In any of the embodiments of electrodes 118 disclosed herein wherein electrodes 118 are electrophysiological mapping electrodes; one or more electrodes 118 may be used in a uni-polar mode or a bi-polar mode. When such electrodes 118 are used in a bi-polar mode, any two electrodes 118 (e.g. two adjacent electrodes 118) may be used for performing a mapping procedure. For example, in FIG. 1H, electrodes 118 may be used in the bi-polar mode by using first and second electrodes 118, second and third electrodes 118, third and fourth electrodes 118, etc. In one embodiment, an antenna 112 comprising multiple electrodes 118 such as shown in FIG. 1H is designed such that even though individual electrodes 118 may interact with and slightly distort the microwave field, the combined effect of multiple electrodes 118 causes minimal or no net microwave field distortion.

FIG. 1I shows a side view of an embodiment of a microwave antenna comprising multiple electrophysiological mapping or pacing electrodes that are spaced in pairs along the length of antenna 112. Such an embodiment is especially suited for cardiac ablation using antenna 112 wherein electrodes 118 are used for electrophysiological mapping in a bi-polar mode. In such an embodiment, two electrodes 118 in a pair are used in a bi-polar mode for performing an electrophysiological mapping procedure. In FIGS. 1H and 1I, conductive wires 276 are not shown for improved clarity.

Although in several figures, elements 118 are described as electrophysiological mapping electrodes 118, one or more of electrodes 118 in any of the embodiments shown herein (such as those shown in FIGS. 1B, 1H, 1I, 1K, 1S, 1T, etc.) may be one or more diagnostic or therapeutic modalities including, but not limited to: radiofrequency ablation electrodes, electrophysiological pacing electrodes, electrophysiological mapping electrodes, temperature sensors, impedance sensors, pressure sensors, proximity sensors, flow sensors, moisture sensors, electromagnetic field sensors, etc. Such diagnostic or therapeutic modalities may comprise one or more metallic or conductive portions. In any of the devices disclosed herein comprising multiple such diagnostic or therapeutic modalities, all of the modalities may perform the same function. In any of the devices disclosed herein comprising multiple such diagnostic or therapeutic modalities, at least two modalities may perform different functions. For example, one modality may be an electrophysiological mapping electrode while another modality may be a temperature sensor. Such elements and the conductive wires 276 connected to such elements may be designed to have minimal or no coupling with the microwave field. Such elements and conductive wires 276 connected to such elements may be exposed to surrounding tissue or may be electrically insulated from surrounding tissue.

FIG. 1J shows a side view of a functional microwave antenna with a design similar to the design shown in FIG. 1A. Antenna 112 in FIG. 1J does not have any electrodes 118. FIG. 1K shows a side view of a functional microwave antenna having additional electrodes 118. The basic design of antenna 112 in FIG. 1K is similar to the basic design of the antenna 112 of FIG. 1J. It can be seen that the lengths of antenna 112 in FIGS. 1J and 1K are similar (about 3.5 cm). Antenna 112 in FIG. 1K comprises three pairs of electrodes 118 (a proximal pair, a middle pair and a distal pair) arranged similar to the arrangement shown in FIG. 1I. The conductive wires 276 of electrodes 118 are routed through a tether 114 connected to the distal end of antenna 112. The conductive wires 276 in FIG. 1K are arranged in a helical configuration on antenna 112 as shown in FIG. 1B. FIGS. 1L and 1M show surface images of lesions obtained by ablating the surface of porcine muscle tissue using the antennas shown in FIGS. 1J and 1K respectively. The initial temperature of the porcine muscle tissue was 37 C to simulate human body temperature. The ablation power used was 80 W and the ablation time was 80 s in both the studies in FIGS. 1L and 1M. FIGS. 1L and 1M show that the surface characteristics of the lesions are substantially similar. The length of both the lesions is about 3.8 cm. The width of both the lesions is about 7-10 mm. FIGS. 1N and 1O show sections of the porcine tissue in FIGS. 1L and 1M showing the depth of the lesions obtained by the antennas in FIGS. 1J and 1K respectively. The maximum depth of both the lesions is about 7-8 mm. This further proves that the novel positioning of electrodes 118 and/or the novel positioning of conductive wires 276 causes minimal or no interference with the microwave field emitted by antenna 112. Further, the unique arrangement of electrodes 118 and wires 276 causes a clinically insignificant distortion of the thermal profile of the heat generated by antenna 112. Further, there are no regions of charring or burning of tissue along the lesion created in FIGS. 1M and 1O. Thus, the novel placement of electrodes 118 and conductive wires 276 has not resulted in any "hot spots" or undesired zones of high temperature.

Non-interfering designs of electrodes 118 and conductive wires 276 will be further illustrated in FIGS. 1P-1R. FIG. 1P shows a side view of a simulated SAR profile generated by an antenna similar to the antenna of FIG. 1A. FIG. 1Q shows a side view of a simulated SAR profile generated by a first antenna similar to the antenna of FIG. 1A but having four extra electrodes 118 spaced at regular intervals along the length of the antenna. The conductive wires 276 in this embodiment are arranged in a non-interfering arrangement as shown in FIG. 1B.

FIG. 1Q demonstrates that the SAR profile generated by the device embodiment having four electrodes 118 is similar to the SAR profile in FIG. 1P. Thus, the unique arrangement of electrodes 118 and wires 276 causes a clinically insignificant distortion of the microwave field generated by antenna 112. Further, the unique arrangement of electrodes 118 and wires 276 causes a clinically insignificant distortion of the thermal profile of the heat generated by antenna 112. In this simulation, four conductive wires 276 were combined into a bundle of wires. Thus, the unique arrangement of conductive wires 276 causes an insignificant distortion of the microwave field generated by antenna 112. The SAR profiles in FIGS. 1Q and 1P are substantially radially symmetric. Further, the SAR profiles in FIGS. 1Q and 1P are substantially bilaterally symmetric on both sides of an imaginary plane oriented perpendicularly to the axis of antenna 112 and passing roughly through the center of antenna 112. FIG. 1Q demonstrates that the microwave field generated by antenna 112 is substantially restricted to second zone Z2. There is a clinically insignificant amount of the microwave field in first zone Z1 containing coaxial cable 250. Thus, there is negligible backward coupling between the microwave field and the distal portion of coaxial cable 250. This in turn reduces the risk of ablating tissue proximal to the distal end of coaxial cable 250. Further, the microwave field is substantially uniform along the length of antenna 112 as compared to a comparable monopole antenna. Thus the lesion formed by the microwave field in FIG. 1Q will be uniform and substantially localized. Thus, embodiments of linear antenna 112 comprising one or more electrodes 118 and their corresponding conductive wires 276 designed to operate at 915 MHz and other microwave frequencies may be designed that can create uniform, symmetrical, continuous, linear lesions with a lesion length greater than 35 mm. Further, FIG. 1Q shows the absence of undesired concentration of microwave energy over the electrodes 118 or over conductive wires 276. This in turn ensures that there will be no "hot spots" or undesired zones of high temperature along antenna 112 during clinical use.

FIG. 1R shows a side view of a simulated SAR profile generated by a second antenna similar to the antenna of FIG. 1A having four extra electrodes 118 spaced at regular intervals along the length of the antenna. The conductive wires 276 in this embodiment are linear and arranged parallel to the axis of antenna 112. FIG. 1R demonstrates that the SAR profile generated by the device embodiment having four electrodes 118 is significantly different from the SAR profile in FIG. 1P. Thus, this arrangement of electrodes 118 and wires 276 has caused a clinically significant distortion of the microwave field and the thermal profile of the heat generated by antenna 112. The microwave field is concentrated in a smaller zone located near the proximal end of antenna 112. In this simulation, four conductive wires 276 were combined into a bundle of wires. The SAR profile in FIG. 1R is not bilaterally symmetric on both sides of an imaginary plane oriented perpendicularly to antenna 112 and passing roughly through the center of antenna 112. Further, the microwave field is substantially non-uniform along the length of antenna 112. Thus the lesion formed by the microwave field in FIG. 1R will be smaller than the lesion in FIG. 1Q. A comparison of the SAR profiles in FIGS. 1Q and 1R illustrate the usefulness of this unique arrangement of electrodes 118 and wires 276.

FIG. 1S shows a view of the distal region of the ablation device similar to the ablation device used in FIGS. 1K, 1M and 1O. In FIG. 1S, ablation device 110 comprises an antenna 112 similar in design to antenna 112 of FIG. 1A. Antenna 112 further comprises three pairs of electrodes 118—a proximal pair, a middle pair and a distal pair. In one embodiment, the proximal pair of electrodes 118 is located away from the junction region of antenna 112 and coaxial cable 250. In one embodiment, the distal pair of electrodes 118 is located near or on the distal end of antenna 112. A flexible coaxial cable 250 supplies power to antenna 112. The distal end of antenna 112 is connected to a tether 114 comprising a transparent distal dielectric 278 made at least partially of silicone and conductive wires 276. Such an ablation device 110 may be used in any suitable method and device embodiments disclosed herein including, but not limited to the embodiments shown in FIGS. 1AA-1AK, 2A-2D, 4A-4B, 6H-6Q and 7E-7H. It can be seen in FIG. 1S that the tether 114 is continuous with the remainder of ablation device 110. Further, the tether is connected to the distal end of antenna 112.

Electrodes 118 and wires 276 may or may not be physically located on the device that comprises antenna 112. For example, electrodes 118 and wires 276 may be located on a separate device that is located around antenna 112. FIG. 1T shows an antenna similar to the antenna in FIG. 1A being slidably introduced through the lumen of a functional tube. In FIG. 1T, functional tube 188 comprises four equally spaced electrodes 118. Each electrode 118 is connected to a conductive wire 276. The four conductive wires 276 are arranged on functional tube 188 such that every curved segment of the conductive wires 276 is non-parallel to the axis of the functional tube 188. When antenna 112 is located within functional tube 188 such that antenna 112 is enclosed within electrodes 118, both electrodes 118 and a portion of conductive wires 276 are exposed to the microwave field generated by antenna 112. However, as discussed elsewhere in the specification, the novel arrangement of electrodes 118 and conductive wires 276 will not adversely affect the safety and efficacy of a procedure performed using antenna 112. During a method, the relative positions of antenna 112 and functional tube 188 may be changed by a user. In one embodiment, functional tube 188 comprises a steering or deflecting mechanism. The embodiment in FIG. 1T differs from the embodiment in FIG. 1B. In FIG. 1B, electrodes 118 and wire 276 are attached to antenna 112 or embedded inside antenna dielectric 266 of antenna 112. In FIG. 1T, electrodes 118 and wire 276 are slidable relative to antenna 112 and are not fixed to antenna 112.

Non-interfering designs of electrodes 118 and conductive wires 276 will be further illustrated in FIGS. 1U-1W. FIG. 1U shows a side view of a simulated SAR profile generated by a 915 MHz monopole antenna. FIG. 1V shows a side view of a simulated SAR profile generated by a monopole antenna similar to the antenna of FIG. 1U but having four extra electrodes spaced at regular intervals along the length of the antenna. The conductive wires 276 in this embodiment are arranged in a non-interfering arrangement as shown in FIG. 1B. FIG. 1V demonstrates that the SAR profile generated by this device embodiment having four electrodes 118 is similar to the SAR profile in FIG. 1U. Thus, the unique arrangement of electrodes 118 and wires 276 causes a clinically insignificant distortion of the microwave field generated by antenna 112.

Further, the unique arrangement of electrodes 118 and wires 276 causes a clinically insignificant distortion of the thermal profile of the heat generated by antenna 112. In this simulation, four conductive wires 276 were combined into a bundle of wires. The SAR profiles in FIGS. 1V and 1U are substantially radially symmetric. Further, the SAR profiles in FIGS. 1V and 1U are substantially bilaterally symmetric on both sides of an imaginary plane oriented perpendicularly to antenna 112 and passing roughly through the proximal end of antenna 112. FIG. 1W shows a side view of a simulated SAR profile generated by a monopole antenna similar to the antenna of FIG. 1U but having four extra electrodes spaced at regular intervals along the length of the antenna wherein each electrode is connected to a conductive wire. The conductive wires 276 in this embodiment are linear and arranged parallel to the axis of antenna 112. FIG. 1W demonstrates that the SAR profile generated by the device embodiment having four electrodes 118 is significantly different from the SAR profile in FIG. 1U. Thus, this arrangement of electrodes 118 and wires 276 has caused a clinically significant distortion of the microwave field generated by antenna 112. The microwave field is concentrated in a smaller zone located near the proximal end of antenna 112. In this simulation, four conductive wires 276 were combined into a bundle of wires. The SAR profile in FIG. 1W is not bilaterally symmetric on both sides of an imaginary plane oriented perpendicularly to antenna 112 and passing roughly through the proximal end of antenna 112. Thus the lesion formed by the microwave field in FIG. 1W will be smaller than the lesion in FIG. 1V. A comparison of the SAR profiles in FIGS. 1W and 1V illustrate the usefulness of this unique arrangement of electrodes 118 and wires 276.

Further, the unique arrangement of electrodes 118 and wires 276 does not negatively affect the simulated return loss of a device with a monopole antenna. A simulated return loss of −14.90 was obtained at 915 MHz for a device with a monopole antenna of FIG. 1U. A simulated return loss of −19.52 was obtained at 915 MHz for a device with a monopole antenna and electrodes and electrode wire arrangement of FIG. 1V. This is actually a significant improvement over the return loss of the device of FIG. 1U. A simulated higher return loss of −12.86 was obtained at 915 MHz for a device with a monopole antenna and electrodes and electrode wire arrangement of FIG. 1W. Thus, the electrode and electrode wire arrangement of FIG. 1W has negatively affected the simulated return loss of a device with a monopole antenna.

In a first variation, the invention includes a medical system 100 for performing a medical procedure on or in a patient, the medical system 100 comprising at least a first hollow sheath or arm 102. In the specification, the term "arm" is used to describe any elongate device that can be used to introduce and/or manipulate one or more components of medical system 100. Thus, arm can be an introducing catheter, a cannula, a tubular sheath, etc. Arm 102 has a maneuverable distal portion 104 and a proximal portion 106, wherein manipulation of proximal portion 106 of arm 102 permits articulation of maneuverable distal portion 104 of arm 102. A medical component 110 is mechanically coupled to arm 102 and is adjustably extendable from maneuverable distal portion 104 of arm 102. Medical component 110 is mechanically engaged to maneuverable distal portion 104 of arm 102, such that movement of maneuverable distal portion 104 alters the position and/or the orientation of medical component 110.

FIG. 1AA shows an embodiment of a medical system 100 comprising a sheath or arm 102 that is used to introduce and position a medical component 110. In FIG. 1AA, medical component 110 comprises a working element 112 (e.g. a flexible long antenna) located on a first portion of medical component 110 and a tether 114 that forms the second portion of medical component 110. In this embodiment, the first portion is integrated with the second portion. The first portion comprises a device shaft 116 that may be twisted or torqued by the user. Device shaft 116 is slidably and rotatably positioned within a lumen of arm 102. Device shaft 116 may comprise a first circuit that transmits energy to the distal region of medical component 110. In one embodiment, working element 112 is a flexible long microwave antenna and the device shaft comprises a coaxial cable that transmits microwave energy (e.g. at 915 MHz ISM band or at 2.45 GHz ISM band) to working element 112.

Examples of microwave ablation antennas that can be used in the present invention are given in U.S. Provisional Patent Application Ser. No. 61/162,241 filed on Mar. 20, 2009 titled "Methods and devices for applying energy to bodily tissues", and in U.S. Provisional Patent Application Ser. No. 61/222,409 filed on Jul. 1, 2009 titled "Steerable medical systems for positioning medical elements in or within a body"; the entire disclosures of which are incorporated herein by reference. In FIG. 1AA, medical component 110 forms a mechanically unsupported looped region beyond the distal end of arm 102. The region of medical component 110 proximal to the distal end of arm 102 is mechanically supported by arm 102. The size and/or the shape and/or the position and/or the orientation of the looped region is adjustable by one or more user directed movements. The first portion of medical component 110 comprises four pairs of mapping electrodes 118. One or more mapping electrodes 118 may be located on one or more of the following locations: adjacent to an end of working element 112, spaced apart from working element 112 and over the extent of working element 112.

In the embodiment shown in FIG. 1AA, two pairs of mapping electrodes 118 are located adjacent to each end of working element 112. Also in the embodiment shown in FIG. 1AA, two pairs of mapping electrodes 118 are located over the extent of working element 112 and surround working element 112. Mapping electrodes 118 may be used to obtain electrophysiological signals from tissue. Embodiments of medical component 110 comprising mapping electrodes 118 located in close proximity to or over working element 112, enables the user to perform both electrophysiological mapping by one or more mapping electrodes 118 and energy delivery by working element 112 without changing the position of working element 112. Thus in several method embodiments disclosed herein, working element 112 is positioned at a first location of a target tissue. Thereafter, working element 112 is used to deliver energy to the first location of the target tissue to ablate tissue and create a first lesion. One or more mapping electrodes 118 are used to map electrophysiological signals from the ablated tissue or other tissue at the first location of the target tissue while maintaining working element 112 at the first location of the target tissue. Thus, mapping electrodes 118 may be used to confirm desired ablation of tissue and/or to determine the need for additional energy delivery to tissue. When mapping electrodes 118 are present over working element 112, the user can perform both energy delivery as well as mapping without moving working element 112 and without needing an additional device for mapping. This greatly simplifies the procedure while eliminating the cost of an additional device for mapping.

Tether 114 is slidably positioned within a lumen of arm 102. In one embodiment of medical system 100 in FIG. 1AA, tether 114 has a sufficient stiffness to be pushable and/or torqueable. Tether 114 may be connected to a portion of device shaft 116 or to a working element 112. Any of the tethers 114 disclosed herein may comprise one or more working elements 112 or mapping electrodes 118. Tether 114 and other steering mechanisms disclosed herein may be used to change the shape of a flexible working element 112. For example, the shape of working element 112 may be changed from one of: a linear shape, a planar non-linear shape and a non-planar non-linear shape (three dimensional) shape to one of: a linear shape, a planar non-linear shape and a non-planar non-linear shape (three dimensional) shape and vice versa.

Working element 112 may be used to create ablations that are similar or dissimilar to the shape of the working element 112. For example, a working element 112 in a substantially circular configuration may be used to create a substantially circular lesion. Alternately, a working element 112 in a substantially circular configuration may be used to create a substantially round lesion. The round lesion may be created, for example, by using a higher power setting and/or higher time setting than that used for creating the substantially circular lesion. Similarly, working elements 112 in a substantially closed loop configuration may be used to create lesions that correspond to the shape of the perimeter of the substantially closed loop configuration or to the shape of the area enclosed by the substantially closed loop configuration. Thus, a linear working element 112 may be used to create one or more of: linear lesions, area ablations (e.g. by positioning linear working element 112 at multiple regions on a tissue surface or by using a bent working element 112 to create an area ablation) or volume ablations e.g. by creating deeper lesions over several regions on a target tissue.

In any of the embodiments herein, the stiffness of the region of tether 114 distal to the distal end of arm 102 may be the same as or more than or less than the stiffness of the region of shaft 116 distal to the distal end of arm 102.

In one embodiment of the device in FIG. 1AA, mapping electrodes 118 and a second circuit electrically connected to mapping electrodes 118 are placed on working element 112 such that there is minimal interference from mapping electrodes 118 with a microwave field generated by working element 112. In one embodiment, the second circuit comprises electrode wires made of copper or gold or silver or of stainless steel with or without a plating of copper/gold/or/silver. The electrode wires may be located on device shaft 116 or on tether 114. In one embodiment, the electrode wires are electrically insulated from the first circuit and working element 112. Mapping electrodes 118 may be made of standard radiopaque materials such as platinum. Thus, the user may use radiographic visualization to visualize mapping electrodes 118 or other radiopaque components of the devices disclosed herein during a procedure.

One or more mapping electrodes 118 may be substituted by one or more radiofrequency ablation electrodes or electrophysiological pacing electrodes that deliver controlled electrical energy for electrophysiological pacing of tissue such as cardiac tissue. Although in FIG. 1AA, mapping electrodes 118 are shown only on device shaft 116, one or more mapping electrodes 118 may be present on one or more of: device shaft 116 and tether 114. In one method embodiment, working element 112 and one or more mapping electrodes 118 are simultaneously used for delivering microwave energy and for electrophysiological mapping of tissue respectively. In another method embodiment, one or more mapping electrodes 118 are used for electrophysiological mapping of tissue after working element 112 has delivered microwave energy. In another method embodiment, one or more mapping electrodes 118 are used for electrophysiological mapping of tissue before working element 112 has delivered microwave energy.

In FIG. 1AA, the distal end of tether 114 is connected to a distal end of device shaft 116. The connection is an end-to-end connection. In such a connection, there is a smooth transition between the curve of the distal end of tether 114 and the curve of the distal end of device shaft 116. In such embodiments, when one of: shaft 116 and tether 114 is advanced distally by an amount and the other of: shaft 116 and tether 114 is withdrawn proximally by a substantially similar amount, the position of working element 112 on the looped region of medical component 110 is changed without substantially changing the shape of the looped region. In such embodiments, the stiffness of the region of tether 114 distal to the distal end of arm 102 may be substantially similar to the stiffness of the region of shaft 116 distal to the distal end of arm 102.

In FIG. 1AA, arm 102 comprises an opening at the distal end of arm 102 through which medical component 110 exits. In alternate embodiments, arm 102 comprises one or more openings that are located on a side wall of arm 102 rather than at the distal end of arm 102. The one or more openings may be of the same size and shape or differ in size and/or shape. The one or more openings may be arranged on arm 102 such that medical component 110 exits arm 102 at an angle to arm 102.

FIG. 1AB shows an embodiment of a working model of the medical system 100 similar to that shown in FIG. 1AA. In FIG. 1AB, the medical component 110 comprises a first portion that comprises a microwave antenna 112. Microwave antenna 112 is supplied with microwave energy through a flexible coaxial cable that forms a shaft 116 of the first portion of medical component 110. Tether 114 forms the second portion of medical component 110. Antenna 112 and a portion of the coaxial cable are covered with a layer of dielectric material 120 such that antenna 112 is electrically insulated from the surrounding tissue. Arm 102 herein comprises three pull wires to deflect the distal portion 104 of arm 102 in three planes. However, medical component 110 in FIG. 1AB does not contain mapping electrodes 118.

Although many variations of medical system 100 are discussed and/or illustrated with a single arm 102, variations of medical system 100 may include any number of arms 102. In some variations, medical component 110 extends through arm 102 in a generally concentric or coaxial manner. However, the invention also includes arrangements of medical component 110 and arm 102 wherein medical component 110 extends parallel to arm 102, or extends along arm 102 or a portion thereof in a non-concentric manner. Arm 102 may be reversibly coupled to one or more medical component(s) 110 via a grasping structure. Examples of such grasping structures include, but are not limited to: releasable hooks, rings, or jaws. Arm 102 may be fully or partially hollow. One or more arms 102 may be arranged concentrically to manipulate medical component 110. Arm 102 may be introduced via one or more access ports and pathways.

For purposes of this specification, the term medical component 110 is intended to describe a medical device or portion thereof that is adapted to provide a visualization, diagnostic, or treatment procedure. For example, and as described below, in one variation, medical system 100 may include a medical component 110 comprising a first portion comprising a working element 112 configured to deliver energy (e.g., radiofrequency (monopolar or bipolar), resistively generated heat, microwaves, ultrasound energy, laser)

to or from tissue and a second portion (such as a guidewire, rail, tether 114, etc.) that is used to manipulate the position and/or the orientation of the first portion. Alternatively, or in combination, medical component 110 may also comprise one or more sensors or information receiving elements. For example, such elements can include one or more of: electrodes (that detect and/or measure voltage, current and/or impedance), temperature sensors, pressure sensors, light measurement devices, infrared sensors, chemical sensors, radiation sensors, deformation sensors, or any other type of sensors that observe and/or measure a state or condition of tissue or the body. In one embodiment, the first portion and the second portion are parts of the same medical component 110. In one embodiment, the first portion and the second portion are integrated with each other and are non-separable without destroying medical component 110. In another embodiment, first portion and second portion are separable from each other by one or more user generated actions. In one embodiment, the first portion can advance over the second portion which functions as a rail, guide, or tether. In such a case, the first portion and second portion may be separate medical devices.

Examples of medical components 110, include, but are not limited to, therapeutic devices such as ablation devices for imparting a treatment to a target tissue, diagnostic devices such as mapping catheters for providing physiological information regarding a target tissue; positioning devices which include elements for providing additional positioning of additional medical components 110 (e.g., guidewires, rails, tethers, introducer catheters, sheaths, etc.), imaging devices, or non-imaging feedback devices (such as a Doppler catheter). Medical component 110 need not have a specific physical structure, for example an arm 102 of the inventive medical system 100 can be adapted to deploy a simple tube that administers a chemical ablating agent at a desired location or delivers an additional fluid used during, and in support of, the medical procedure (e.g. a contrast agent delivered to provide a clearer view of the anatomy in support of a procedure performed within a patient's heart). In yet additional variations, medical system 100 may comprise multiple separate medical components 110 used to provide a single diagnostic procedure or different steps of the same medical procedure. For instance, when using a radiofrequency energy modality, a first medical component 110 could include a first electrode while a second medical component 110 can include a second electrode (either the opposite or same polarity). Alternatively, one medical component 110 can include an ablation element or electrode while a second medical component 110 contains one or more mapping electrodes to assess the ablation lesion created by the first medical component 110.

Any of the arms 102 may comprise a handle portion on the proximal end of arm 102. The handle portion enables the user to control movement of the distal portion 104 of arm 102. In one embodiment, the handle portion is connected to one or more steering control mechanisms e.g. pull wires, pre-shaped tubular sheaths, inflatable balloons, slidable stylets, etc. In one embodiment, the handle mechanism allows the physician to control the maneuverable distal section 104 of arm 102 with a single hand. The movement of distal section 104 of arm 102 can occur in any three dimensional space. In a particular embodiment, arm 102 comprises two pairs of oppositely disposed pull wires. In another embodiment, arm 102 comprises three pull wires arranged 120 degrees apart around the circumference of arm 102. Accordingly, embodiments of arm 102 comprising any number of steering mechanisms or steering control mechanisms are to be considered within the scope of this invention.

In several embodiments of the present invention, a single type of steering mechanism is shown on arm 102. However, the invention is not limited to only a single type of steering mechanism on arm 102. Instead, any of the arms 102 of the present invention may employ any number and/or type of steering mechanisms or controls or actuators to produce the desired steering capability of the arm 102.

Any of the tethers 114 herein may have a circular, semicircular, oval, or a non-uniform cross section. In additional variations, a tether 114 may comprise a hollow cavity with any number of openings for delivery of one or more fluids such as gases or liquids such as contrast agents. In one such embodiment, a tether 114 comprises one or more lumens.

Tether 114 may be made of a metallic or non-metallic (e.g. polymeric) material. In one embodiment, tether 114 comprises a coating (e.g. a lubricious coating) on the outer surface of tether 114. In one embodiment, tether 114 has an insignificant column strength i.e. tether 114 is floppy. In another embodiment, tether 114 is a wire-like member having a sufficient stiffness that allows for improved control of the remaining portion of medical component 110.

Any of the tethers 114 disclosed herein may comprise a steering mechanism to steer or deflect a portion of tether 114. In one such embodiment, a tether 114 comprises a lumen in which a steering device is slidable positioned. The steering mechanism may be one or more of: a sufficiently stiff stylet, a pull wire, a hollow tube and a deflectable elongate device.

In additional embodiments of the medical system 100, the position and/or the orientation of one or more medical components 110 disclosed herein can be locked relative to an arm 102. In one such embodiment, proximal portion 106 of arm 102 comprises a reversibly locking mechanism such as a rotating hemostasis valve. In another such embodiment, a handle 108 of an arm 102 can include such locking mechanisms.

In one embodiment, the position and/or the orientation of one or more arms 102 disclosed herein may be independently frozen in place to permit the physician to independently freeze the position and/or the orientation of each arm 102 into a desired profile or orientation. This reduces or eliminates the need by the physician to continuously hold an arm 102 in any particular profile.

Any of the devices disclosed herein may have a varying degree of flexibility along the length of the device. For example, arm 102 may comprise a relatively stiff proximal portion 106 and relatively flexible distal portion 104. This permits ease of articulation of arm 102 at the treatment site but a relatively stable proximal portion 106 from which arm 102 can be maneuvered.

In additional variations of the system, one or more arms 102 may be configured to perform medical procedures as well. For instance, an arm 102 may comprise one or more electrodes, a fluid source, a suction source, a reservoir to collect tissue, etc. In another embodiment, distal portion 104 of arm 102 may be adapted to provide suction, irrigation, contrast agents, etc. to the target site. In yet another embodiment, distal portion 104 of arm 102 comprises vision capabilities such as a fiber optic, CCD camera, or another vision source enabling visualization of one or more portions of medical system 100 and/or the anatomy during a procedure.

In embodiments wherein medical component 110 is connected to an auxiliary component (e.g., a power supply, imaging monitor, fluid source, etc.), a handle connected to medical component 110 can include the desired connector.

FIGS. 1AC and 1AD show two configurations of an embodiment of a medical system 100 wherein medical component 110 is introduced in the anatomy through arm 102. Medical component 110 comprises a shaft 116 having one or more working elements 112. In one embodiment, working elements 112 are selected from the group consisting of: radiofrequency ablation electrodes, microwave antennas, electrophysiological mapping electrodes, electrophysiological pacing electrodes, ultrasound emitting elements, cryoablative elements, laser emitting elements, electrocautery elements, electrosurgical cutting and/or coagulating elements and combinations thereof. The distal end of shaft 116 is coupled to a string or tether 114. The shape and/or the size and/or the position and/or the orientation of the region of medical component 110 distal to the distal region of arm 102 can be changed by one or more of: torquing arm 102, advancing or withdrawing arm 102, steering a steerable distal region of arm 102, torquing shaft 116 of medical component 110, advancing or withdrawing shaft 116 of medical component 110 and pulling or releasing tether 114. In one embodiment, arm 102 is steerable and is robotically controlled by a user. In this embodiment, the shape and/or the size and/or the position and/or the orientation of the region of medical component 110 distal to the distal region of arm 102 can be further changed by robotically manipulating the distal region of arm 102. In another embodiment, arm 102 is steerable and is further enclosed by a second steerable arm 102 (not shown). In this embodiment arm 102 and second steerable arm 102 are telescopingly coupled together. In this embodiment, the shape and/or the size and/or the position and/or the orientation of the region of medical component 110 distal to the distal region of arm 102 can be further changed by one or more of: changing the relative positions of arms 102 and second arm 102, engaging a steerable distal region of second arm 102 and torquing arm 102 relative to second arm 102.

In FIG. 1AC, medical component 110 is in a "U-mode". In this mode, there is a smooth profile transition from the distal end of first portion of medical component 110 to the distal portion of tether 114. This mode may be created by extending the shaft of medical component 110 by a sufficient distance from the distal region of arm 102 and pulling tether 114. In FIG. 1AD, medical component 110 is in a "V-mode". In this mode, the distal end of first portion of medical component 110 is angled relative to the distal portion of tether 114. This mode may be created by releasing tether 114 sufficiently to enable shaft 116 of medical component 110 to acquire a comparatively linear shape due to the elasticity of shaft 116. In one embodiment, tether 114 is slidingly coupled relative to shaft 116 of medical component 110. For example, tether 114 may slide within a lumen of shaft 116 of medical component 110. In another embodiment, tether 114 is fixed to a portion on shaft 116 of medical component 110.

FIGS. 1AE and 1AF show two configurations of an embodiment of a medical system 100 wherein medical component 110 and second medical component 122 are introduced in the anatomy through arm 102. In FIG. 1AF, medical component 110 and second medical component 122 are introduced into the anatomy in a looped configuration as shown. The distal ends of medical component 110 and second medical component 122 are connected to each other by tether 114. In one embodiment, tether 114 or a portion thereof is flexible enough to assume an acute bend of about 180 degrees when medical component 110 and second medical component 122 are introduced in the anatomy through arm 102. This enables the introduction of medical component 110 and second medical component 122 through arm 102 in a folded configuration or "V-mode" as shown in FIG. 1AE. In one method embodiment, medical component 110 and second medical component 122 are introduced in the anatomy through arm 102 in the configuration shown in FIG. 1AE. Thereafter, one of medical component 110 and second medical component 122 is advanced distally while the other of medical component 110 and second medical component 122 is withdrawn proximally relative to arm 102. This is done such that tether 114 lies inside arm 102. Thereafter, a medical procedure is performed using medical system 100. Thus, the flexible part (e.g. a flexible portion of tether 114) of medical system 100 is used during introduction of medical component 110 and second medical component 122 through arm 102 and is withdrawn from the anatomy when the medical procedure is performed.

Medical component 110 comprises a shaft 116 having one or more working elements 112. Similarly, second medical component 122 comprises a shaft 116 having one or more working elements 112. Working elements 112 on medical component 110 or second medical component 122 may be any of the working elements disclosed elsewhere in this document. The shape and/or the size and/or the position and/or the orientation of the regions of medical component 110 and second medical component 122 distal to the distal region of arm 102 can be changed by one or more of: torquing arm 102, advancing or withdrawing arm 102, steering a steerable distal region of arm 102, torquing the shaft of medical component 110 or second medical component 122, advancing or withdrawing medical component 110 or second medical component 122 relative to arm 102 and engaging a steering modality on medical component 110 or second medical component 122. In one embodiment, arm 102 is steerable and is robotically controlled by a user.

In this embodiment, the shape and/or the size and/or the position and/or the orientation of regions of medical component 110 or second medical component 122 distal to the distal region of arm 102 can be further changed by robotically manipulating the distal region of arm 102. In another embodiment, arm 102 is steerable and is further enclosed by a second steerable arm 102 (not shown). In this embodiment arm 102 and second steerable arm 102 are telescopingly coupled together. In this embodiment, the shape and/or the size and/or the position and/or the orientation of regions of medical component 110 or second medical component 122 distal to the distal region of arm 102 can be further changed by one or more of: changing the relative positions of arm 102 and second steerable arm 102, steering a steerable distal region of second steerable arm 102 and torquing arm 102 relative to second steerable arm 102. In FIG. 1AF, medical component 110 is in a "U-mode". This mode is created by extending the shafts of medical component 110 and second medical component 122 by a sufficient distance from the distal region of arm 102 and doing one of: pressing the distal regions of medical component 110 and second medical component 122 against tissue (as shown) and engaging a steering mechanism on medical component 110 or second medical component 122. In FIG. 1AE, medical component 110 is in a "V-mode". This mode can be created by taking medical system 100 of FIG. 1AF away from the tissue thereby causing the shafts of medical component 110 and second medical component 122 to acquire a comparatively linear shape due to the elasticity of the shafts. Alternatively, the "V-mode" can be created by engaging a steering mechanism on medical component 110 or second medical component 122. In one embodiment, tether 114 is slidingly coupled relative to the shaft of one or both of medical component 110 and second medical component 122. For example, tether 114 may slide within a lumen of one or both of medical component 110 and second medical component 122. In another embodiment, tether 114 is fixedly coupled to the shafts of medical component 110 and second medical component 122.

Any of the medical components 110 disclosed herein may comprise one or more bendable regions to enable the insertion of a folded medical component 110 into the anatomy. FIGS. 1AG-1AK show various steps of a method of introducing a medical component 110 comprising a bendable or foldable region into the anatomy through an arm 102. In FIGS. 1AG-1AK, a portion of arm 102 has been cut out to show the orientation and position of the devices within arm 102. In the embodiment shown, tether 114 comprises a bendable or foldable region 115. In the embodiment shown, region 115 spans a short length of or a point on tether 114. In an alternate embodiment, region 115 is a flexible connection between tether 114 and shaft 116 of medical component 110. In another alternate embodiment, entire tether 114 is flexible enough to be bendable or foldable.

Region 115 is designed such that it can assume an acute bend of about 180 degrees when a folded medical component 110 is introduced in the anatomy through arm 102 as shown in FIG. 1AG. This enables the introduction of medical component 110 through arm 102 in a folded configuration or "V-mode" as shown in FIG. 1AG. In the step shown in FIG. 1AH, medical component 110 is advanced distally through arm 102. Thereafter, in the step shown in FIG. 1AI, medical component 110 is further advanced distally such that region 115 and a portion of working element 112 are positioned distal to the distal end of arm 102. Thereafter, in the step shown in FIG. 1AJ, shaft 116 is advanced distally while tether 114 is withdrawn proximally to position region 115 inside arm 102. Thus, region 115 is used during introduction of medical component 110 through arm 102 and is withdrawn from the anatomy after introducing working element 112 into the anatomy through arm 102. In the configuration shown in FIG. 1AJ, a looped region of medical component 110 comprising a portion of tether 114 and shaft 116 and working element 112 is located in the anatomy. In the embodiment shown in FIG. 1AJ, the looped region of medical component 110 is mechanically unsupported in the anatomy while the region of medical component 110 proximal to the distal end of arm 102 is supported by arm 102. After medical component 110 is deployed as shown in FIG. 1AJ, a medical procedure may be performed using working element 112. In one embodiment, working element may be used to deliver microwave energy to tissue. In one embodiment, the stiffness of the region of shaft 116 distal to the distal end of arm 102 is substantially the same as the stiffness of the region of tether 114 disposed distal to the distal end of arm 102. In this embodiment, if one of: shaft 116 and tether 114 is pulled proximally by an amount and the other of: shaft 116 and tether 114 is advanced distally by the same amount, the position of working element 112 on looped region of medical component is changed without substantially changing the size and/or the shape of the looped region of medical component 110. In FIG. 1AK, working element 112 is repositioned by advancing shaft 116 distally by an amount and pulling tether 114 proximally by the same amount. This changes the position of working element 112 on looped region of medical component without substantially changing the size and/or the shape of the looped region of medical component 110.

In another embodiment, medical component 110 comprises a sufficiently elastic joint between shaft 116 and tether 114. The sufficiently elastic joint allows the joint to bend at an angle of about 180 degrees when folded medical component 110 is introduced through arm 102 as shown in FIG. 1AG. In one embodiment, the sufficiently elastic joint comprises a sleeve of stretchable material such as natural or artificial rubbers or polymers. Such a sleeve may enclose a support element such as a wire.

In another embodiment, a joint between shaft 116 and tether 114 has two configurations—a locked configuration and an unlocked configuration. The unlocked configuration loosely couples shaft 116 and tether 114 such that they can be advanced parallel to each other as shown in FIG. 1AG. After the joint exits the distal end of arm 102, the joint is converted to a locked configuration in which shaft 116 and tether 114 are more tightly coupled together. After performing a procedure, the joint is converted to the unlocked configuration to enable the user to remove shaft 116 and tether 114 from the anatomy using arm 102. In one such embodiment, the joint comprises two complementary fitting parts—one part is attached to tether 114 and the other part is attached to shaft 116. In another such embodiment, the joint is a reversibly detachable ball and socket joint. The ball portion and the socket portion of the joint may be brought closer to each other to achieve the locked configuration. The ball portion and the socket portion of the joint may be moved apart from each other to achieve the unlocked configuration.

FIGS. 2A-2D show various method steps of accessing and/or diagnosing and/or treating one or more regions of the left atrium. In the embodiments shown in FIG. 2A-2D, arm 102 and medical component 110 are inserted through the femoral vein and ultimately advanced into a left atrium of the heart via the inferior vena cava. In such methods, the position and/or the orientation of one or more regions of medical component 110 may be manipulated by one or more of: advancing or withdrawing medical component 110 relative to the distal region of arm 102, torquing shaft 116 of medical component 110, engaging one or more steering mechanisms (e.g. pull wires) on medical component 110, pulling or releasing tether 114, torquing tether 114, advancing or withdrawing arm 102, engaging one or more steering mechanisms (e.g. pull wires) on arm 102, torquing arm 102 and increasing or decreasing the size of a looped portion of medical component 110. One or more of the abovementioned manipulations may be performed simultaneously.

One or more of the method steps disclosed in FIGS. 2A-2D may be performed during a medical procedure. Further, one or more of the method steps disclosed in FIGS. 2A-2D may be performed more than once during a medical procedure. Further, one or more of the method steps disclosed in FIGS. 2A-2D and elsewhere in this document and one or more of the device embodiments disclosed herein may be used to perform one or more of: an electrophysiological ablation procedure, an electrophysiological mapping procedure and an electrophysiological pacing procedure. One or more of the method steps disclosed in FIGS. 2A-2D may be used to treat atrial fibrillation by ablating multiple regions in the left atrium and/or to treat atrial flutter by ablating one or more regions in the right atrium.

The system described herein is capable or reaching every desired target region of the left atrium during ablation procedures for treating atrial fibrillation. Further, if a long microwave antenna is used as a working element 112, the resulting lesion is deep, long and transmural. Thus the present invention is capable of forming deep, long, transmural lesions in any orientation and in any location within the left or right cardiac atria for treating electrophysiological disorders such as atrial fibrillation and flutter. This dramatically reduces the time, cost and complexity of therapeutic procedures for treating electrophysiological disorders while increasing their effectiveness.

The figures in FIG. 2 series show various views of the heart showing the superior vena cava (SVC), inferior vena cava (IVC), the left superior pulmonary vein (LSPV), the left inferior pulmonary vein (LIPV), the right superior pulmonary vein (RSPV), the right inferior pulmonary vein (RIPV), the mitral valve annulus (MVA) and the tricuspid valve annulus (TVA). In FIG. 2A, medical system 100 comprising arm 102 and a looped medical component 110 is introduced through the inferior vena cava (IVC), the right atrium and through a single opening or puncture in the inter-atrial septum into the left atrium. The distal portion of arm 102 has been deflected to enable contact of working element 112 with a region on the left side of the left atrium. A portion of medical component 110 is oriented such that it extends from a region close to the ostium of the left inferior pulmonary vein to the annulus of the mitral valve. Thereafter, a suitable ablative energy e.g. microwave energy may be delivered to create one or more lesions extending from the left inferior pulmonary vein to the annulus of the mitral valve.

Figure 2A:
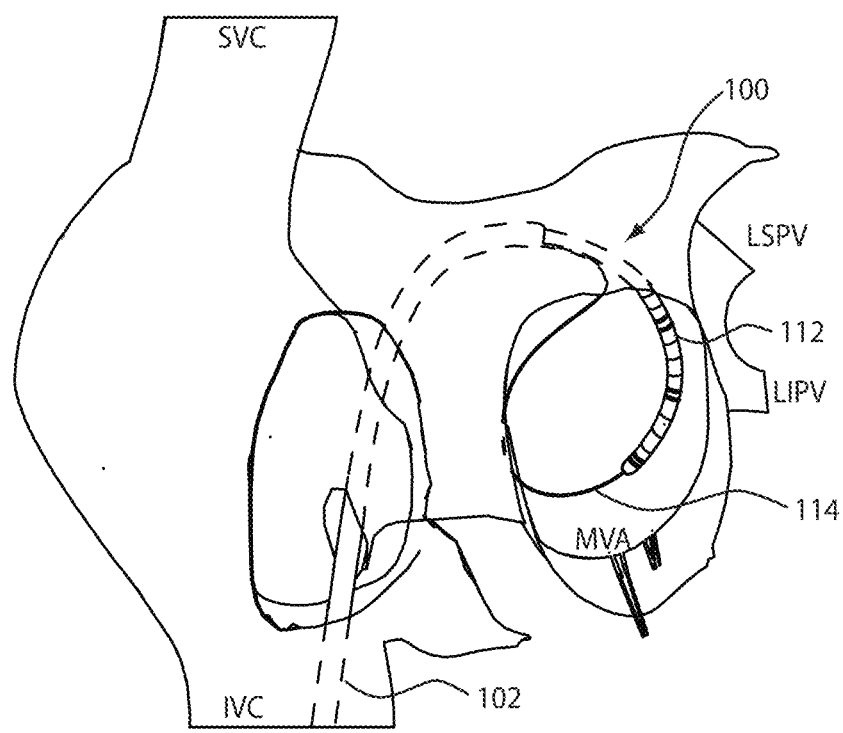
FIGS. 2A-2D show various method steps of accessing and/or diagnosing and/or treating one or more regions of the left atrium.
Figure 2B:
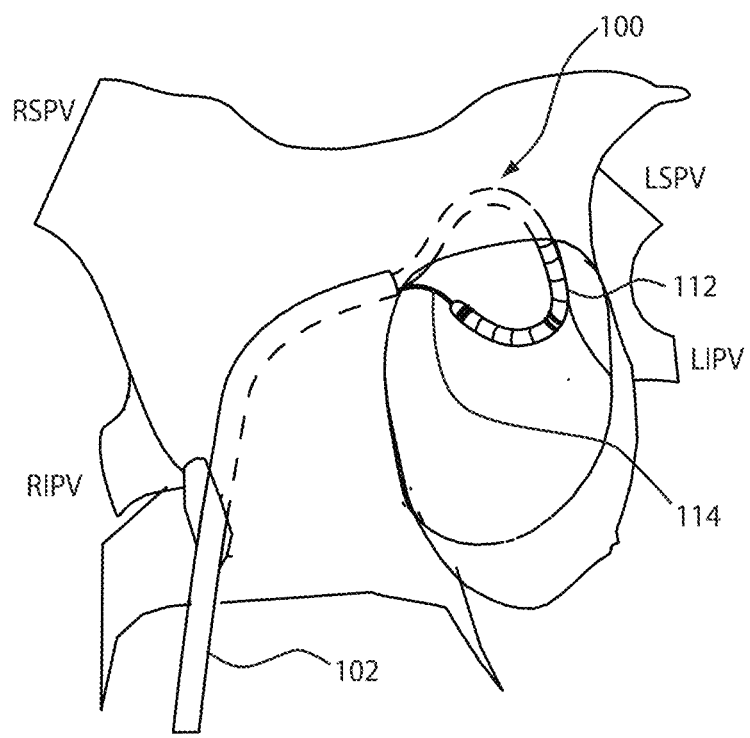
Figure 2C:
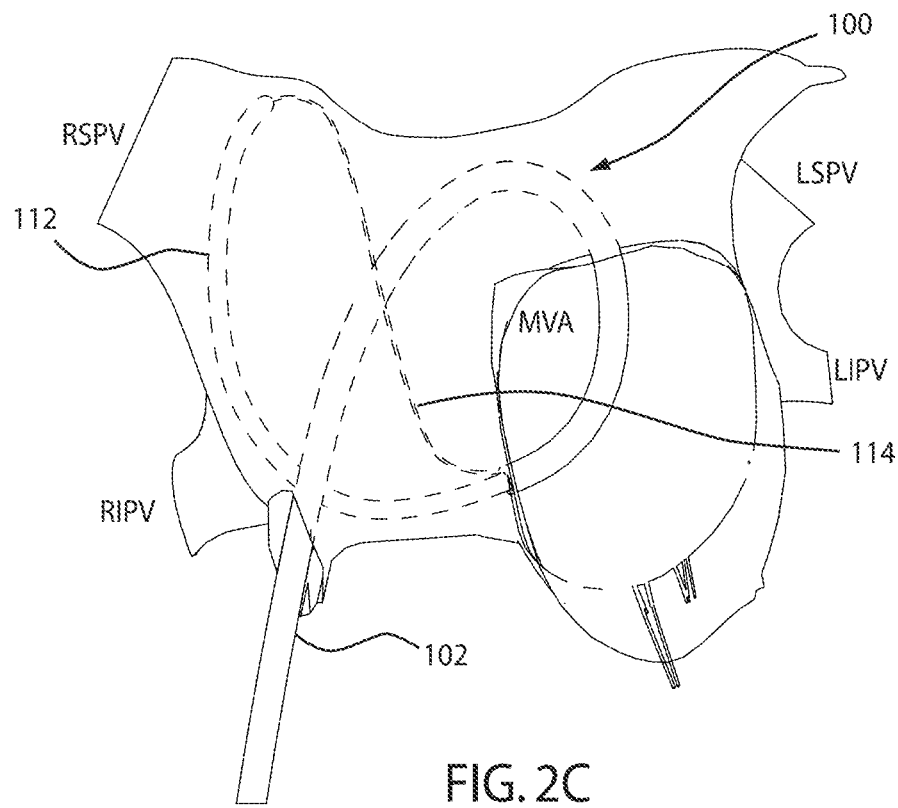
Figure 2D:
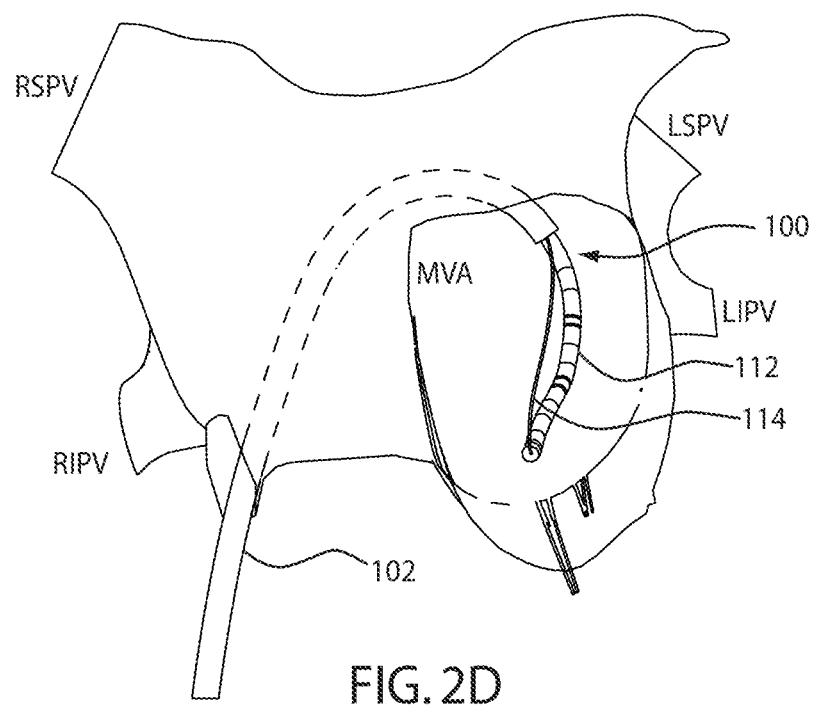
Figure 2E:
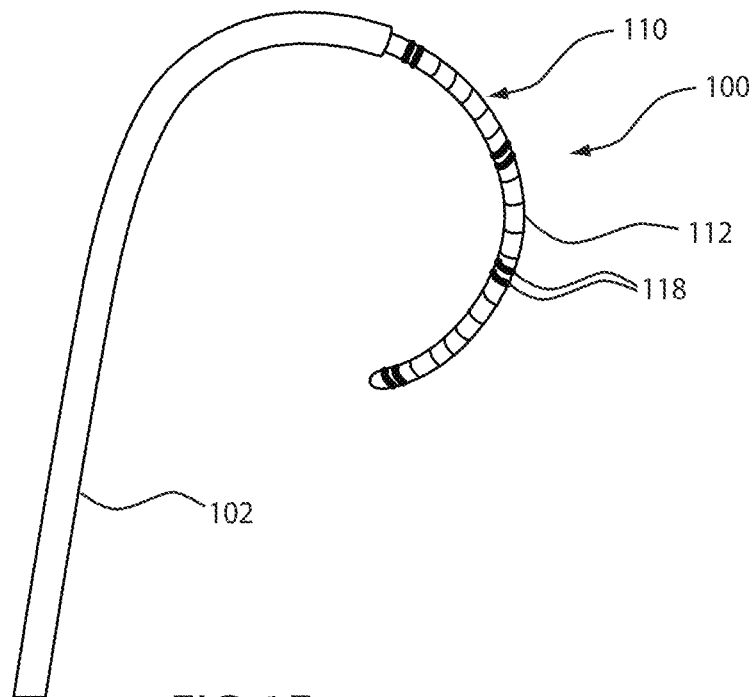
FIG. 2E shows an embodiment of a treatment assembly similar to the treatment assembly in FIG. 1AA.
Figure 2F:
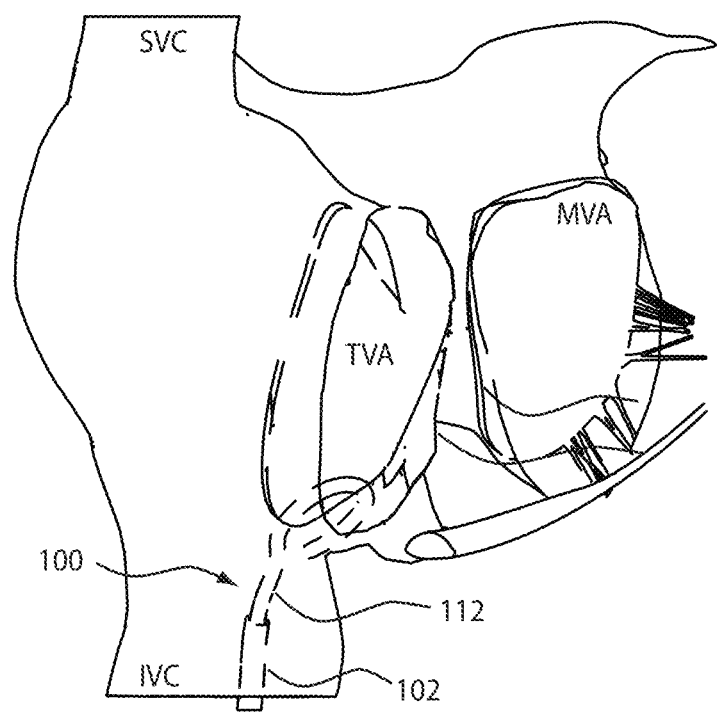
FIG. 2F shows an AP view of the right atrium showing a step of a method of ablating a portion to treat atrial flutter using the treatment assembly in FIG. 2E.

The size of the loop of medical component 110 may be reduced (as shown in FIG. 2B) or increased as desired. Further the deflection on the distal region of arm 102 may also be reduced or increased to position working element 112 at or near the left pulmonary veins (e.g. at or near the left pulmonary vein ridge). Thereafter, a lesion (e.g. an area ablation) on the left pulmonary vein ridge may be created. A small looped medical component 110 may be steered by arm 102 and used to ablate small regions of tissue to fill in any electrophysiological "gaps" (if any) between adjacent ablations. The distal end of arm 102 may be positioned facing the roof of the left atrium. This position of working element(s) 112 is used to create a long "roof line" lesion on the roof of the left atrium. In FIG. 2F, tether 114 is manipulated to further position one or more working elements 112 on the roof of the left atrium. This step may be used to enable working element 112 to conform to any irregular surface of the left atrium. In FIG. 2G, the distal region of arm 102 is deflected by more than 180 degrees. In one embodiment, the distal region of arm 102 is deflected by about 200-280 degrees. This enables the distal end of arm 102 to point towards the right pulmonary vein ostia. In one method embodiment, this orientation of arm 102 wherein the distal end of arm 102 points towards the right pulmonary veins is achieved without torquing arm 102. Thereafter, looped medical component 110 is advanced relative to the distal end of arm 102 to create one or more lesions around the right pulmonary vein ostia. In FIG. 2D, medical component 110 is partially deployed from the distal end of arm 102. This arrangement may be used to create shorter lesions.

Alternate embodiments of medical systems and ablation devices 100 may be designed wherein medical component 110 does not comprise a tether 114. FIG. 2E shows an embodiment of a medical system similar to the medical system in FIG. 1AA. In the embodiment in FIG. 2I, medical component 110 does not comprise a tether 114. However, any of the medical components 110 disclosed herein such as shown in FIG. 2E and FIG. 1AA may comprise one or more steering mechanisms to steer or deflect a distal region of medical component 110. Examples of such steering mechanisms include, but are not limited to one or more: sufficiently stiff stylets, pull wires, hollow tubes and deflectable elongate devices. Such steering mechanisms may be designed such that they cause none or minimal interference with the energy field emitted by elements such as working element 112. In one such embodiment, one or more steering mechanism is made of a non-metallic material. For example, medical component 110 may comprise one or more internal pull wires made of a polymeric material. The embodiment shown in FIG. 2E may be used for accessing and/or diagnosing and/or treating one or more regions of the left atrium and other anatomical regions using methods similar to those described in FIGS. 2A-2D. In such methods, the position and/or the orientation of one or more regions of medical component 110 may be manipulated by one or more of: advancing or withdrawing medical component 110 relative to the distal region of arm 102, torquing a shaft of medical component 110, engaging one or more steering mechanisms (e.g. pull wires) on medical component 110, advancing or withdrawing arm 102, engaging one or more steering mechanisms (e.g. pull wires) on arm 102 and torquing or rotating arm 102. One or more of the abovementioned manipulations may be performed simultaneously. Further, one or more of the abovementioned manipulations may be performed more than once during a medical procedure. Further, one or more of the method steps disclosed in FIGS. 2A-2D and elsewhere in this document and one or more of the device embodiments disclosed herein may be used to perform one or more of: an electrophysiological ablation procedure, an electrophysiological mapping procedure and an electrophysiological pacing procedure.

FIG. 2F shows a view of the right atrium showing a step of a method of ablating a portion to treat atrial flutter using the medical system in FIG. 2E. In FIG. 2F, working element 112 is positioned such that it extends from the annulus of the tricuspid valve till the inferior vena cava. Thereafter, working element 112 is used to ablate an area extending from the annulus of the tricuspid valve till the inferior vena cava. In another embodiment, a substantially linear working element 112 is used to ablate a substantially linear region extending from the annulus of the tricuspid valve till the inferior vena cava.

Method embodiments similar to those shown in FIG. 2F may also be performed using any of the other embodiments of medical system 100 disclosed herein including the medical system 100 of FIG. 1AA.

Any of the medical systems herein such as those shown in FIGS. 1AA and 2E may be used to ablate tissue around the coronary sinus. In one such embodiment, medical component 110 is introduced inside the coronary sinus to ablate tissue. In another embodiment, working element 112 is positioned inside the left atrium and is used to deliver energy such that the ablation extends from the endocardial surface at least till the coronary sinus. In one such embodiment, the ablation may be trans-mural extending from the endocardial surface till the epicardial surface.

Any of the sheaths or arms such as arm 102 may comprise a steering mechanism. Examples of such steering mechanisms include, but are not limited to pull wires, pre-shaped tubular sheaths and stylet structures. A physician may rotate an arm 102 to cause an articulated distal section 104 to move in an arc-type motion. An arm 102 may comprise a single steering member 128 e.g. a pull wire that extends through a wall of arm 102 so that steering member 128 does not interfere with any devices located in a working lumen 130 of arm 102.

In some cases it may be desirable to reposition arm 102 along a three dimensional arc-type path, space, or area without requiring rotation of arm 102. Since rotation of arm 102 might also rotate medical component 110 located therein, the ability to reposition arm 102 without rotation may be useful to avoid or minimize rotation of at least a proximal portion of medical component 110. In one embodiment, the steering arm 102 includes a plurality of steering members 128 arranged symmetrically in a wall of the arm 102. In one such embodiment, three steering member 128 are arranged symmetrically around lumen 130. Such a symmetrical arrangement of three steering members 128 allows the user to deflect distal portion 104 in three planes. Devices according to the present invention can include any number of steering members as desired without adversely impacting the size or flexibility of the arm 102. In the embodiments herein wherein more than two steering members 128 are used, the distal end of arm 102 may be steerable to point in any direction in a three dimensional space without torquing or rotating arm 102.

In one embodiment, two steering member 128 are arranged symmetrically around steering arm 102 on opposite sides of lumen 130. The steering members 128 may be used to deflect distal portion 104 in a single plane. In another embodiment, two steering member 128 are arranged non-symmetrically on steering arm 102. This enables the user to deflect or steer distal portion 104 of arm 102 in two planes.

In one embodiment, three steering member 128 are arranged non-symmetrically around lumen 130. Two of the three steering members 128 are arranged on opposite sides of lumen 130. Such a non-symmetrical arrangement of three steering members 128 allows the use to deflect distal portion 104 in two planes—a first plane enclosed by the oppositely arranged steering members 128 and a second plane different from the first plane.

In one embodiment, the four steering member 128 are arranged symmetrically around lumen 130. Such a symmetrical arrangement of four steering members 128 allows the use to deflect distal portion 104 in two planes—each plane containing two oppositely located steering members 128.

In one embodiment, steering member 128 are arranged such that there are two pairs of steering members 128 and the steering members 128 in each pair are located on opposite sides of lumen 130. Such an arrangement of four steering members 128 allows the user to deflect distal portion 104 in two planes—each plane containing two oppositely located steering members 128.

Thus distal portion 104 of arm 102 can be designed using appropriate number and position of steering members 128 to be steered in only a single direction, along two directions, along three directions or steered along four directions. Distal portion 104 of arm 102 can also be designed using appropriate number and position of steering members 128 to be steered in more than four directions. Distal portion 104 of arm 102 can be designed using appropriate number and position of steering members 128 to be steered along a single plane, along two planes and along three planes. Distal portion 104 of arm 102 can also be designed using appropriate number and position of steering members 128 to be steered in more than three planes.

In one embodiment, steering members 128 are pull wires. In another embodiment, any of the steering members 128 are stylets slidably positioned within arm 102. The stylets have a sufficient stiffness to steer the distal region 104 of arm 102 when advanced or withdrawn relative to arm 102. One or more regions, especially one or more distal regions of the stylets may be pre-shaped. In another embodiment, the stylets can be twisted or torqued by the user to steer the distal regions of arm 102.

Any arm 102 disclosed herein may comprise a handle 108 on the proximal region of arm 102. Handle 108 enables the user to control movement of distal portion 104 of arm 102 by manipulating one or more regions or elements of handle 108. In one embodiment, handle 108 is connected to one or more steering control mechanisms e.g. pull wires, pre-shaped tubular sheaths or stylet structures. A hub may be located on the proximal end of arm 102. The proximal end of a lumen of arm 102 may open at the proximal end of hub. Hub may include one or more side ports. The one or more side ports may be used for example to introduce one or more liquids or devices into the lumen of arm 102.

Any of the arms 102 may comprise longitudinal slots or passages. Each of the longitudinal slots may enclose a pull wire 128 or other steering member. In one embodiment, pull wires 128 are made of stainless steel coated with PTFE. A pull wire enclosure may be disposed around each pull wire 128. Pull wire enclosures may be used to reduce friction during operation of the pull wires 128. Further, pull wire enclosures may be used to prevent the longitudinal slots of arm 102 from collapsing. In one embodiment, a pull wire enclosure is made of a helix or coil of stainless steel coated with PTFE. A lumen of arm 102 may be strengthened by an inner coil. Inner coil may prevent the lumen of arm 102 from collapsing. This in turn reduces the risk of forming a kink or a localized sharp bend in the lumen of arm 102, especially when distal region 104 of arm 102 is bent or deflected by a large angle such as 180 degrees or more. Such a kink or a localized sharp bend may substantially increase the friction between arm 102 and a device such as medical component 110 introduced through the lumen of arm 102. Thus preventing the formation of a kink or a sharp bend enables the smooth movement (e.g. translation, rotation) of devices within the lumen of arm 102 even when distal region 104 of arm 102 is bent or deflected by a large angle. Inner coil may also provide sufficient strength to arm 102 such that arm 102 may be pushed or pulled or torqued when introduced inside the anatomy. In one embodiment, inner coil is made of stainless steel.

Figures 3A, 3B:
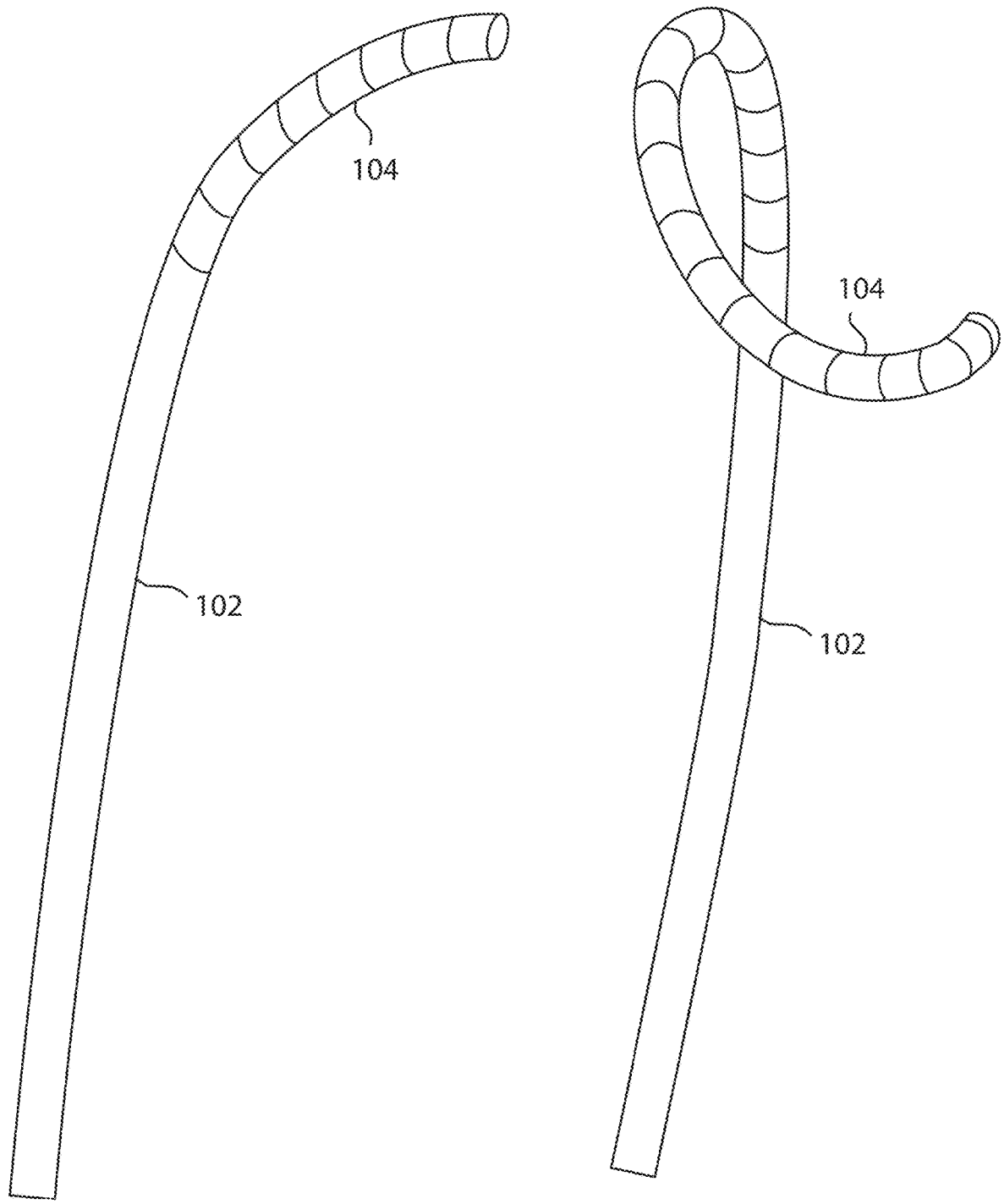
FIGS. 3A-3B show an embodiment of an arm having a distal portion capable of being deflected from a planar configuration as shown in FIG. 3A to a non-planar configuration as shown in FIG. 3B.

FIGS. 3A-3B show an embodiment of an arm 102 having a distal portion 104 capable of being deflected from a planar configuration as shown in FIG. 3A to a non-planar configuration as shown in FIG. 3B. The embodiment of arm 102 shown may comprise one or more steering mechanisms to steer distal portion 104. In FIG. 3A, distal portion of arm 102 has been deflected from a substantially linear profile to a bent profile as shown. This may be achieved by engaging a first steering mechanism (e.g. a pull wire, a stylet, an inflatable balloon, etc.). Distal portion 104 of arm 102 is substantially planar as shown.

In FIG. 3B, distal portion of arm 102 has been deflected from a substantially planar, bent profile to a non-planar profile as shown. This may be achieved by engaging a second steering mechanism (e.g. a pull wire, a stylet, an inflatable balloon, etc.). Thus even if distal portion 104 is deflected by more than 180 degrees, the distal end of arm 102 does not get mechanically obstructed by a region of arm 102. This configuration of arm 102 may be used to carry out any of the method steps disclosed herein. Any of the medical systems 100 disclosed herein may comprise arms 102 that can be converted from a substantially linear configuration to a configuration in which distal portion 104 comprises more than one curve. In one embodiment, a medical system 100 disclosed herein comprises an arm 102 that can be converted from a substantially linear configuration to a configuration in which distal portion 104 is spiral or helical. In the embodiments wherein arm 102 comprises multiple steering mechanisms, one or more steering mechanisms may be different. For example, an arm 102 may be designed using a pull wire and a slidable stylet. In one such embodiment, the distal most portion of the stylet is always located proximal to the distal most portion of the pull wire. In the embodiments wherein arm 102 comprises multiple steering mechanisms, one or more steering mechanisms may be similar or the same. For example, an arm 102 may be designed using two pull wires oriented at varying circumferential positions around arm 102. Any of the pull wires disclosed herein may be oriented substantially parallel to the length of arm 102 spanned by the pull wire. Any of the pull wires may be oriented in a non-parallel orientation relative to the length of arm 102 spanned by the pull wires. Any of the medical systems 100 disclosed herein may comprise one or more bendable arms 102 wherein the radius of bending may be varied by the user.

Any of arms 102 disclosed herein may be pre-shaped. Various combinations of embodiments of arm 102 disclosed herein can be used to create medical systems 100. For example, medical system 100 may be designed with a preshaped arm 102 comprising three steering members 128.

Figure 4A:
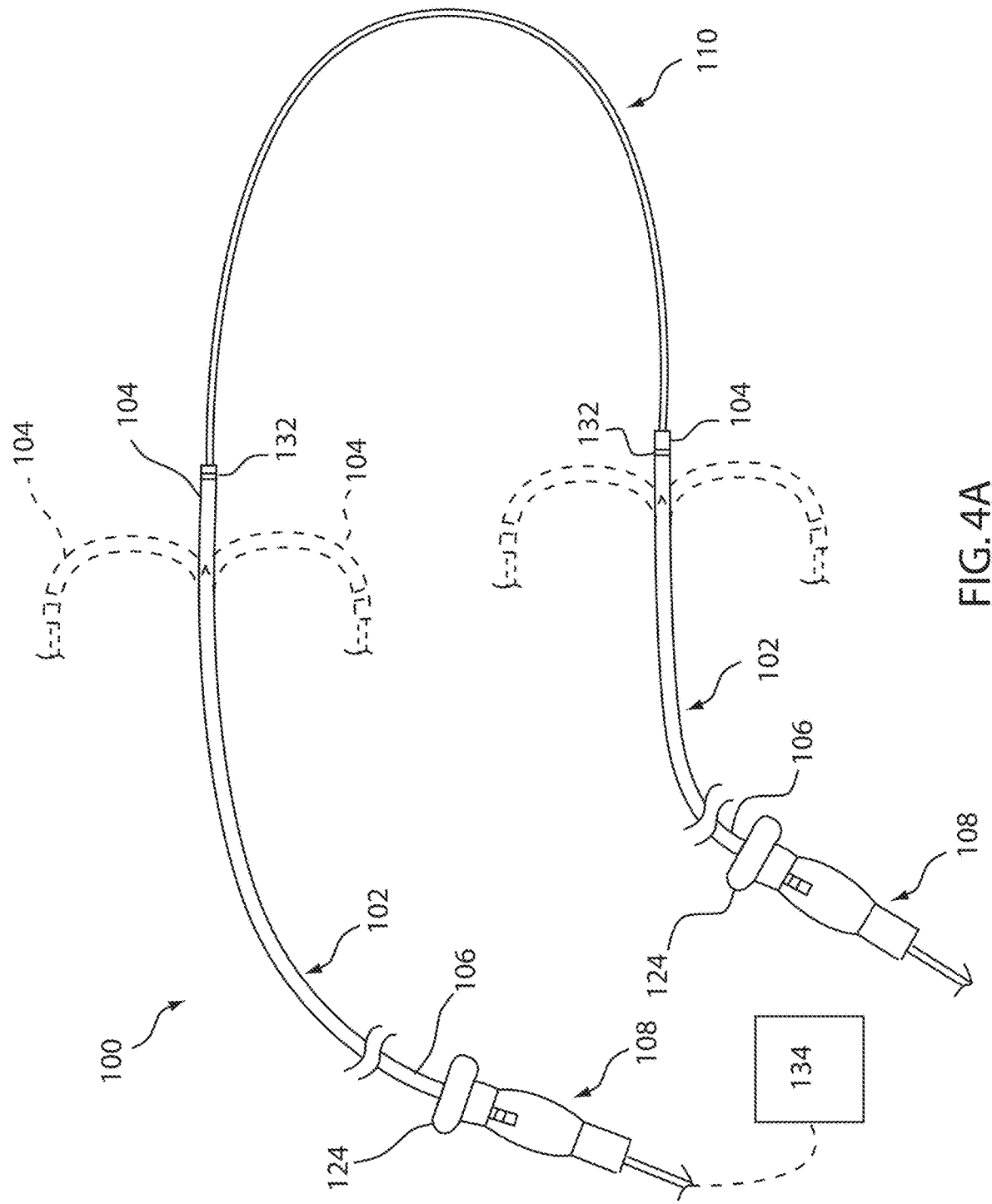
FIG. 4A illustrates a first embodiment of a medical system comprising two arms that allow for improved positioning of one or more medical components extending between the two arms.

FIG. 4A illustrates a first embodiment of a medical system 100 that allows for improved positioning of one or more medical components 110. As shown, the system 100 includes a first maneuverable or steerable arm 102 and second maneuverable or steerable arm 102 that together manipulate medical component 110 extending between the distal end of the two arms. As discussed in detail below, the system 100 can be equipped to position any number of medical components. In most cases, at least one medical component 110 extends between first arm 102 and second arm 102. In one embodiment, first maneuverable or steerable arm 102 can be non-movably coupled to the medical component 110. In such a case, the combination of the first permanently mounted steerable arm 102 and medical component 110 would itself become a first maneuverable or steerable medical device. Medical component 110 may comprise one or more working elements.

Examples of such working elements are disclosed elsewhere in this document. Medical component 110 could also be passive with no working elements. Examples of medical component 110 with at least one working element include, but are not limited to steerable or non-steerable ablation catheters using ablative energies such as radiofrequency, microwave, ultrasound, cryoablative modalities or laser; electrocautery devices and electrosurgical cutting and/or coagulating devices. The working element may not have an electrical component. For example, medical component 110 may comprise a mechanical working element. Examples of such mechanical working elements include, but are not limited to forceps, needle drivers, scissors, graspers, retractors, hooks, obturators, hollow devices such as cannulas and delivery devices for delivering other devices, implants (e.g. artificial valves, occlusion devices, etc.), chemicals, drugs, biological material (stem cells, proteins, hormones, organs, tissues, etc.), etc. Examples of medical component 110 with no working element include, but are not limited to solid or hollow wires and hollow tubes made of polymeric and/or metallic materials.

Arms 102 as shown in FIG. 4A comprise radiopaque markers 132 located on distal portions 104 of arms 102. Radiopaque markers 132 and/or other radiopaque components of the devices disclosed herein enable a user to track the location and/or the orientation of distal portions 104 of arms 102 under fluoroscopic visualization. Such radiopaque markers 132 may be located on any device disclosed herein. Alternately, any of the devices disclosed herein may comprise one or more regions of increased or decreased radio-opacity. Such regions of increased or decreased radio-opacity enable the user to accurately determine the location and/or the position and/or the extent of such regions under fluoroscopic visualization. Portions of increased radio-opacity may be created by additions of metallic segments or embedded contrast material into the devices disclosed herein. In one embodiment, at least two portions of medical component 110 or additional devices placed using medical component 110 deployed beyond distal portions 104 of arms 102 have differing radio-opacity. The differing radio-opacity may be used for example, to determine the position and/or the orientation of one or more working elements located on such devices.

Both the first and the second maneuverable or steerable arms 102 could be non-movably coupled to the medical component 110. In such a case, the combination of the first and second permanently mounted steerable arms 102 and medical component 110 would itself become a first maneuverable or steerable medical device. Medical component 110 could also include working elements as described earlier in this paragraph, or include no working element and be passive.

In any of the embodiments of medical systems 100 comprising multiple arms 102 disclosed herein, two or more of the multiple arms 102 may be similar. In one embodiment, all of the multiple arms 102 of a medical system 100 comprising multiple arms 102 are similar in design. In another embodiment, none of the multiple arms 102 of a medical system 100 comprising multiple arms 102 are similar in design.

Arms 102 are shown to be substantially parallel to each other in FIG. 4A. In alternate embodiments of medical system 100, arms 102 may not be substantially parallel to each other. Arms 102 may be introduced into an anatomical region by similar or same paths. For example, arms 102 may both be introduced into the left atrium of the heart from the right femoral vein. In another embodiment, arms 102 may be introduced into an anatomical region by different paths. For example, first arm 102 may be introduced into the left atrium of the heart from the right femoral vein while second arm 102 may be introduced into the left atrium of the heart from the left femoral vein. In another embodiment, first arm 102 may be introduced into the left atrium of the heart from a subclavian vein while second arm 102 may be introduced into the left atrium of the heart from a femoral vein.

Figure 8B:
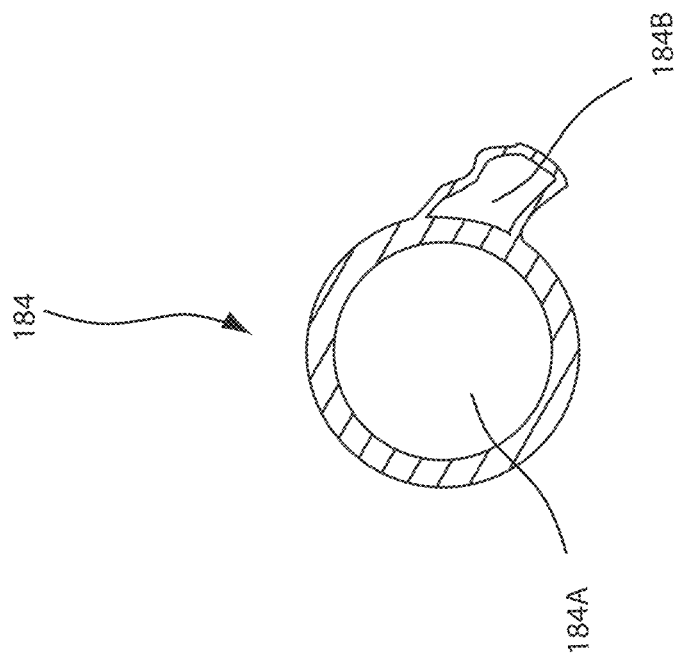
FIGS. 8A and 8B show two embodiments of arm coupling elements 184 that may be used to mechanically couple two or more arms disclosed herein.
Figure 8A:
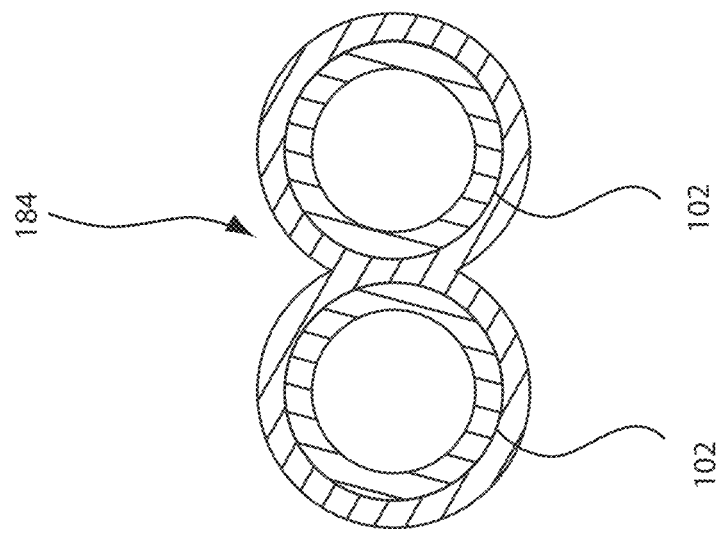

Arms 102 may be coupled to each other. For example, arms 102 may be introduced into the anatomy through a common sheath. In one embodiment, arms 102 are introduced into the anatomy through a single lumen of a sheath. In another embodiment, arms 102 are introduced into the anatomy through two different lumens of a sheath. In another embodiment, a coupling member such as an arm coupling element 184 may be used to couple arms 102 together as shown in FIG. 8A. Arm coupling element 184 may be made of a soft collapsible material. FIG. 8B shows an embodiment of an arm coupling element 184 comprising two lumens. One of the lumens is collapsible as shown, while the other lumen is substantially non-collapsible.

In those embodiments wherein medical component 110 requires connection to an auxiliary component (e.g., a power supply, imaging monitor, fluid source, etc.), medical component 110 can extend through handle 108 of either arm 102 for connection to a respective auxiliary unit 134. In some embodiments, handle 108 can include the desired connector.

One or more regions of medical component 110 can be positioned at a desired location and orientation by performing one or more of the following actions: advancing or withdrawing one or both arms 102, torquing one or both arms 102, deflecting or maneuvering or steering the distal portions 104 of arms 102; and advancing or withdrawing medical component 110 relative to the distal portions 104 of arms 102. After the one or more regions of medical component 110 are positioned at the desired location and orientation, a diagnostic or treatment procedure is performed. The diagnostic or treatment procedure can be performed by medical component 110 itself or by an additional device that is placed using medical component 110. After the diagnostic or treatment procedure is performed, one or more regions of medical component 110 can be repositioned at a second desired location and orientation. Thereafter, a diagnostic or treatment procedure is performed. This sequence can be repeated as needed. Any of the medical components 110 disclosed herein may be used to perform a series of diagnostic and/or therapeutic procedures. In one embodiment, the series of diagnostic and/or therapeutic procedures comprise similar diagnostic and/or therapeutic procedures. For example, medical component 110 can be used to perform a series of therapeutic ablation procedures. In another embodiment, at least two procedures of the series of diagnostic and/or therapeutic procedures are different. For example, medical component 110 can be used to perform a combination of diagnostic electrophysiological sensing or mapping procedures and therapeutic ablation procedures.

In additional embodiments, any of the medical components 110 disclosed herein may be used to provide a path for a second medical component (not shown) that performs the medical procedure. For example, variations can include the first medical component 110 comprising a rail or guide-wire type of device. Once the physician positions the rail guidewire, the physician can then advance a second treatment or therapeutic component along the rail guidewire to perform a diagnostic or treatment procedure. In an alternate variation, the second treatment component can be a catheter with a working element (where such working element can comprise an electrode for mapping and/or ablation, a sensor, or other active portion).

In yet an additional variation, the medical component 110 can comprise a hollow sheath or rail, where a medical treatment component can be slidably located therethrough. For example, the medical treatment component can consist of an energy transfer device that delivers energy through the sheath or rail (or an opening located therein) to perform the surgical procedure. Various embodiments of medical system 100 may be configured as delivery systems for delivering a user-selected device using medical system 100. For example, the combination of arms 102 and a hollow medical component 110 may be used to form a delivery system capable of accurately delivering a standard elongate device (e.g. diagnostic catheters, ablation catheters, imaging catheters, etc.) into the anatomy through hollow medical component 110.

Various combinations of embodiments of arms 102 disclosed herein can be used to create medical systems 100 such as shown in FIG. 4A. For example, a medical system 100 may be designed with a first preshaped arm 102 and a second steerable arm 102 comprising three steering members 128. In another embodiment, a medical system 100 may be designed with a first steerable arm 102 comprising a single steering member 128 and a second steerable arm 102 comprising two steering members 128. In another embodiment, a medical system 100 may be designed with a first preshaped arm 102 steered by a single pre-shaped stylet and a second steerable arm 102 comprising two steering members 128.

Figure 4B:
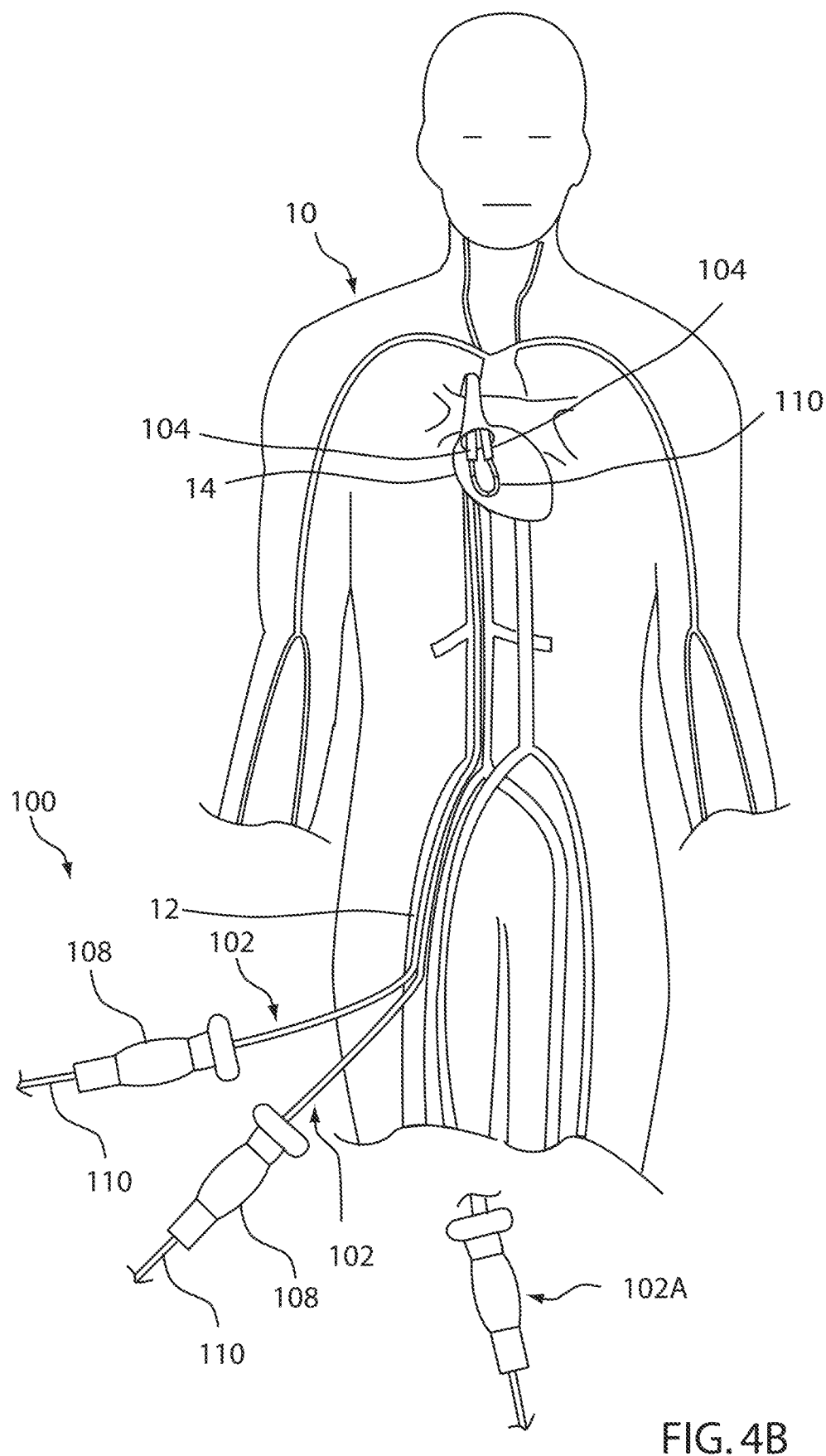
FIG. 4B illustrates one possible use of the medical system shown in FIG. 4A.

FIG. 4B illustrates one possible use of a medical system 100 as shown in FIG. 4A. In this example, medical system 100 is used to perform an endovascular cardiac procedure using one or more medical components 110. As shown, a physician directs first and second arms 102 into the body 10. In this variation, the first and second arms 102 are inserted through the femoral vein 12 and ultimately advanced into a right atrium of the heart 14 via the inferior vena cava. However, any known access methods may be used to gain entry.

As noted above, arms 102 can be coupled via first and/or second medical components 110 when inserted into the body. Alternatively, medical system 100 is configured so that the medical component(s) 110 can be advanced in and out of (or distal and proximal to) first and second arms 102. This construction allows a physician to remove the medical component 110 from the first arm 102 or second arm 102 to ease insertion of the respective arms 102 into the patient's body. For example, the arms can be inserted into separate entry point or each arm can be separately maneuvered to the target site where the arms are ultimately coupled. In other words, medical system 100 can be inserted into a patient without the arms 102 being coupled by the medical component 110. Once the arms 102 are positioned at or near the target site, medical component 110 can be advanced from first steerable arm 102 to second arm 102. In some variations, medical component 110 can be affixed to one arm 102 so that it engages that arm 102 without extending through the entire length of that arm 102. Alternatively, medical component 110 can be advanced from first arm 102, through second arm 102 until medical component 110 extends out of handle 108 of second arm 102 as shown in FIG. 4B.

FIG. 4B also shows an optional third steerable arm 102A. As noted above, medical system 100 can include any number of additional steerable arms 102 that can be used to aid in positioning medical component 110. In any case, once the physician places medical system 100 within the target site (the right atrium), arms 102 provide the physician with the improved ability to maneuver the medical component or components 110 using distal portions 104 of arms 102.

Any of the arms 102 disclosed herein may comprise one or more plastically deformable distal portions 104. The plastically deformable portions are designed such that they deform elastically while being introduced into the target tissue but can be deformed plastically by the user on application of a sufficient force. Thus, in this embodiment, distal portions 104 are user shapeable.

FIG. 4C shows an alternate embodiment of the medical system of FIG. 4A showing first medical component 110 comprising six functional elements 112. In one embodiment, functional elements 112 are electrodes. In one embodiment, the electrodes are electrophysiological radiofrequency ablating electrodes. Although six electrodes are shown in the embodiment of FIG. 4C, additional variations of medical component 110 are possible comprising from one to ten or more electrodes. Thus medical component 110 of FIG. 4C comprises an array of electrodes. In the embodiment, spacing between adjacent functional elements 112 is the same. In an alternate embodiment, the spacing between adjacent functional elements 112 is not the same. In FIG. 4C, the radiofrequency ablating electrodes may be energized independently of each other. In an alternate embodiment, the radiofrequency ablating electrodes may function as an array of electrodes, two or more of which are energized by a single transmission line. In any case, variations of medical system 100 can include electrodes, or other energy delivery means (e.g., microwave antennas, resistive heating elements, or any other energy delivery means disclosed herein) that provide a physician with the ability to create discrete lesions as well as continuous or overlapping lesions.

In one embodiment, the length of the radiofrequency electrodes is between 0.1 mm and 10 mm. The radiofrequency electrodes may be adapted to transmit radiofrequency energy at a specified frequency lying between 0.1 KHz and 100 MHz. Alternately, instead of radiofrequency electrodes, medical component 110 may comprise other elements for ablating or destroying tissue or other working elements 112 disclosed elsewhere in the specification.

In any of the embodiments herein, medical component 110 may be adapted to deliver two or more treatment modalities. The two or more modalities may be selected from the group consisting of: radiofrequency energy, microwave energy, a cryogenic zone, laser, ultrasound energy, IR energy, visible light, thermal energy, X-rays and other ionizing radiation and chemicals.

FIG. 4D shows an alternate embodiment of the medical system of FIG. 4A showing first medical component 110 comprising a long, linear active region 142. Such a design is useful to diagnose or treat a long segment of tissue. For example, medical component 110 in FIG. 4A and any of the embodiments of working element 112 or active region 142 herein may be used to ablate a long, linear region of tissue to create a linear ablation. The long, linear active region 142 can be repositioned to another tissue location after a first treatment of tissue. Thereafter, the long, linear active region 142 may be used again to diagnose or treat tissue. In one embodiment shown in FIG. 4D, active region 142 comprises a long, linear microwave antenna. Although only a single microwave antenna is shown in FIG. 4D, embodiments of medical component 110 are possible comprising two or more microwave antennas.

The length of first medical component 110 extending between the distal regions of arms 102 is substantially uniform in outer diameter. Alternate designs of first medical component 110 are possible where the outer diameter of medical component 110 extending between the distal regions of arms 102 is non-uniform. Also, in FIG. 4D, the stiffness of the region of first medical component 110 adjacent to the distal region 104 of one of arms 102 is substantially the same as the stiffness of the region of medical component 110 adjacent to the distal region 104 of the other of arms 102. Alternate designs of medical component 110 are possible where the stiffness of the region of first medical component 110 adjacent to the distal region 104 of one of arms 102 is substantially different from the stiffness of the region of medical component 110 adjacent to the distal region 104 of the other of arms 102. In this manner, designs of medical system 100 are possible where a physical property (e.g. stiffness, torquability, outer diameter, cross-sectional shape, radio-opacity, pushability/column strength, presence of one or more lumens, presence of one or more coatings, presence of one or more markers, lubricity, outer surface properties, porosity, storability, conductivity, presence of one or more metallic elements, dielectric constant, presence of one or more exit ports, color, elasticity, presence of one or more functional elements, etc.) of the region of first medical component 110 adjacent to the distal region 104 of one of arms 102 is substantially the same as or different from the physical property of the region of medical component 110 adjacent to the distal region 104 of the other of arms 102. Embodiments of medical system 100 comprising long linear active regions 142 disclosed herein can be designed to enable a user to place long linear active region 142 in any orientation and any position on the surface of a bodily tissue. Some examples of orientations and positions of long linear active region 142 relative to arms 102 are shown in FIGS. 6H-6K. Such a medical system 100 is advantageous to treat the interior of hollow organs or anatomical cavities in a minimally invasive manner. Arms 102 are introduceable into such hollow organs or anatomical cavities (e.g. lumens) through small sized natural or artificial openings. Thereafter, active region 142 can be placed on one or more locations in the hollow organs or anatomical cavities (e.g. lumens) to treat one or more locations in the hollow organs or anatomical cavities (e.g. lumens).

FIG. 4E shows an alternate embodiment of the medical system of FIG. 4A showing first medical component 110 comprising a centrally located active region 142 and multiple functional elements 112 on both sides of active region 142. In an alternate embodiment, one or more functional elements 112 are located only on one side of active region 142. In FIG. 4E, active region 142 comprises a long, linear region. Such a design is useful to diagnose or treat a long segment of tissue. In FIG. 4E, functional elements 112 may be electrophysiological mapping electrodes. In an alternate embodiment, medical component 110 comprises a centrally located active region 142 and two functional elements 112, one on each side of active region 142. In one method embodiment, medical system 100 is introduced or created in the anatomy. Thereafter, active region 142 is used to treat tissue. The signals from treated and/or untreated tissue are obtained from functional elements 112. Thereafter, active region 142 may be repositioned to treat other regions of the anatomy.

FIG. 4F shows an alternate embodiment of the medical system of FIG. 4A showing first medical component 110 comprising multiple functional elements 112 and a tether or spline 114. In the embodiment shown in FIG. 4F, tether or spline 114 is permanently attached to medical component 110. In an alternate embodiment, tether or spline 114 is attachable to and detachable from medical component 110 by a user. Tether 114 has stiffness less than the stiffness of the region of medical component 110 comprising functional elements 112. This enables the user to pull or release tether 114 as desired to position first medical component 110 in a desired location and orientation. In FIG. 4F, first medical component comprises a first region containing functional elements 112 and a second region defined by tether 114. In one embodiment, one or more functional elements 112 are located only on the portion of medical component 110 adjacent to the tether 114 i.e. only on the distal portion of the first region. In one embodiment, tether 114 is floppy or string-like.

FIG. 4G shows an alternate embodiment of the medical system of FIG. 4A showing an assembly comprising two medical components 110 comprising multiple functional elements 112 joined at their distal ends by a tether or spline 114. In the embodiment shown in FIG. 4F, tether or spline 114 is permanently attached to medical components 110. In an alternate embodiment, tether or spline 114 is attachable to and detachable from medical components 110 by a user. Tether 114 has stiffness less than the stiffness of the region of medical components 110 comprising functional elements 112. This enables the user to collapse the assembly comprising two medical components 110 and tether 114 to a low profile for insertion through a narrow opening. In one embodiment, one or more functional elements 112 are located only on the portion of medical components 110 adjacent to tether 114. In one embodiment, tether 114 is floppy or string-like.

Figure 4H:
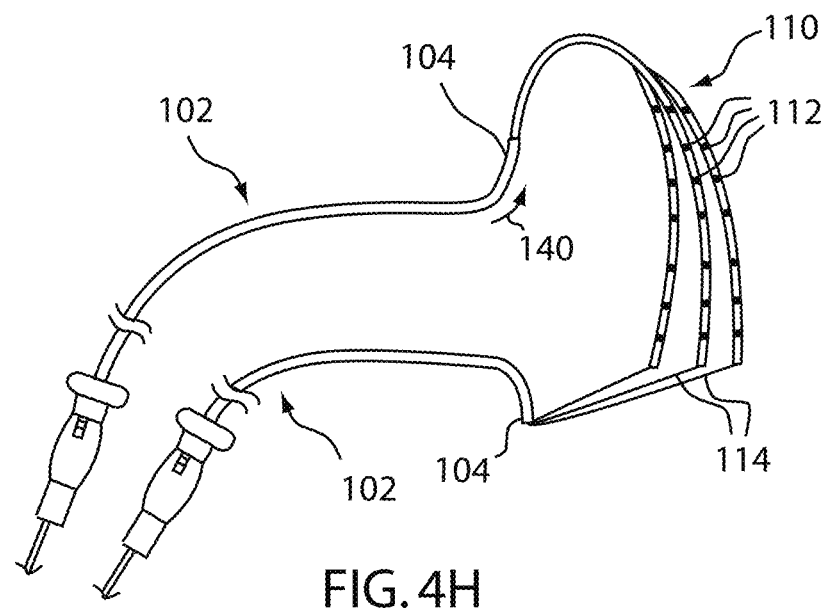
FIG. 4H shows an alternate embodiment of the medical system of FIG. 4F showing a medical component comprising multiple branches, each branch containing multiple functional elements.

FIG. 4H shows an alternate embodiment of the medical system of FIG. 4F showing medical component 110 comprising multiple branches, each branch containing multiple functional elements 112. Each branch is connected to a tether 114. Thus medical component 110 comprises multiple tethers 114. In the embodiment shown in FIG. 4H, tethers 114 are permanently attached to medical component 110. In an alternate embodiment, tethers 114 are attachable to and detachable from medical component 110 by a user. Tethers 114 have stiffness less than the stiffness of the region of medical component 110 comprising functional elements 112. This enables the user to pull tethers 114 and release tethers 114 as desired to position various branches of first medical component 110 in a desired location and orientation. In FIG. 4F, first medical component comprises a first region containing multiple branches, each containing multiple functional elements 112 and a second region defined by tethers 114. In one embodiment, one or more functional elements 112 are located only on the portion of medical component 110 adjacent to tethers 114 i.e. only on the distal portion of the first region. Any of the tethers 114 disclosed herein may be floppy or string-like. The first region of first medical component 110 is designed to be collapsible into an arm 102 for introduction into the anatomy. In the embodiment shown in FIG. 4H, first medical component 110 comprises three branches. Other embodiments are possible containing anywhere between two to ten branches. In an alternate embodiment, each of the branches is a spline that extends from the distal region of one of the arms 102 till the distal region of the other of the arms 102. The branches (splines) in this embodiment may or may not contain any tethers 114.

Figure 4I:
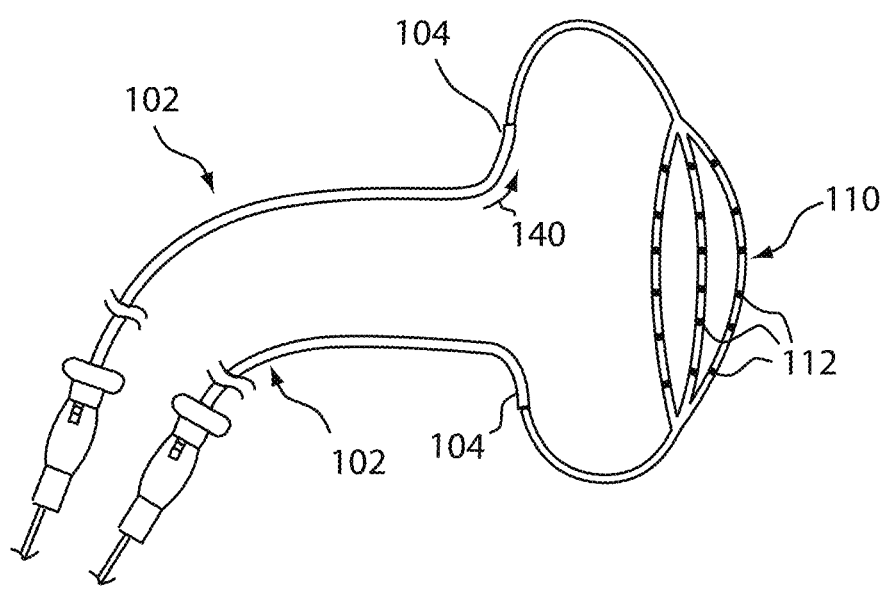
FIG. 4I shows an alternate embodiment of the medical system of FIG. 4C showing a first medical component comprising a basket containing multiple functional elements.

FIG. 4I shows an alternate embodiment of the medical system of FIG. 4C showing first medical component 110 comprising a basket containing multiple functional elements 112. The basket comprises multiple branches with each branch containing multiple functional elements 112. In the embodiment shown in FIG. 4I, the multiple branches are substantially parallel to each other. In one embodiment, one or more functional elements 112 are located only on the central portion of the branches. The basket is designed to collapse within an arm 102 for introduction into the anatomy. After exiting arm 102, the basket is designed to expand into an expanded configuration as shown. In the embodiment shown in FIG. 4I, first medical component 110 comprises three branches. Other embodiments are possible containing anywhere between two to ten branches. In an alternate embodiment, the length of the basket region is such that each of the branches extends from the distal region of one of arms 102 till the distal region of the other of arms 102. The branches (splines) in this embodiment do not contain any tethers 114. Features of any of the embodiments shown in FIGS. 4C-4K may be added to other embodiments disclosed herein.

Figure 4J:
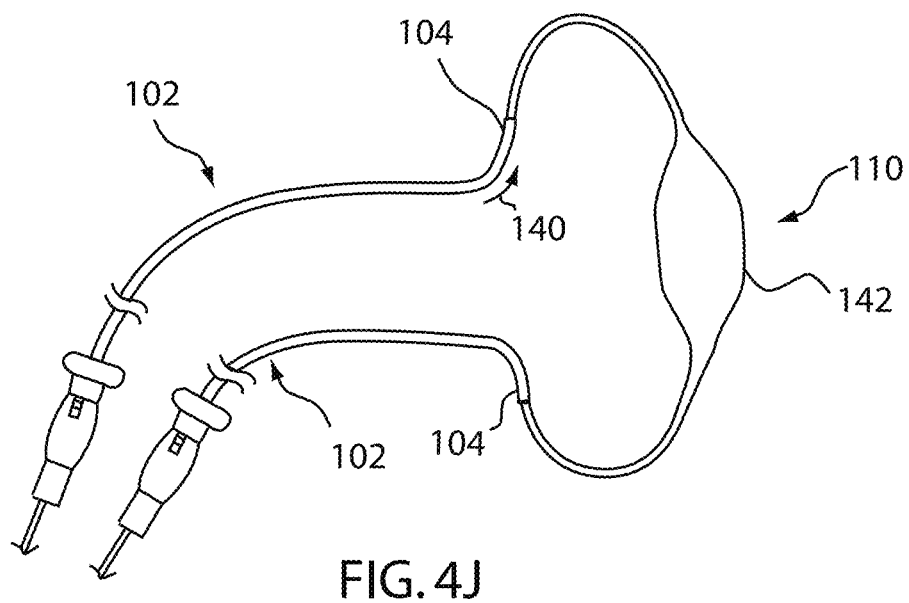
FIG. 4J shows an alternate embodiment of the medical system of FIG. 4A showing a first medical component comprising an active region wherein the active region comprises a balloon.

FIG. 4J shows an alternate embodiment of the medical system of FIG. 4A showing first medical component 110 comprising an active region 142 wherein the active region 142 comprises a balloon. The balloon can be expanded to access target tissue not directly in the path of first medical component 110. In one embodiment, active region 142 comprises a balloon with an ablation modality selected from the group consisting of: microwave energy, radiofrequency energy, cryo ablation, high intensity ultrasound energy, chemical ablation, laser ablation, ionizing radiation and thermal ablation. The balloon may be made of compliant, semi-compliant or non-compliant materials. The balloon may be inflated by gas or a liquid e.g. saline. In one embodiment, the ablation modality is located inside the balloon. Examples of such ablation modalities include, but are not limited to elements for delivering: lasers, focused ultrasound, cryogenic elements and microwave. The walls of the balloon in such case are adequately transparent to the passage of the energy. In another embodiment, the ablation modality is located on the surface the balloon. Examples of such ablation modalities include, but are not limited to elements for delivering: radiofrequency energy, thermal energy, lasers, focused ultrasound, cryogenic elements and microwave. The walls of the balloon in such case may be adequately resistant to the effects of the ablation modality.

Figure 4K:
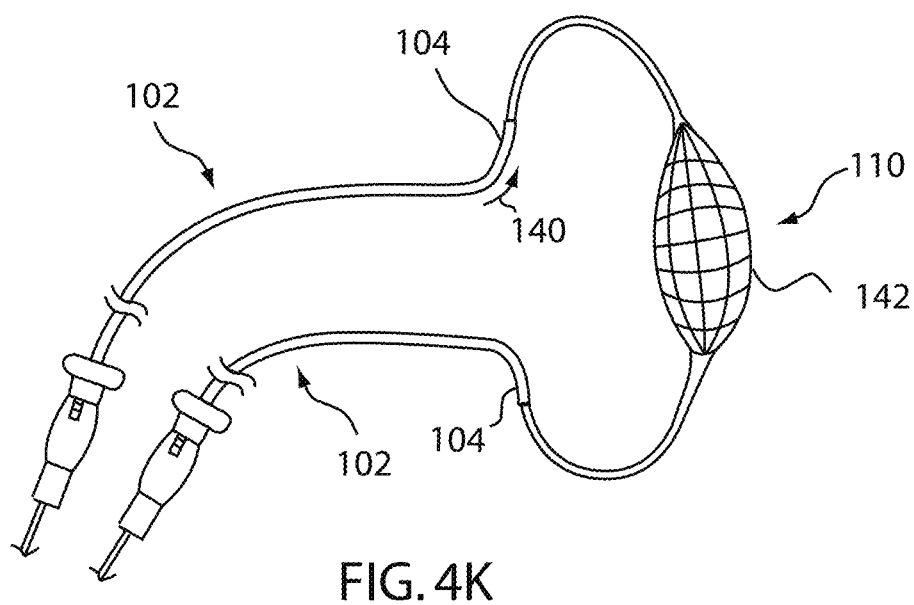
FIG. 4K shows an alternate embodiment of the medical system of FIG. 4C showing a first medical component comprising a mesh basket.

FIG. 4K shows an alternate embodiment of the medical system of FIG. 4C showing first medical component 110 comprising a mesh basket. The basket comprises multiple branches. In the embodiment shown in FIG. 4K, the multiple branches intersect with each other. The basket is designed to collapse within an arm 102 for introduction into the anatomy. After exiting arm 102, the basket is designed to expand into an expanded configuration as shown. One or more portions of the basket may have a layer of electrical insulation. In one embodiment, the mesh basket is energized by an energy source such that the energy can be delivered to the surrounding anatomy. For example, the mesh basket may be energized by radiofrequency energy such that the radiofrequency energy can be delivered to the surrounding anatomy.

Various embodiments of medical system 100 can be designed wherein first medical component 110 comprises only a single functional element 112 or active region 142. Such embodiments may be adapted to deliver an ablation modality including, but not limited to an ablation modality selected from the group consisting of microwave energy, radiofrequency energy, cryo ablation, ultrasound energy, chemical ablation, laser ablation, IR energy, visible light, X-rays and other ionizing radiation and thermal ablation.

Any of the components disclosed herein that comprise electrodes may be designed such that the electrodes project out of the outer surface of the component to ensure better proximity to target tissue. Alternately, the components may be designed such that the electrodes do not project out of the outer surface of the components.

Figure 5A:
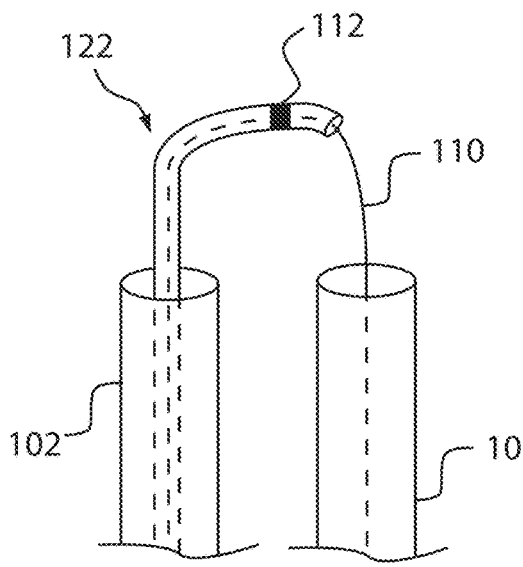
FIGS. 5A-5C show embodiments of a medical system comprising a first medical component comprising a tether or rail or guidewire or stylet.
Figure 5B:
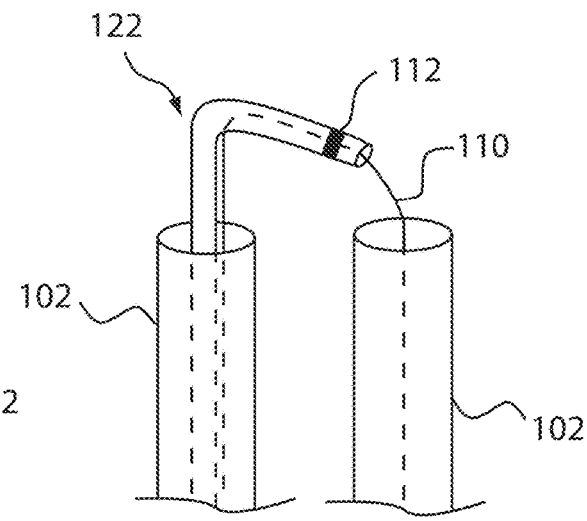
Figure 5C:
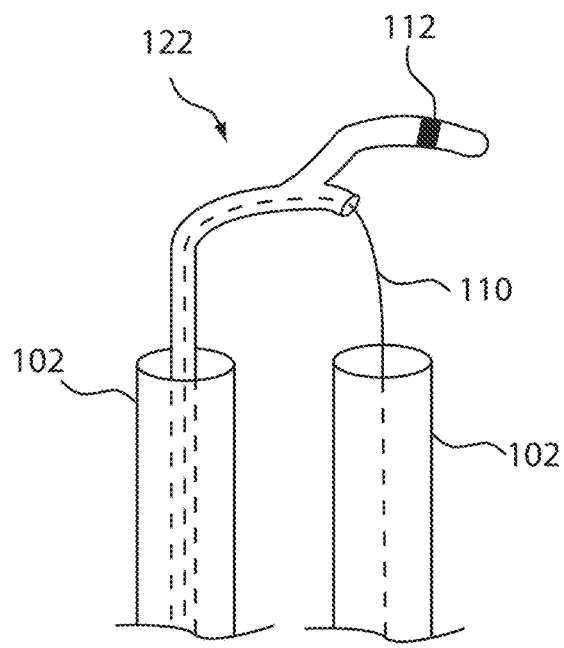

In additional embodiments, a first medical component 110 may be used to guide the introduction and/or the positioning of a second medical component 122 in the anatomy. Examples of medical systems 100 comprising a first medical component 110 used to guide the introduction and/or the positioning of a second medical component 122 are shown in FIGS. 5A-5F. In FIGS. 5A-5C, first component 110 comprises a tether or rail or guidewire or stylet. First medical component 110 may have one or more coatings on its outer surface. Examples of such coatings include, but are not limited to radio-opaque coatings, lubricious coatings, hydrophilic coatings, hydrophobic coatings. The entire length of first medical component 110 may be radio-opaque. For example, a coaxial cable or other elements supplying microwave energy to working element 112 may be radiopaque. In another embodiment only a segment of first medical component 110 is radio-opaque. In one embodiment, first medical component 110 has a circular cross-section with an outer diameter between 0.5 mm and 3 mm. In one embodiment, first medical component 110 is sufficiently stiff such that the introduction of second medical component 122 over first medical component 110 does not substantially distort the position and the orientation of first medical component 110.

As shown in FIG. 5A, second medical component 122 comprises a lumen and can be advanced over first medical component 110 which functions as a rail, guide, or tether. In this embodiment, the lumen is an end-to-end lumen. In such a case, the first and second medical components 110 and 122 comprise separate medical devices. In one embodiment, first medical component 110 is a guidewire. Alternate embodiments of second medical component 122 are possible that do not contain an end-to-end lumen. FIG. 5B shows a variation of the embodiment of FIG. 5A in which second medical component 122 comprises a rapid-exchange lumen. In the embodiments shown in FIGS. 5A and 5B, functional element 112 on second medical component 122 can be positioned in a desired location and orientation by one or more of: torquing one or both of arms 102, deflecting a deflectable or steerable region of one or both of arms 102, advancing or withdrawing one or both of arms 102, advancing or withdrawing one or both segments of first medical component 110, advancing or withdrawing second medical component 122 and engaging a steering or deflecting mechanism on second medical component 122.

FIG. 5C shows an embodiment of a medical system 100 comprising a first medical component 110 used to guide the introduction and/or the positioning of a second medical component 122 wherein the distal portion of second medical component 122 is offset from the proximal region of second medical component 122. This embodiment is useful to reach tissue that does not lie directly on the path of first medical component 110. In the embodiment shown in FIG. 5C, functional element 112 on second medical component 122 can be positioned in a desired location and orientation by one or more of: torquing one or both arms 102, deflecting a deflectable or steerable region of one or both arms 102, torquing second medical component 122, advancing or withdrawing one or both arms 102, advancing or withdrawing one or both segments of first medical component 110, advancing or withdrawing second medical component 122 and engaging a steering or deflecting mechanism on second medical component 122.

In FIGS. 5A-5C and FIG. 5E, second medical component 122 may be an energy transfer device having a functional element 112 adapted to transfer energy. Second medical component 122 could also include multiple functional elements 112. Any of the functional elements 112 discussed herein may be an energy transfer element. For example, a functional element 112 may be one of: radiofrequency electrodes (monopolar or bipolar), a DC resistive heating source, a microwave antenna, ultrasound energy transfer element, laser source, a cryogenic element. Any of the functional elements 112 may be sensors or information receiving elements. For example, such elements can include electrodes (that detect voltage, current and/or impedance), temperature sensors, pressure sensors, light measurement devices, infrared sensors, chemical sensors, radiation sensors, deformation sensors, or any other type of sensors that observe or measure a state or condition of tissue or the body. Such sensors or information receiving elements can also be present on any of the devices disclosed herein. The combination of first medical component 110 and second medical component 122 may be designed such that first medical component 110 does not substantially interfere with the functioning of energy transfer elements 112. In FIGS. 5A-5C and 5E-5F, second medical component 122 and/or first medical component 110 may comprise one or more markers e.g. radio-opaque markers to enable a user to track the position of second medical component 122 and/or first medical component 110 in the anatomy. Any of the functional elements 112 herein may be a delivery element for delivering one or more drugs or chemicals (e.g. contrast agent) or biologicals (e.g. stem cells, fibroblasts, etc.). Any of the functional elements 112 may be a mechanical or electromechanical surgical tool.

In an alternative variation, the first and second medical components 110 and 122 can be integrated in a single device such that energy transfer device or second medical component 122 includes a rail or tether 114 that is affixed to a distal end. Rail or tether 114 can be used to either pull the device through an arm 102 (as a tether member) or provide sufficient column strength and flexibility to aid in positioning of a functional element 112 as desired (as a flexible member or flexible tether). In another variation of medical system 100, the first and second medical components 110 and 122 can be integrated together as a single device and a portion of second component 122 is torqueable and a rail or tether portion of component 122 is non-torqueable. Such a variation can be designed, for example, by having the rail or tether portion be more flexible than the torqueable portion of component 122. Thus when the torqueable portion of second component 122 is twisted by a user, the twist is substantially transmitted to the distal region of first component 110.

Figure 5D:
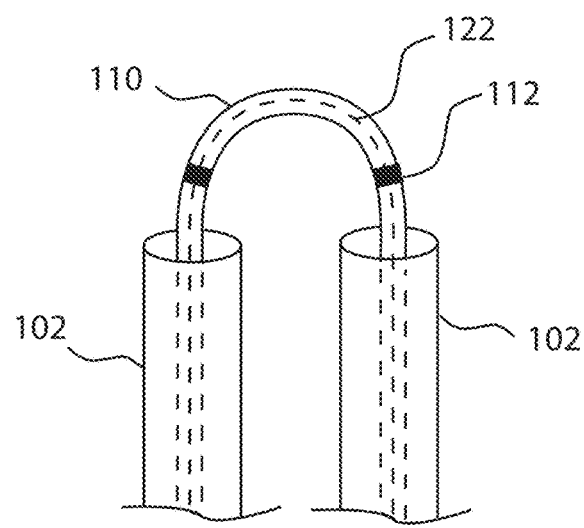
FIG. 5D shows an embodiment of a medical system comprising a first medical component used to guide the introduction and/or the positioning of a second medical component, wherein the second medical component is enclosed within at least a portion of the first medical component.

FIG. 5D shows an embodiment of a medical system 100 comprising a first medical component 110 used to guide the introduction and/or the positioning of a second medical component 122 wherein second medical component 122 is enclosed within at least a portion of the first medical component. In the example shown in FIG. 5D, second medical component 122 is slidably enclosed within a lumen of first medical component 110. The region of second medical component 122 distal to the distal ends of arms 102 is entirely enclosed within the region of first medical component 110 distal to the distal ends of arms 102. In one embodiment, second medical component 122 comprises an energy transfer element. The energy transfer element of second medical component 122 and first medical component 110 are designed such that the energy can pass through first medical component. In one embodiment, energy transfer element of second medical component 122 comprises a microwave antenna and first medical component 110 is transmissible to microwave energy. In another embodiment, energy transfer element of second medical component 122 comprises one or more radiofrequency ablation electrodes and first medical component 110 is porous. The interior of first medical component 110 may be filled with saline or another suitable conductive medium.

In another embodiment, energy transfer element of second medical component 122 comprises a laser source and first medical component 110 is transmissible to laser. In the embodiment shown in FIG. 5D, first medical component 110 comprises multiple functional elements 112 on its surface. The design and location of the functional elements 112 of first medical component 110 is such that they do not interfere with the passage of energy emitted by the energy transfer element of second medical component 122. For example, in one embodiment, second medical component 122 comprises a microwave antenna and multiple functional elements 112 are mapping electrodes. In this embodiment, first medical component 110 is designed such that the microwave energy can pass through first medical component 110 without substantial interference from the mapping electrodes.

In the embodiment shown in FIG. 5D, energy transfer element of second medical component 122 can be positioned in a desired location and orientation by one or more of: torquing one or both arms 102, deflecting a deflectable or steerable region of one or both arms 102, advancing or withdrawing one or both arms 102, advancing or withdrawing one or both segments of first medical component 110, advancing or withdrawing one or both segments of second medical component 122, engaging a steering or deflecting mechanism on second medical component 122 and engaging a steering or deflecting mechanism on first medical component 110.

Figure 5E:
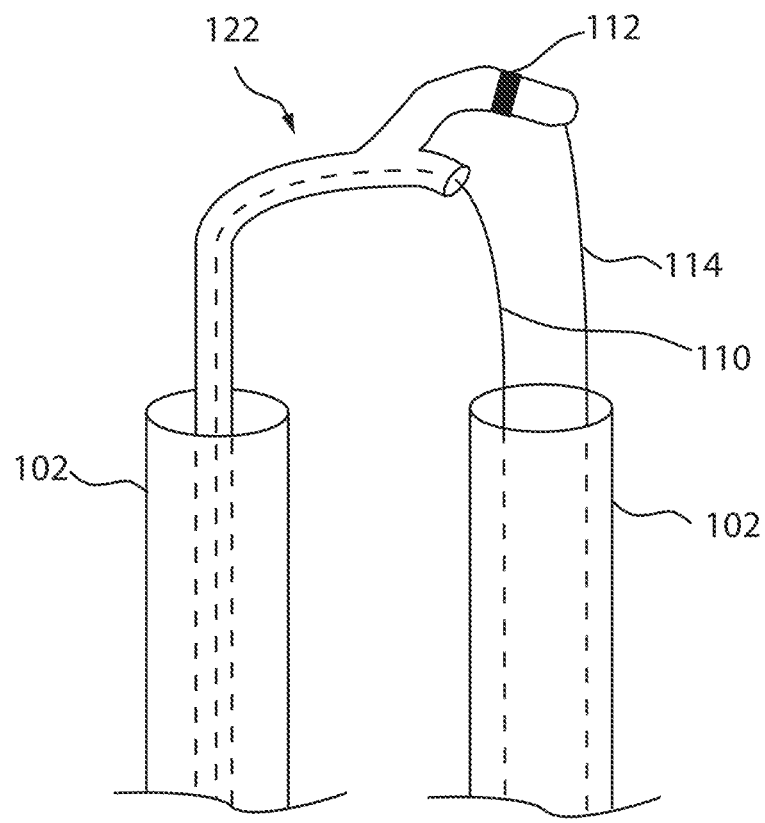
FIG. 5E shows a variation of the embodiment of the medical system of FIG. 5C.

FIG. 5E shows a variation of the embodiment of a medical system 100 of FIG. 5C. In the example shown in FIG. 5E, second medical component 122 further comprises a manipulating member capable of manipulating the distal region of second medical component 122. In one embodiment, the manipulating member is a wire or tether or string 114 connected to the distal region of second medical component 122. Manipulating member passes through a lumen of an arm 102. Manipulating member can be used to deflect the distal end of second medical component 122 to further position functional element 112 in a desired region. In the embodiment shown in FIG. 5E, functional element 112 of second medical component 122 can be positioned in a desired location and orientation by one or more of: torquing one or both arms 102, deflecting a deflectable or steerable region of one or both arms 102, advancing or withdrawing one or both arms 102, advancing or withdrawing one or both segments of first medical component 110, advancing or withdrawing second medical component 122, engaging a steering or deflecting mechanism on second medical component 122 and manipulating the manipulating member. In the embodiments where manipulating member has a sufficient stiffness, the step of manipulating the manipulating member comprises one or more of pulling manipulating member, pushing manipulating member and torquing manipulating member. In the embodiments where manipulating member is a wire or tether or string 114 with low stiffness, the step of manipulating the manipulating member comprises one or more of pulling manipulating member and releasing manipulating member. Second medical component 122 may comprise more than one manipulating members. Each of the multiple manipulating members may be attached to or cooperate with differing distal regions on second medical component 122. One or more elongate medical devices (e.g. steerable sheaths) may slide over any manipulating member or any tether disclosed in this disclosure.

Figure 5F:
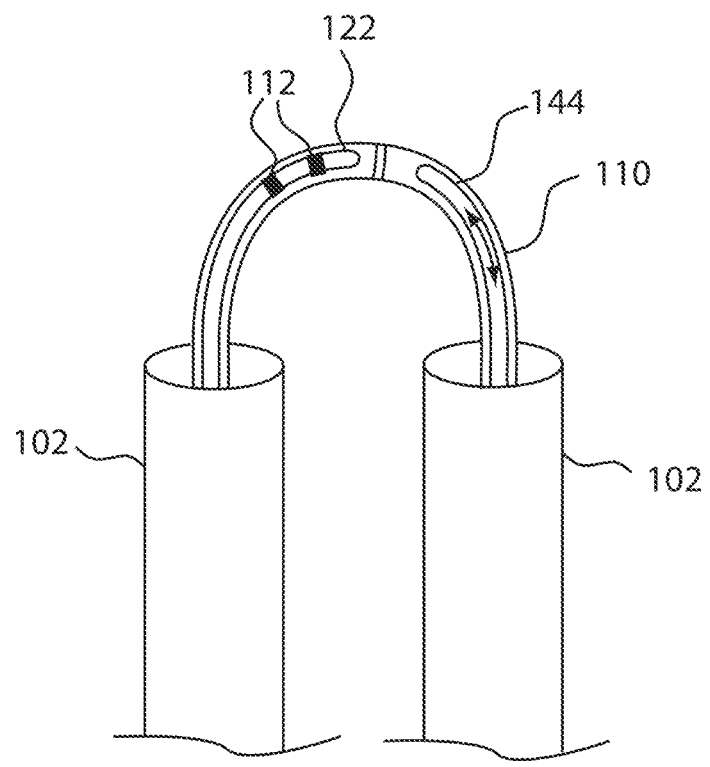
FIG. 5F shows an embodiment of a medical system comprising a hollow first medical component used to guide the introduction and/or the positioning of a second medical component, wherein second medical component is enclosed within at least a portion of the first medical component.

FIG. 5F shows an embodiment of a medical system 100 comprising a hollow first medical component 110 used to guide the introduction and/or the positioning of a second medical component 122 wherein second medical component 122 is enclosed within at least a portion of the first medical component 110. The region of second medical component 122 distal to the distal ends of arms 102 is entirely enclosed within first medical component 110. Second medical component 122 comprises one or more functional elements 112 e.g. energy transfer elements. In the example shown in FIG. 5F, second medical component 122 is slidably enclosed within a lumen of first medical component 110. Thus the position of one or more functional elements 112 is adjustable relative to the position of a region of first medical component 110 distal to the distal ends of arms 102.

The energy transfer elements of second medical component 122 may be designed such that the energy can pass through first medical component 110. In one embodiment, energy transfer element of second medical component 122 comprises a microwave antenna and first medical component 110 is transmissible to microwave energy. In another embodiment, energy transfer element of second medical component 122 comprises one or more radiofrequency ablation electrodes and first medical component 110 is porous. The interior of first medical component 110 may be filled with saline or another suitable conductive medium. In another embodiment, energy transfer element of second medical component 122 comprises a laser source and first medical component 110 is transmissible to laser. In the embodiment shown in FIG. 5D, first medical component 110 also comprises multiple functional elements 112 on its surface. The design and location of the functional elements 112 of first medical component 110 is such that they do not interfere with the passage of energy emitted by the energy transfer element of second medical component 122. For example, in one embodiment, second medical component 122 comprises a microwave antenna and multiple functional elements 112 are mapping electrodes. In this embodiment, first medical component 110 is designed such that the microwave energy can pass through first medical component 110 without substantial interference from the mapping electrodes. First medical component 110 also encloses a sliding stiffening stylet 144. In the embodiment shown in FIG. 5F, stiffening stylet 144 is enclosed in a lumen of first medical component 110. The lumen containing stiffening stylet 144 is separated from the lumen containing second medical component 122 by a partition. The region of first medical component 110 that encloses stiffening stylet 144 is preferably softer than the region of first medical component 110 that encloses second medical component 122. Thus sliding stiffening stylet 144 changes the shape of the region of first medical component 110 distal to the distal ends of arms 102.

In the embodiment shown in FIG. 5F, energy transfer elements of second medical component 122 can be positioned in a desired location and orientation by one or more of: torquing one or both arms 102, deflecting a deflectable or steerable region of one or both arms 102, advancing or withdrawing one or both arms 102, advancing or withdrawing one or both segments of first medical component 110 relative to one or both arms 102, advancing or withdrawing second medical component 122, sliding stiffening stylet 144 and torquing stiffening stylet 144.

Although in FIGS. 5A-5F, first medical component 110 is shown to introduce a single second medical component 122, first medical component 110 can comprise features (e.g. extra lumens, larger lumens, positioning elements, etc.) that enable the user to introduce more than one second medical components 122 along the first medical component 110. In one method embodiment, multiple second medical components 122 may be introduced simultaneously along the first medical component 110. For example, two second medical components 122 may be introduced simultaneously through a single lumen of first medical component 110. In another method embodiment, multiple second medical components 122 may be introduced sequentially along the first medical component 110. In one such method embodiment, a second medical component 122 is introduced through a lumen of first medical component 110; the second medical component 122 is used to perform a procedure; the second medical component is removed from the lumen and another second medical component 122 is introduced through the lumen of first medical component 110.

Active region 142 in the present invention may be designed to emit any of the energies (e.g. microwave, radiofrequency, ionizing radiation, infra-red light, etc) disclosed herein. FIGS. 6A-6G show various alternate embodiments of the medical system 100 of FIG. 4A wherein elongate active region 142 comprises one or more one or more functional elements 112 in the form of radiofrequency electrodes 112. Although the embodiments in FIGS. 6A-6G have been substantially described in terms of radiofrequency ablation methods and devices, several microwave ablation devices and methods are also a part of the present invention. The embodiments of FIGS. 6A-6G may also comprise a second medical component 122 that slides over tether 114 of first medical component 110. In one embodiment, second medical component 122 is a mapping sheath comprising mapping electrodes 118 and a lumen through which one or more fluids such as contrast agents can be introduced into the anatomy. Second medical component 122 may be used to collect electrophysiological information. The electrophysiological information may be used for diagnosis of a disease and/or for determining the outcome of a procedure. As shown in FIG. 6M, the distal ends of first medical component 110 and second medical component 122 in FIGS. 6A-6G may be detachably attachable to each other to create a "U-mode".

FIG. 6A shows medical system 100 wherein medical component 110 comprises multiple radiofrequency electrodes. Although FIG. 6A shows medical component 110 comprising four working elements 112 in the form of radiofrequency electrodes, variations of medical system 100 are possible comprising anywhere from 2-32 electrodes. Two or more radiofrequency electrodes 112 may be coupled together or energized by a single source. Radiofrequency electrodes 112 may be designed for multi-phase radiofrequency ablation by having multiple radiofrequency electrodes 112 capable of producing multiple current paths in the ablation zone. Radiofrequency electrodes 112 are fed by one or more conducting wires extending through a length of medical component 110.

In the embodiments disclosed herein, radiofrequency electrodes 112 are fed by anywhere from one to thirty two conducting wires. Several variations are possible wherein more than one radiofrequency electrodes 112 are fed by a single conducting wire. In the embodiments herein comprising multiple radiofrequency electrodes 112, adjoining radiofrequency electrodes 112 may be spaced apart such that the treatment zones formed by adjacent radiofrequency electrodes 112 overlap. For example, the ablation zone formed by two adjoining radiofrequency ablation electrodes 112 may overlap due to heat spread in target tissue to form a single large ablation zone. The multiple radiofrequency ablation electrodes 112 may operate in a monopolar or bipolar configuration. In another embodiment, multiple radiofrequency ablation electrodes 112 are capable of operating in two modes: a monopolar mode or a bipolar mode. A user selects the mode (monopolar or bipolar) depending on his need. For example, the user may select the monopolar mode for creating deep lesions and the bipolar mode for creating surface lesions. In the case of bipolar radiofrequency electrodes 112, adjacent radiofrequency electrodes 112 may be electrically coupled. In an alternate embodiment of bipolar radiofrequency electrodes 112, non-adjacent radiofrequency electrodes 112 may be electrically coupled. Multiple radiofrequency ablation electrodes 112 may be energized simultaneously. In another embodiment, multiple radiofrequency ablation electrodes 112 are energized sequentially. In another embodiment, only a few selected multiple radiofrequency ablation electrodes 112 are energized at a time. When one or more of the multiple radiofrequency ablation electrodes 112 are not energized, the non-energized electrodes may have a high impedance. This is useful, for example, to reduce interference from the non-energized radiofrequency ablation electrodes 112. In one embodiment, medical component 110 comprises multiple radiofrequency electrodes 112 coupled to a reference electrode that is located in the pericardial region. In an alternate embodiment, medical component 110 comprises a single reference electrode coupled to an array of multiple radiofrequency electrodes 112 located in the pericardial region. The voltages used to energize the multiple radiofrequency ablation electrodes 112 may be same or different. The frequencies of radiofrequency energy used to energize the multiple radiofrequency ablation electrodes 112 may be same or different. In one embodiment, the action of one or more multiple radiofrequency ablation electrodes 112 is controlled by controlling the voltage applied to the one or more multiple radiofrequency ablation electrodes 112.

The one or more radiofrequency electrodes 112 disclosed in FIGS. 6A-6G may be energized by a variety of controlled waveforms. In one embodiment, the waveforms used to energize one or more radiofrequency electrodes 112 are changeable. The one or more electrodes 112 and associated waveforms may be designed to provide one of the following actions: cutting, coagulating, desiccating and fulgurating tissue. The one or more electrodes 112 and associated waveforms may also be designed to provide multiple actions described above, for example a combination of cutting and coagulating. One or more electrodes 112 may be designed such that they transmit and/or receive energy uniformly over their surface. Alternately, one or more electrodes 112 may be designed such that they transmit and/or receive energy non-uniformly over their surface. For example, a portion of one or more electrodes 112 may be insulated such that one or more electrodes 112 transmit and/or receive energy only along particular regions.

FIG. 6B shows medical system 100 wherein medical component 110 comprises a single, long radiofrequency electrode. Radiofrequency electrode 112 may have a length ranging from 5 to 80 mm. Medical component 110 may further comprise additional long radiofrequency electrodes 112.

FIG. 6C shows medical system 100 wherein medical component 110 comprises multiple radiofrequency electrodes adapted to function in a monopolar configuration. Radiofrequency electrodes 112 may be energized singly or as a group. More than one radiofrequency electrode 112 may be energized at a time. The medical system 100 in FIG. 6C cooperates with a ground pad 146 that is connected to the patient.

FIG. 6D shows medical system 100 wherein medical component 110 comprises a steering modality adapted to deflect or otherwise change the shape of active region 142.

FIG. 6E shows medical system 100 wherein medical component 110 comprises a single, long radiofrequency electrode arranged in a spiral configuration. Radiofrequency electrode 112 may have a length ranging from 5 to 300 mm. Medical component 110 may further comprise additional radiofrequency electrodes 112 also arranged in spiral configuration.

FIG. 6F shows medical system 100 wherein medical component 110 comprises multiple long radiofrequency electrodes arranged parallel to each other. In one embodiment, medical component 110 comprises multiple radiofrequency electrodes 112 in the form of multiple parallel splines. FIG. 6G shows a cross sectional view of the embodiment of FIG. 6F through the plane 6G-6G.

Any of the functional elements 112 disclosed herein may be heated using resistive heating by an electrical current. The resistively heated electrode may then be used for thermal treatment of tissue.

One or more radiofrequency electrodes 112 in FIGS. 6A-6G may be slidably positioned on medical component 110. This allows the user to change the position of one or more radiofrequency electrodes 112 relative to medical component 110. This can be used, for example, to access multiple target regions of the anatomy without changing the position of medical component 110. Thus multiple target regions of the anatomy may be treated without changing the position of medical component 110. In one embodiment, a slidable shaft comprising a single radiofrequency electrode 112 or an array or radiofrequency electrodes 112 is located within a portion of medical component 110.

Although most of the embodiments in FIGS. 6A-6G are described in terms of radiofrequency ablation electrodes 112, it should be noted that one or more of such electrodes may also be electrophysiological mapping electrodes or electrophysiological pacing electrodes. Further an additional ablation modality e.g. microwave ablation, cryoablation, laser ablation, HIFU ablation may be present along with one or more radiofrequency ablation electrodes 112. In alternate embodiments, the one or more radiofrequency ablation electrodes 112 on the devices disclosed in FIGS. 6A-6G as well as in other devices disclosed herein may be replaced by one or more of: basket electrodes and balloon electrodes. Such basket electrodes and balloon electrodes may have one or more of: elements for delivering HIFU, cryoablation elements, radiofrequency ablation electrodes, microwave antennas and laser ablation elements.

Any of the embodiments in FIGS. 6A-6G may comprise a sliding second medical component 122 that slides over tether 114 as shown in FIGS. 6L and 6M. In one embodiment, second medical component 122 is a mapping sheath comprising one or more mapping electrodes 118. Any of the embodiments in FIGS. 6A-6G may comprise a modality for obtaining feedback about a procedure or for sensing a patient parameter. For example, medical system 100 may comprise one or more of an impedance measuring modality, temperature measuring modality and pressure measuring modality. Any of the embodiments in FIGS. 6A-6G may comprise a cooling mechanism. Examples of such cooling mechanisms include, but are not limited to: active cooling and passive cooling. Any of the embodiments in FIGS. 6A-6G may be cooled by irrigation with a coolant such as saline. The coolant may be released into the exterior of the embodiment or may be circulated within the interior of the embodiment.

Active region 142, functional elements 112 and other regions of the devices disclosed herein may be used to treat a variety of internal organs including, but not limited to stomach, gall bladder, colon, rectum, urinary bladder, uterus and other regions of the female reproductive tract, regions of the male reproductive tract, esophagus, heart, lungs, liver, spleen, small intestine, and other pleural, visceral or peritoneal organs. The procedures may be performed on the surface of such organs, inside lumens or cavities of such organs or within an interior portion of such organs.

Arms 102 and medical component 110 may be manipulated to position active region 142 and/or functional element (s) 112 in several desired positions and orientations relative to arms 102. FIGS. 6H-6K show some examples of the medical system 100 with several possible orientations of regions of medical component 110. In FIGS. 6H-6K, arms 102 are introduced through a single opening or region into an anatomical cavity (e.g. the heart) such that they are introduced substantially parallel to each other. The distal regions of arms 102 have a steering region as shown. In FIG. 6H, arms 102 are introduced in the anatomy (e.g. inside a heart chamber) such that a looped medical component 110 extends between the distal regions of arms 102 as shown. Arms 102 may be advanced relative to one another and then articulated to orient the medical component 110 in a first profile as shown. Medical component 110 comprises an active region 142 (e.g. enclosing a microwave antenna) and multiple functional elements 112 (e.g. mapping electrodes). Active region 142 is spaced away from the shaft of arms 102 and is oriented at an angle of approximately 45 degrees to the length of arms 102 immediately proximal to the distal steering region of arms 102.

In the embodiment shown in FIG. 6H, medical component 110 comprises an integral tether 114. In an alternate embodiment, the distal end of the medical component 110 is reversibly attached to tether 114. In one such embodiment, the distal end of the medical component 110 comprises an opening. The opening functions essentially like the eye of a needle and allows a user to introduce a looped tether 114 through the opening. An advantage of this construction is the ability to disconnect tether 114 from medical component 110 remotely by opening tether 114 loop at a remote location (e.g. at a proximal region of tether 114) and pulling a free end of the tether 114. Tether 114 may be made of suitable metallic or non metallic materials. In one embodiment, tether 114 is made of a radiopaque metallic material such as Nitinol. As with other embodiments shown herein, one or both of arms 102 may be translated and the position of medical component 110 may be adjusted relative to the position of arms 102 to place the component 110 as desired against a contoured surface of tissue.

Figure 6I:
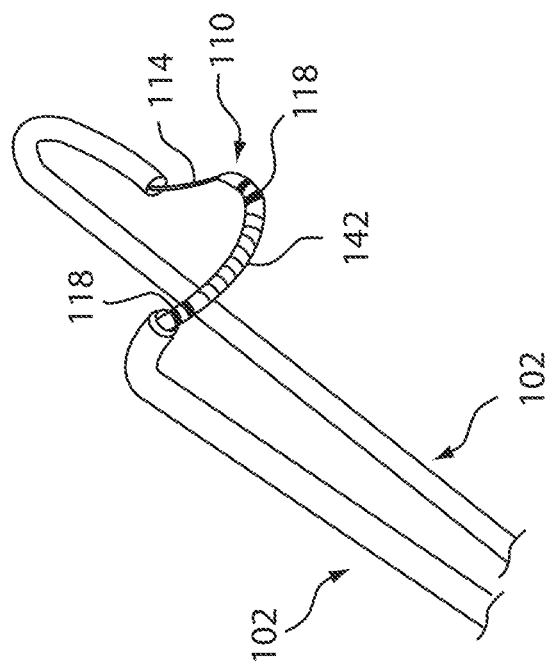
Figure 6H:
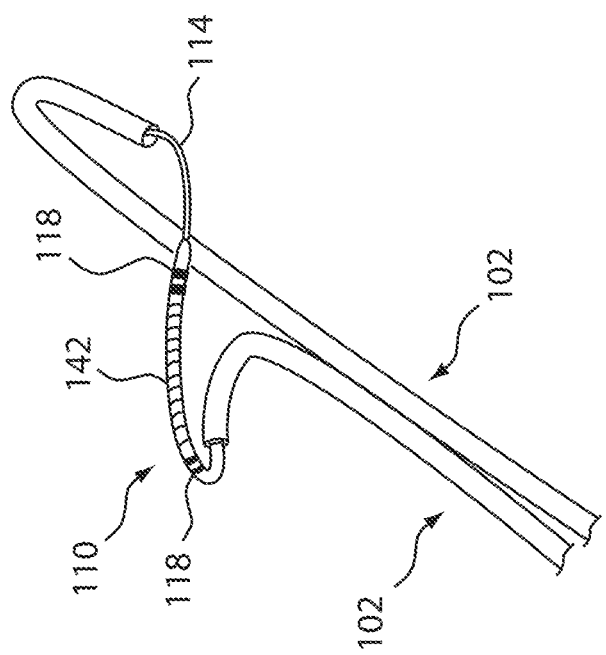

In FIG. 6I, arms 102 are manipulated such that active region 142 is oriented substantially perpendicular to arms 102. In particular, active region 142 is oriented substantially perpendicular to the regions of arms 102 proximal to the steering region. This embodiment may be used, for example, to ablate an ostium of a pulmonary vein. In FIG. 6J, arms 102 are manipulated such that active region 142 is oriented substantially parallel to arms 102. In particular, active region 142 is oriented substantially parallel to the regions of arms 102 proximal to the steering region. This embodiment may be used, for example, to ablate a linear region of tissue oriented parallel to arms 102. FIG. 6K shows an embodiment of arms 102 and medical component 110 wherein active region 142 is oriented substantially perpendicular to arms 102. This embodiment differs from the embodiment shown in FIG. 6I. In FIG. 6I, active region 142 is spaced away from regions of arms 102 proximal to the distal steering regions of arms 102.

In FIG. 6K, active region 142 is located in the vicinity of or immediately adjacent to regions of arms 102 proximal to the distal steering regions of arms 102. Thus active region 142 in FIG. 6K can be used to ablate tissue in the vicinity of arms 102. In a particular embodiment, arms 102 are introduced in the left atrium of the heart through a trans-septal opening or puncture. Active region 142 is used to treat tissue adjacent to the trans-septal opening or puncture e.g. tissue around the fossa ovalis. Thus active region 142 and regions of medical component 110 containing multiple functional elements 112 can be positioned at various distances from the shafts of arms 102. The average distance of active region 142 or regions of medical component 110 containing multiple functional elements 112 from the regions of arms 102 proximal to the distal steering regions of arms 102 can range anywhere from 0 to 15 centimeters. Also, active region 142 and regions of medical component 110 containing multiple functional elements 112 can be oriented at various angles relative to the shafts of arms 102. The average angle of active region 142 or regions of medical component 110 containing multiple functional elements 112 relative to the regions of arms 102 proximal to the distal steering regions of arms 102 can range anywhere from zero to 180 degrees. Similarly, in the embodiments wherein medical component 110 acts as a guide (guidewire, stylet, hollow tube, etc.), regions of second medical component 122 may be positioned at various angles and distances relative to arms 102.

The embodiments of FIGS. 6H-6K may also comprise a second medical component 122 (not shown) that slides over tether 114 of medical component 110. In one embodiment, second medical component 122 is a mapping sheath comprising mapping electrodes 112. In another embodiment, mapping sheath comprises a lumen through which one or more fluids such as contrast agents can be introduced into the anatomy. Second medical component 122 may be used to collect electrophysiological information. The electrophysiological information may be used for diagnosing a disease and/or for determining the outcome of a procedure. In one embodiment, the region of second medical component 122 emerging from an arm 102 is stiffer than tether 114. The stiffness of the combination of second medical component 122 and tether 114 may be greater than, equal to or less than the stiffness of the region of medical component 110 distal to the distal region of an arm 102. Such second medical components 122 may be slidably present over any flexible string or tether 114 disclosed herein.

While some variations of medical system 100 comprises a tether 114 that has little column strength (essentially used to pull the device), alternate variations of tether 114 include a wire-like member having a sufficient stiffness that allows for improved control of an end of a medical component 110 that is coupled to tether 114.

FIG. 6L illustrates a second variation of a medical system 100 according to the present invention. In this variation, a second medical component 122 is advanced over tether 114 of the medical component 110. Second medical component 122 may comprise any number of medical devices as described herein. In the illustrated variation, second medical component 122 comprises a catheter tube having working elements 112 such as mapping electrodes. As noted above, second medical component 122 can be coupled to any number of auxiliary sources to deliver fluid (such as saline or a contrast agent), provide suction, deliver additional medical devices/components, or provide visualization.

FIG. 6L also illustrates an example of the medical component 110 and second medical component 122 having respective mating portions 148 and 150. When the medical component 110 and second medical component 122 are advanced together, the mating portions 148 and 150 couple together allowing for the combination of medical component 110 and second medical component 122 to behave as a single unitary device as shown in FIG. 6M. Medical component 110 and second medical component 122 and the mating portions 148 and 150 maybe be designed to ensure a smooth transition of the outer surface of medical component 110 and second medical component 122 when the mating portions 148 and 150 couple together. In one embodiment, mating portion 148 comprises a tapering region and mating portion 150 comprises a hollow region. In the illustrated embodiment, medical component 110 comprises a microwave ablation device with electrodes 118.

In one embodiment, the crossectional profile of integral tether 114 is smaller than the crossectional profile of the rest of medical component 110. Thus the loop formed in the target anatomy by medical component 110 beyond the distal ends of arms 102 is asymmetric—having a slimmer tether 114 and a thicker rest of the medical component 110. In this embodiment, second medical component 122 comprises a hollow region adapted to slide over tether 114. When medical component 110 and second medical component 122 are advanced together with a force, the mating portions 148 and 150 couple together allowing for the combination of medical component 110 and second medical component 122 to behave as a single unitary device. Similarly, when the coupled medical component 110 and second medical component 122 are pulled apart with a force, the mating portions 148 and 150 decouple. In an embodiment, the coupling force is substantially the same as the decoupling force.

As shown in FIG. 6M, the coupled medical component 110 and second medical component 122 can advance between adjacent arms 102 in a similar manner as a single unitary device. Naturally, additional variations of medical system 100 described herein can include a single medical component 110 extended between adjacent arms 102 (as shown in FIG. 6N). In such a case, the medical component 110 can extend fully through arms 102 and exit at the proximal portions of arms 102. Alternatively, one or more ends of the medical component 110 can terminate inside the arms 102 so that medical component 110 does not need to extend through the entirety of both arms 102. In one embodiment, medical component 110 of FIG. 6N comprises one or more working elements. Examples of such working elements include, but are not limited to diagnostic electrodes (e.g. mapping electrodes), ablating elements (radiofrequency ablation electrodes, microwave ablation antennas, cryogenic ablation elements, laser ablation elements, thermal ablation elements, high intensity ultrasound ablation elements, etc.)

Figure 6O:
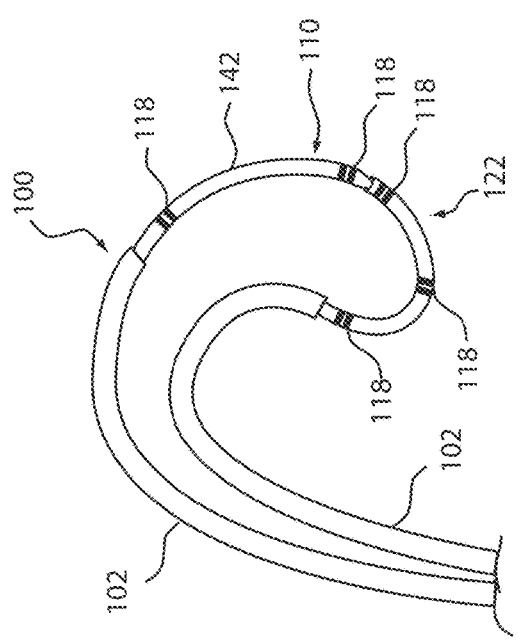
FIGS. 6O-6P illustrate a medical system comprising a medical component comprising a flexible tether and a joint member coupling the tether to the medical component.

A joint member may be used to mechanically couple tether 114 to medical component 110. Generally, the joint member allows for increased articulation between flexible tether 114 and medical component 110. This permits the medical component 110 and tether 114 to form a smaller angle between the joint member 152 and the medical component than would otherwise be attainable given a flexible tether 114. Basically, such a "V" configuration allows for the medical component 110 and tether 114 (or other component that is joined to medical component 110) to be inserted into a smaller opening or passage including, but not limited to: coronary sinus and a lumen of any of the anatomical systems (e.g. cardiovascular, gastrointestinal, etc.) disclosed herein. In some cases, the components joined by joint member 152 can be placed parallel to each other (as shown in FIG. 6O). Joint member 152 can be a flexible joint or it can simply be a "string-like" structure that allows for the joined medical components to be connected but easily positioned into the "V" configuration.

In some circumstances, a physician needs the ability to temporarily use a joint member. For example, a joint member may be useful when advancing the medical components to a target site using a narrow profile (as shown in FIG. 6O), but not desired or needed when the components are positioned at the target site. Accordingly, in some variations of medical system 100, one or more of the components are moveable relative to the joint member to cover the joint member. In one embodiment, tether 114 is axially moveable relative to the joint member. When joint member is covered by tether 114, medical component 110 mechanically couples to second medical component 122 through tether 114. When joint member is uncovered by tether 114, medical component 110 mechanically couples to a second medical component 122 through more flexible joint member. In this configuration, medical component 110 and second medical component 122 can be advanced in the target area in the "V" configuration (as shown in FIG. 6O).

Figure 6P:
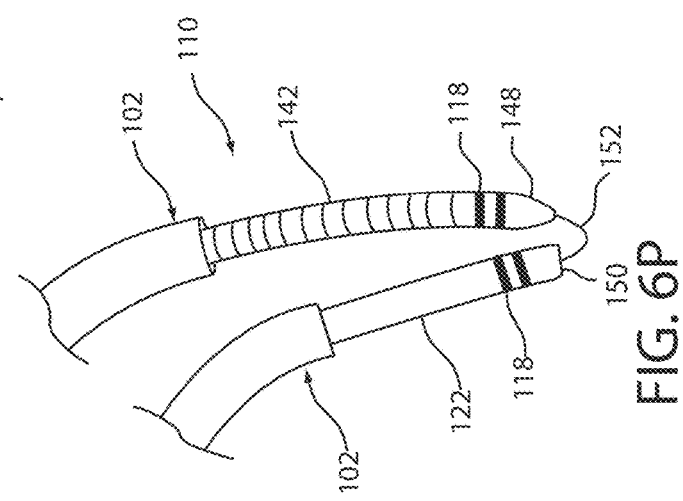

FIG. 6P illustrates a system 100 wherein a medical component 110 is detachably coupled to a second medical component 122 directly through a joint member 152 but without any rail or tether 114. As illustrated, medical component 110 and second medical component 122 can include mating portions 148 and 150 so that upon joining mating portions 148 and 150, joint member 152 is rendered ineffective.

FIGS. 7A-7D show an embodiment of a method to treat an electrophysiological disease like atrial fibrillation in the heart using minimally invasive techniques. The steps shown in FIGS. 7A-7D need not be performed in the sequence as shown in the figures. The performing physician may alter the treatment sequence. Also, all of the steps shown in FIGS. 7A-7D may not be performed during a treatment. One or more steps shown in FIGS. 7A-7D may be omitted and one or more additional steps be added during the treatment by the performing physician.

Figure 6Q:
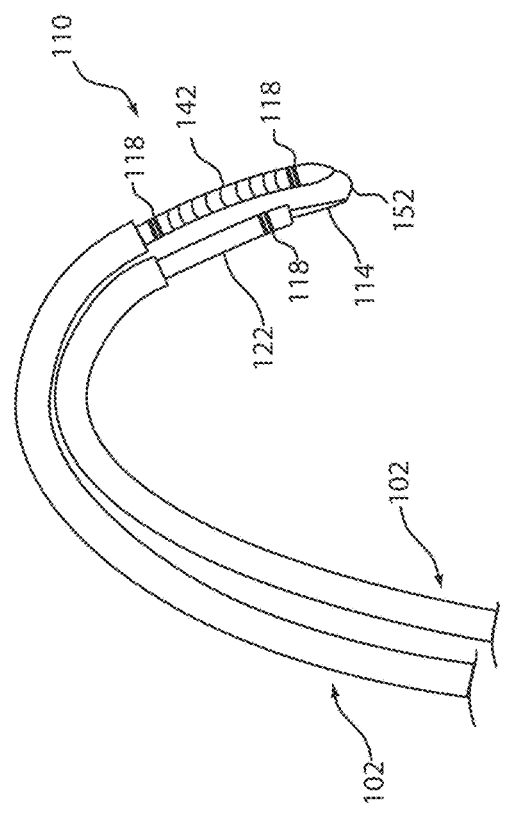
FIG. 6Q shows an embodiment of a medical system similar to the medical system shown in FIG. 6H, but further comprising a hollow second medical component.

The medical system used for the procedure in FIGS. 7A-7D is shown in detail in FIG. 6Q. The medical system shown in FIG. 6Q while being generally similar to the medical system shown in FIG. 6H, further comprises a hollow second medical component 122. Second medical component 122 slides over a tether or spline 114 of medical component 110. In the embodiment shown in FIG. 6Q, second medical component 102 is a mapping sheath comprising a lumen through which one or more fluids such as contrast agents can be introduced into the anatomy. Second medical component 122 may be used to collect electrophysiological information about a disease and/or the outcome of a procedure. Medical component 110 comprises a long, linear active region 142. In one embodiment, active region 142 comprises a microwave antenna that is capable of ablating a long segment of tissue. The distal ends of medical component 110 and second medical component 122 are reversibly attachable in the anatomy. Medical component 110 is introduced through a first arm 102 and second medical component 122 is introduced through a second arm 102. In medical system 100 shown in FIG. 6Q, the distal end of medical component 110 is reversibly attached to the distal end of second medical component 122 forming a "U-mode" configuration.

Figure 7A:
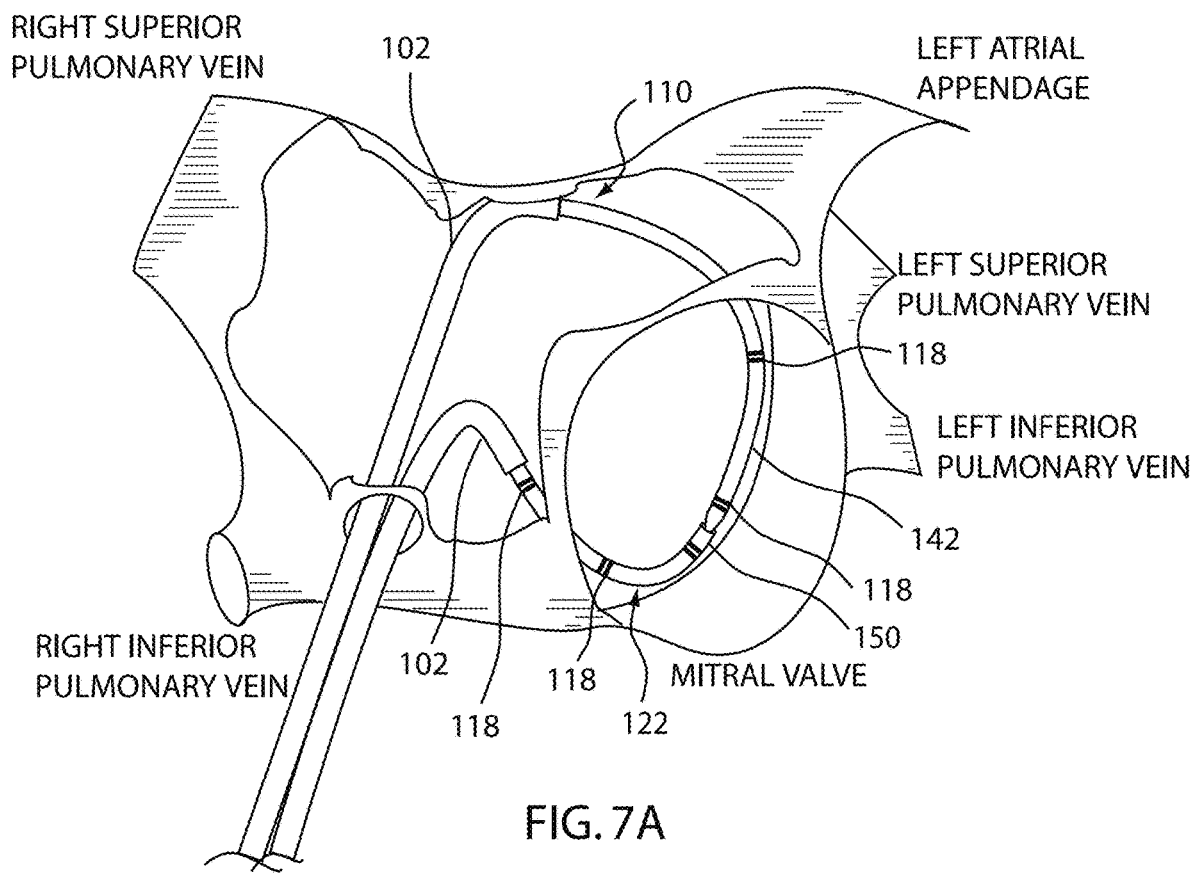
FIGS. 7A-7D show an embodiment of a method to treat an electrophysiological disease like atrial fibrillation in the heart using minimally invasive techniques.

In FIG. 7A, medical system 100 is introduced through an opening into the left atrium (e.g. a trans-septal puncture from the right atrium). Medical system 100 is positioned such that active region 142 of medical system 100 is placed adjoining the left pulmonary vein ostia in the left atrium. In the method embodiment shown in FIG. 7A, the distal end of first arm 102 lies distal to the distal end of second arm 102. Arms 102 may be manipulated by one or more of: torquing one or both arms 102, pulling and/or pushing one or both arms 102, steering the steerable distal end of one or both arms 102. The size and shape of a looped region of medical system 100 can also be further adjusted by advancing and/or withdrawing medical component 110 and/or second medical component 122. Energy (e.g. microwave energy) is applied to ablate a portion of the left atrium adjacent to the left pulmonary vein ostia. In one embodiment, active region 142 creates a long lesion. As with other method embodiments disclosed herein, active region 142 may be repositioned several times to create several long lesions. The lesions are preferably created such that there is substantial overlap between at least two lesions. In one method embodiment, only a single long lesion is created in the region of the left atrium adjacent to the left pulmonary vein ostia.

Medical system 100 may be positioned such that active region 142 is placed adjoining the inferior region of the left atrium. This may be done by positioning the distal ends of medical component 110 and second medical component 122 along the proximal direction i.e. opposite to the direction of introduction of arms 102. In order to achieve this configuration, the distal ends of arms 102 may be designed to deflect more than 90 degrees. Medical system 100 may be positioned such that active region 142 of medical system 100 is placed adjoining the superior region of the left atrium. Thereafter, energy (e.g. microwave energy) is applied to ablate a portion of the left atrium. In one embodiment, active region 142 creates a long lesion.

Figure 7B:
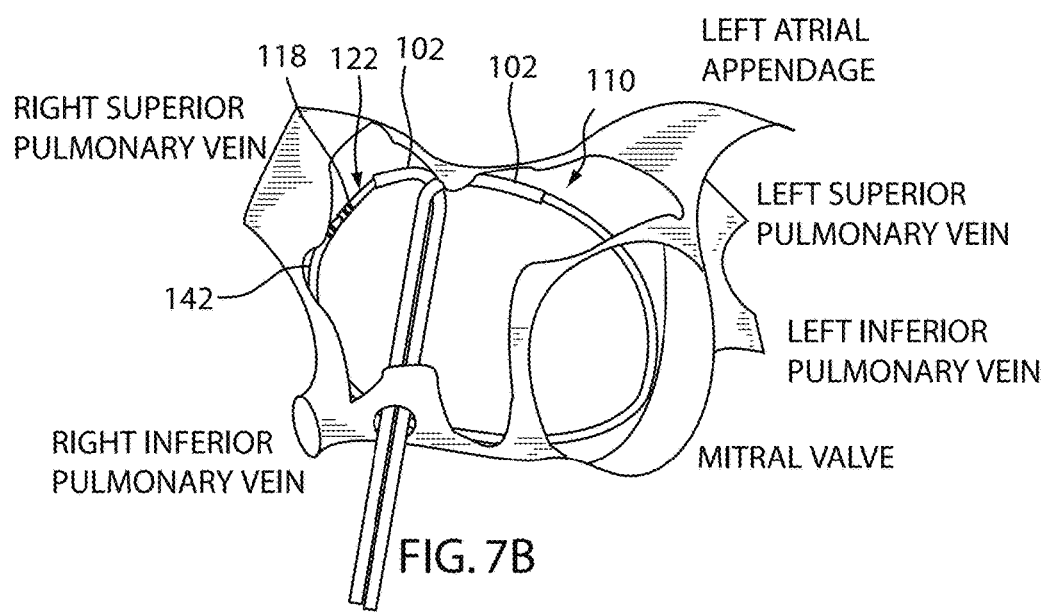

In FIG. 7B, medical system 100 is positioned such that active region 142 of medical system 100 is placed adjoining the right pulmonary vein ostia in the left atrium. As with other method embodiments shown in FIGS. 7A-7D, arms 102 may be further manipulated by one or more of: torquing one or both arms 102, pulling and/or pushing one or both arms 102, steering the steerable distal end of one or both arms 102. The size and shape of a looped region of medical system 100 can also be further adjusted by advancing and/or withdrawing medical component 110 and/or second medical component 122. Thereafter, energy (e.g. microwave energy) is applied to ablate a portion of the left atrium adjacent to the right pulmonary vein ostia.

Figure 7C:
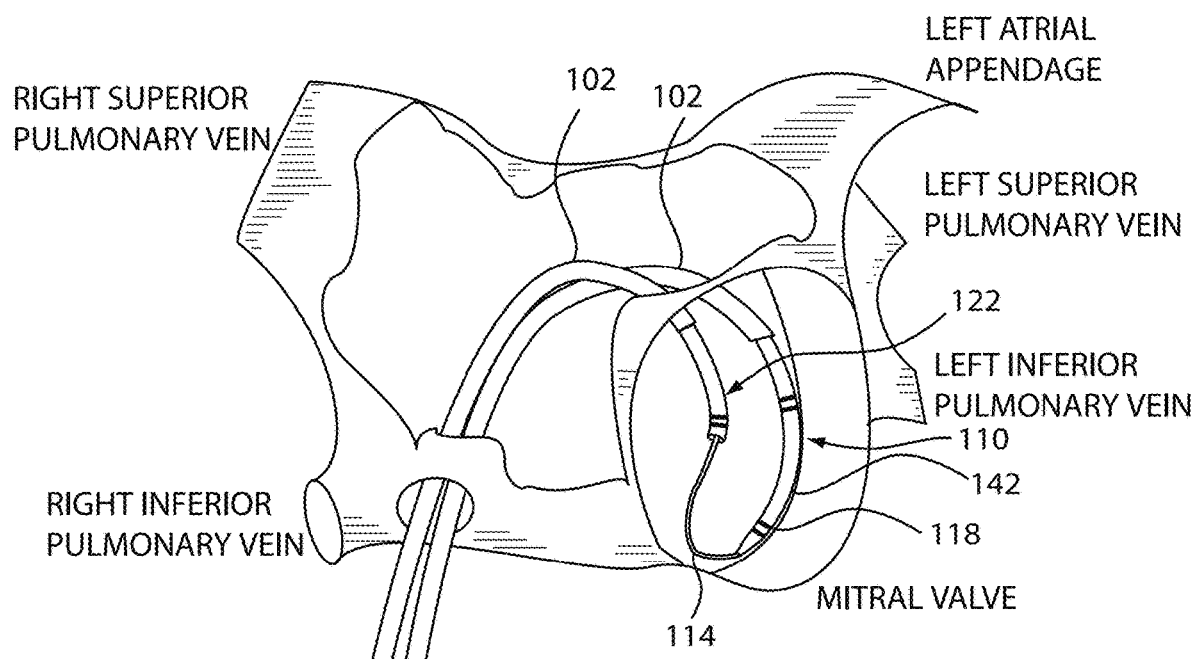

In FIG. 7C, medical system 100 is positioned such that active region 142 of medical system 100 is placed adjoining the region between an ostium of the inferior left pulmonary vein and the mitral valve annulus of the left atrium. In medical system 100 shown in FIG. 7C, the distal end of medical component 110 is detached from the distal end of second medical component 122 forming a V-mode. In one method embodiment, the position of active region 142 is changed from that in FIG. 7A to that in FIG. 7C by pulling apart the distal end of medical component 110 from the distal end of second medical component 122 and pushing second arm 102 distally and/or steering the distal end of second arm 102. As with other method embodiments shown in FIGS. 7A-7D, arms 102 may be further manipulated by one or more of: torquing one or both arms 102, pulling and/or pushing one or both arms 102, steering the steerable distal end of one or both arms 102. The size and shape of a looped region of medical system 100 can also be further adjusted by advancing and/or withdrawing medical component 110 and/or second medical component 122. Active region 142 is placed on or near the region between an ostium of the inferior left pulmonary vein and the mitral valve annulus of the left atrium. Thereafter, energy (e.g. microwave energy) is applied to ablate a portion of the left atrium. In one embodiment, active region 142 creates a long lesion. Active region 142 may be repositioned several times to create several long lesions. Multiple lesions may be created using the steps shown in FIG. 7 series such that there is substantial overlap between at least two lesions.

In one method embodiment, a first lesion is created that isolates the posterior region of the heart (having two left pulmonary veins and two right pulmonary veins) from the rest of the heart (having the mitral valve). It should be noted that the first lesion may comprise multiple overlapping lesions e.g. multiple long overlapping lesions. First lesion may be created using the steps shown in FIGS. 7A-7B. Further, a second lesion may be created that extends from first lesion to a region on the mitral valve annulus of the left atrium. It should be noted that second lesion may comprise multiple overlapping lesions e.g. multiple long overlapping lesions. Second lesion may be created using the step shown in FIG. 7C.

Figure 7D:
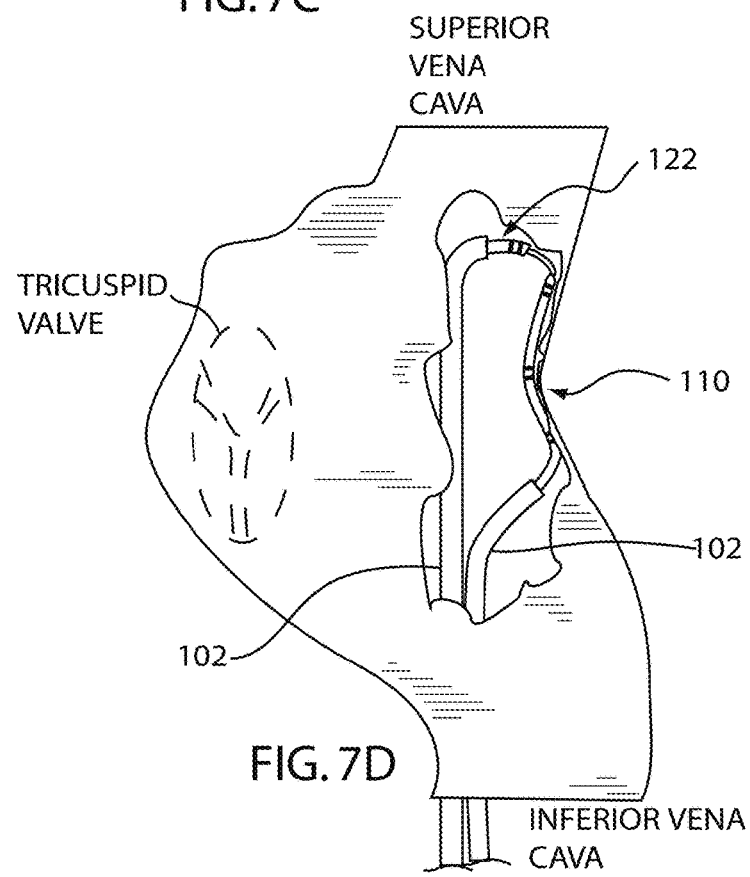

In FIG. 7D, medical system 100 is positioned such that active region 142 of medical system 100 is placed in the right atrium between a region of the superior vena cava and a region of the inferior vena cava. In the configuration of medical system 100 shown in FIG. 7D, the distal end of medical component 110 is detached from the distal end of second medical component 122 forming a V-mode. As with other method embodiments, arms 102 may be further manipulated by one or more of: torquing one or both arms 102, pulling and/or pushing one or both arms 102, steering the steerable distal end of one or both arms 102. The size and shape of a looped region of medical system 100 can also be further adjusted by advancing and/or withdrawing medical component 110 and/or second medical component 122. The combination of arm 102 and second medical component 122 may be used to push active region 142 to contact the target tissue. Thereafter, energy (e.g. microwave energy) is applied to ablate a portion of the right atrium. In one embodiment, active region 142 creates a long lesion. Active region 142 may be repositioned several times to create several long lesions. The lesions are preferably created such that there is substantial overlap between at least two lesions. In one method embodiment, only a single long lesion is created in the right atrium between a region of the superior vena cava and a region of the inferior vena cava. In another method embodiment, a first superior long lesion and a second inferior long lesion are created in the right atrium between a region of the superior vena cava and a region of the inferior vena cava such that the first superior long lesion and the second inferior long lesion overlap.

In one method embodiment, a third lesion is created that extends from the tricuspid valve annulus to a region of the inferior vena cava inferior to the tricuspid valve annulus. It should be noted that third lesion may comprise multiple overlapping lesions e.g. multiple long overlapping lesions. Further, a fourth lesion may be created that extends between a region of the superior vena cava and a region of the inferior vena cava. It should be noted that fourth lesion may comprise multiple overlapping lesions e.g. multiple long overlapping lesions. Fourth lesion may be created using the step shown in FIG. 7D.

Although FIGS. 7A-7D mostly disclose the use of devices and methods for creating long linear lesions, various devices and methods of FIGS. 7A-7D may be designed to create point lesions, long curvilinear lesions, lesions covering an area of tissue and lesions covering a volume of tissue. Two or more of such lesions may overlap. When such lesions are created in the heart, one or more of the lesions disclosed herein may be transmural. One or more of the devices and methods disclosed herein may be used to perform variations of the Maze procedure to treat atrial fibrillation. Further, any suitable medical system 100 disclosed herein may be used to perform any of the method steps disclosed herein (e.g. method steps shown in FIGS. 7A-7D) and/or create any of the lesions disclosed herein. Thus medical system 100 of FIG. 6Q is advantageous over current systems that do not allow easy access to all regions of the left atrium and do not allow the positioning of points and/or segments of medical system 100 at any desired orientation on the inner surface of the left atrium. For example, with current radiofrequency ablation systems for treating atrial fibrillation, it is difficult to access the area around the right pulmonary veins in the left atrium and create multiple overlapping lesions.

Several alternate embodiments of lesions patterns and methods are possible with the present invention. For example, FIG. 7E shows a view of an example of a lesion pattern created in the left atrium using the medical system 100 similar to medical system 100 in FIG. 4C or FIG. 1AA to treat atrial fibrillation. The figure shows a first left pulmonary vein lesion 164 and a second left pulmonary vein lesion 166 that together electrically isolate the left pulmonary veins of the heart from the rest of the heart. First left pulmonary vein lesion 164 and second left pulmonary vein lesion 166 overlap at at least two regions. The figure also shows a first right pulmonary vein lesion 168 and a second right pulmonary vein lesion 170 that together electrically isolate the right pulmonary veins of the heart from the rest of the heart. First right pulmonary vein lesion 168 and a second right pulmonary vein lesion 170 overlap at at least two regions. It should be noted that lesions 164, 166, 168, 170 may comprise multiple overlapping lesions e.g. multiple long overlapping lesions.

Figure 7F:
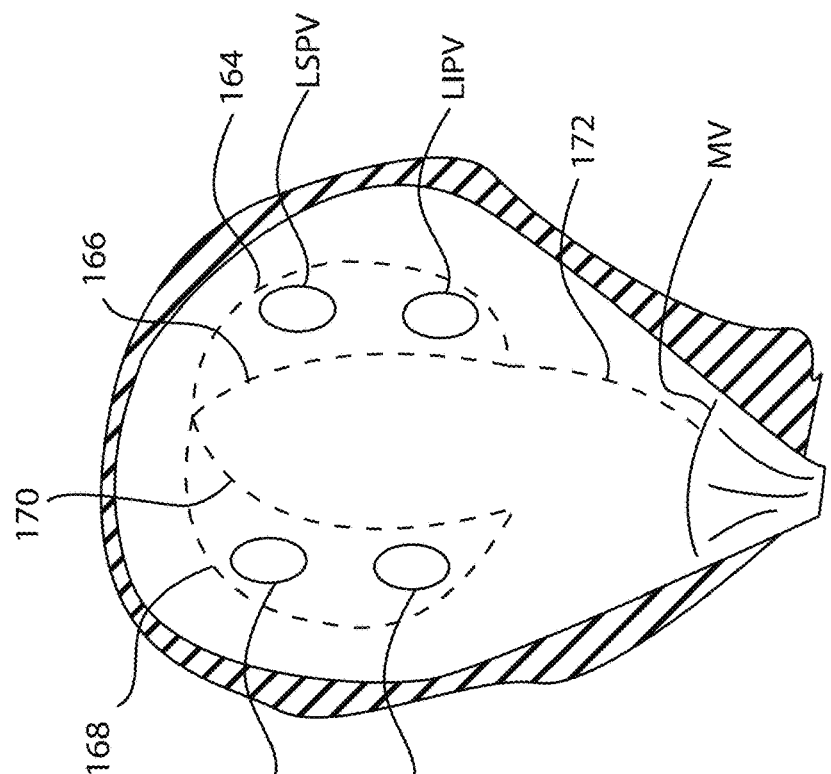
FIGS. 7E and 7F show examples of lesion patterns created in the left atrium using a medical system similar to the medical system in FIG. 4C to treat atrial fibrillation.
Figure 7E:
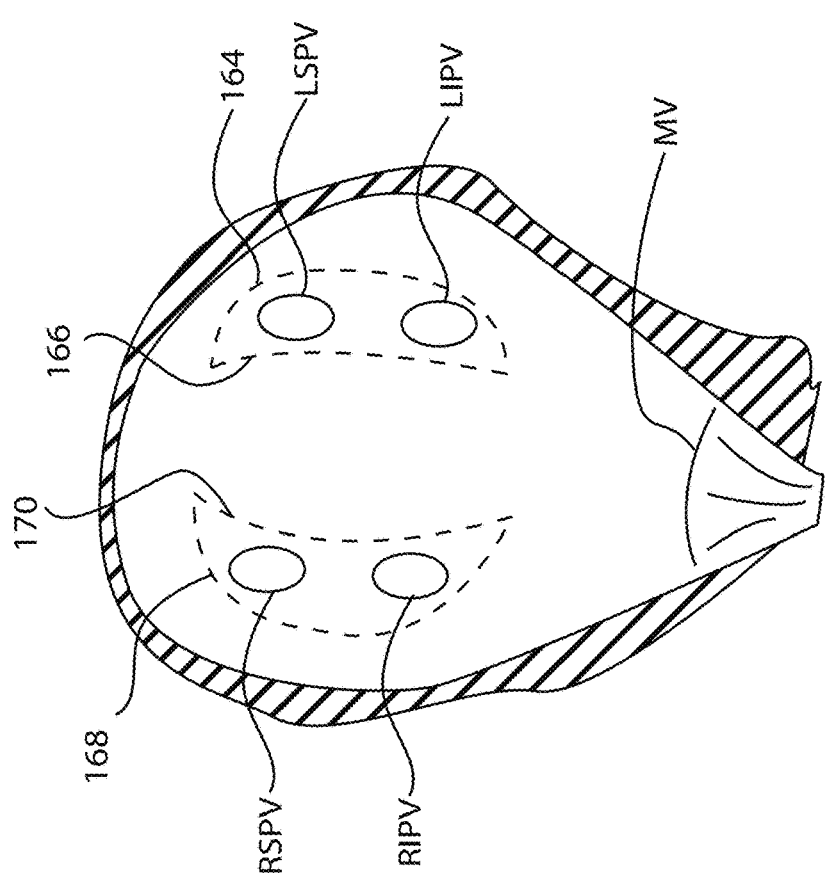

FIG. 7F shows a view of an alternate lesion pattern created in the left atrium using the medical system 100 similar to medical system 100 in FIG. 4C or FIG. 1AA to treat atrial fibrillation. The figure shows a first left pulmonary vein lesion 164, a second left pulmonary vein lesion 166, a first right pulmonary vein lesion 168 and a second right pulmonary vein lesion 170 similar to those in FIG. 7E. Further, one of first left pulmonary vein lesion 164 and second left pulmonary vein lesion 166 overlaps with one of first right pulmonary vein lesion 168 and a second right pulmonary vein lesion 170. The lesion pattern further comprises a mitral valve lesion 172 that connects a region of the mitral valve annulus to one of first left pulmonary vein lesion 164 and second left pulmonary vein lesion 166. It should be noted that lesions 164, 166, 168, 170 and 172 may comprise multiple overlapping lesions e.g. multiple long overlapping lesions.

Figures 7G, 7H:
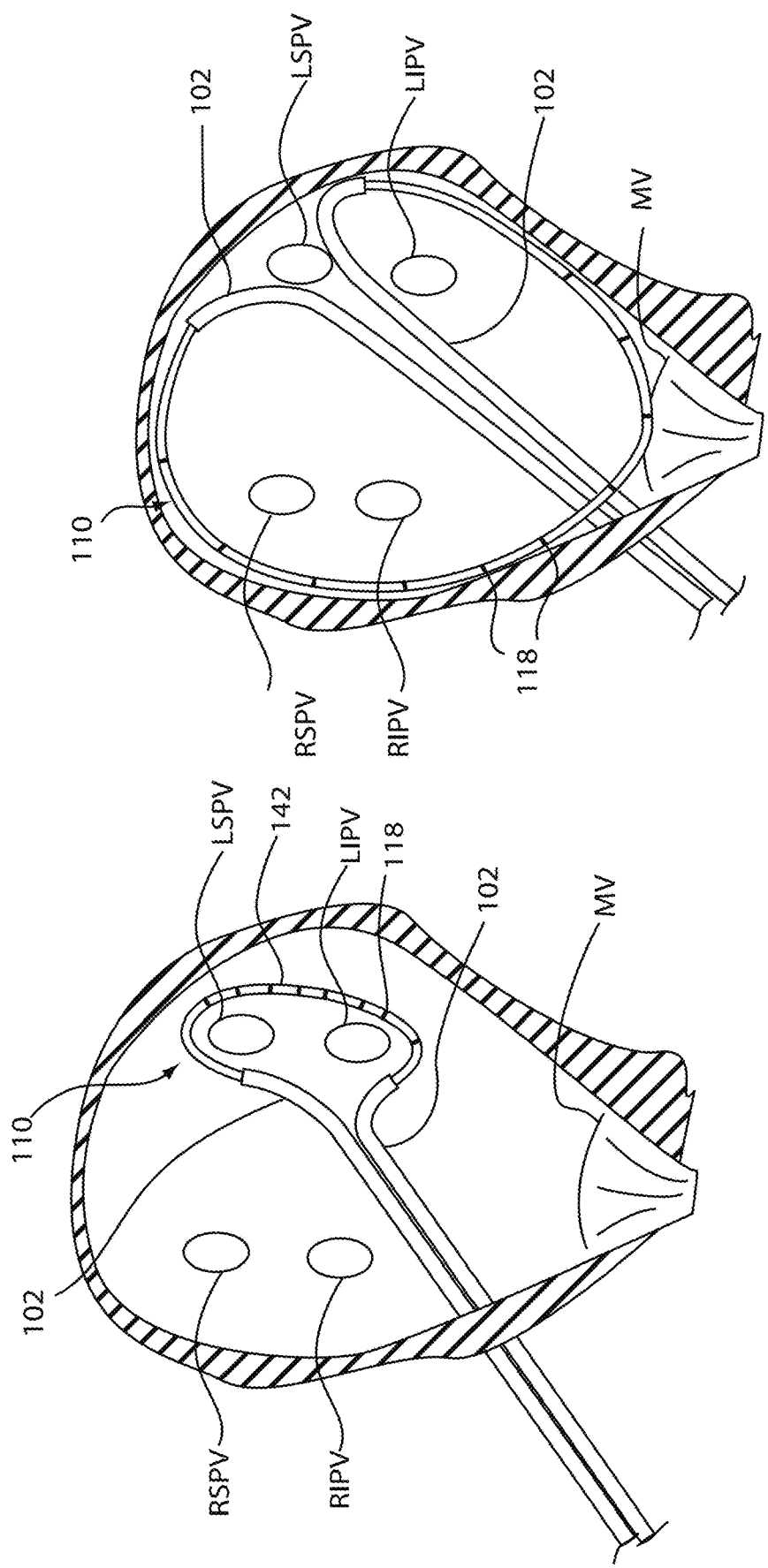
FIG. 7G show a step in the creation of the lesion pattern shown in FIG. 7E.
FIG. 7H shows an embodiment of medical system deployed inside the left atrium such that a medical component substantially spans the entire left atrium.

FIG. 7G show a step in the creation of the lesion pattern as shown in FIG. 7E. In FIG. 7N, a medical system 100 e.g. medical system 100 in FIG. 4C or FIG. 1AA is positioned in the left atrium such that a region of medical component 110 is positioned anterior to the left pulmonary veins as shown. Thereafter, one or more lesions are created anterior to the left pulmonary veins. Medical system 100 may be repositioned in the left atrium such that a region of medical component 110 is positioned posterior to the left pulmonary veins. Thereafter, one or more lesions are created posterior to the left pulmonary veins such that the lesions created in this step overlap with the lesions created previously in the step in FIG. 7N. Thereafter, medical system 100 may be repositioned in the left atrium to create one or more lesions posterior to the left pulmonary veins and anterior to the right pulmonary veins as shown. The steps of repositioning medical system 100 can be made using any of the steps and devices disclosed elsewhere in the specification.

In any of the embodiments disclosed herein, a looped medical component 110 and/or looped second medical component 122 may be deployed in an anatomical region such that the looped medical component 110 and/or looped second medical component 122 substantially span the entire anatomical region. In one method embodiment, this is done by deploying arms 102 in the anatomical region with a looped medical component 110 and/or looped second medical component 122 connecting the distal regions of arms 102. Thereafter, looped medical component 110 and/or looped second medical component 122 are expanded in the anatomical region till looped medical component 110 and/or looped second medical component 122 substantially span the entire anatomical region. For example, FIG. 7H shows an embodiment of medical system 100 deployed inside the left atrium such that looped medical component 110 substantially spans the entire left atrium.

Although a significant amount of the disclosure discloses various embodiments of medical systems 100 used for treating regions of the heart, any device embodiment described herein may also be used to treat other anatomical regions. The devices and methods disclosed herein are especially suited for minimally invasive surgery inside hollow organs, openings or lumens. Examples of such lumens include, but are not limited to lumens in the vasculature, lumen of the gastrointestinal tract, lumens in the mouth or other oropharyngeal regions and lumens in the respiratory system. Medical system 100 may be collapsed for introduction through narrow passages or openings. Embodiments of medical system 100 may be used to ablate tissue inside or around the coronary sinus. In a particular embodiment medical system 100 is used in the V-mode to ablate tissue inside a coronary sinus.

Medical system 100 comprising one or more arms 102 and medical component 110 may be introduced non-invasively into the lower esophagus through the nose or mouth to destroy Barrett's tissue. The position and/or the orientation of one or more regions of medical system 100 is tracked using an endoscope. The position and/or the orientation of one or more regions of medical system 100 can also be tracked using fluoroscopy, ultrasound or other imaging modalities disclosed herein. Medical component 110 comprising an active region 142 is manipulated such that active region 142 is adjacent to or in contact with the target tissue. Thereafter, active region 142 is used to treat tissue. The treatment may be tracked using endoscope and/or fluoroscopy or other imaging modalities disclosed herein. After a first region of target tissue is treated, active region 142 may be moved to a second region. The repositioning can be made by any one of the methods disclosed herein. More specifically, active region 142 may be rotated circumferentially along the esophagus or moved along the length of the esophagus. Medical component 110 may be deployed in a helical or spiral configuration inside the esophagus. In one embodiment, medical component 110 has a pre-shaped region that enables medical component to achieve such a helical or spiral configuration. In another embodiment, medical component 110 is twisted by twisting or torquing one of arms 102 such that medical component 110 achieves such a helical or spiral configuration.

Medical system 100 comprising one or more arms 102 and medical component 110 may be introduced non-invasively into the uterus through the vagina and the cervix for endometrial ablation. The position and/or the orientation of one or more regions of medical system 100 may be tracked using an external ultrasound device. The position and/or the orientation of one or more regions of medical system 100 can also be tracked using fluoroscopy, hysteroscopy, transvaginal ultrasound or any other imaging modalities disclosed herein. Arms 102 may have one or more distance markers along the length of arms 102 to indicate the depth of insertion of arms 102 into the uterine cavity. Active region 142 may be positioned inside the uterus and oriented perpendicular to the path of insertion of arms 102. In one embodiment, the configuration of medical system 100 is similar to the configuration of medical system 100 in FIG. 4C. After a first region of target tissue is destroyed, active region 142 may be moved to a second region and a second region of the endometrium may be ablated. More specifically, active region 142 may be pulled proximally towards the cervix.

Medical system 100 comprising one or more arms 102 and medical component 110 may be introduced non-invasively into the lower esophageal region enclosed by the lower esophageal sphincter through the nose or mouth for treating GERD (Gastroesophageal reflux disease). The method may be similar to the method used for treating Barrett's tissue. Arms 102 may have one or more distance markers along the length of arms 102 to indicate the depth of insertion of arms 102 into the esophagus. In this embodiment, active region 142 is used to deliver energy that causes shrinkage of tissue. Active region 142 may be rotated within the esophagus if needed.

FIGS. 8A and 8B show two embodiments of arm coupling elements 184 that may be used to mechanically couple two or more arms 102 disclosed herein. Such arm coupling elements 184 may be used along with any of the arms 102 in any of the medical systems 100 disclosed herein. In FIG. 8A, an arm coupling element 184 comprises two lumens. A first arm 102 is located within a lumen of arm coupling element 184 and a second arm 102 is located within another lumen of arm coupling element 184. Arm coupling element 184 in this embodiment is made of a sufficiently stiff material such that the lumens of arm coupling element 184 are substantially non-collapsible. The inner lining of any of the lumens of devices herein such as that of arm coupling elements 184 may be lined with a layer of PTFE or other materials to reduce friction. FIG. 8B shows an embodiment of an arm coupling element 184 comprising a non-collapsible lumen 184A and one or more collapsible lumens 184B. Collapsible lumen 184B is substantially collapsed when it does not enclose a device. This allows the reduction of the overall cross sectional profile of arm coupling element 184. In one embodiment, an arm 102 is introduced through non-collapsible lumen 184A. Thereafter, if needed, a second arm 102 is introduced through collapsible lumen 184B. Such a design comprising one or more collapsible lumens may be used to design any of the arms 102 disclosed herein. In such embodiments, a portion of medical component 110 may pass through a lumen of arm 102 and one or more portions of medical system 100 may pass through the one or more collapsible lumens.

FIG. 9A shows another example of a system 100 where a second medical component 122 advances over a medical component 110. Second medical component 122 is introduced through a first arm 102 and medical component 110 is introduced through second arm 102. In the illustrated variation second medical component 122 is an energy delivery catheter and medical component 110 comprises a tether or rail. As noted herein, the system 100 can be used with any number of medical components. In the illustrated variation, second medical component 122 comprises an energy transfer device having an active region 142 along with one or more additional working elements 112. Examples of working elements 112 are disclosed elsewhere in the specification. In one embodiment, working elements 112 are selected from the group comprising of one or more: radiofrequency electrodes (monopolar or bipolar), mapping electrodes, DC resistive heating sources, microwave antennas, ultrasound energy transfer elements, laser sources and cryogenic elements.

As shown, the second medical component 122 can advance over the medical component 110 which functions as a rail, guide, or tether. In such a case, the first and second medical components 110 and 122 comprise separate medical devices. In an alternative variation, the first and second medical components 110 and 122 can be integrated together as a single device where the energy transfer device or component 122 includes a rail or tether that is affixed to a distal end. In such a case, rail or tether can be used to either pull the device through the second arm 102 (as a tether member) or provide sufficient column strength and flexibility to aid in positioning of the active region 142 as desired (as a rail member or flexible tether).

FIG. 9A also illustrates the use of an optional third arm 102 that is coupled to either medical component 110 or second medical component 122. In the illustrated variation, third arm 102 comprises a grasping structure 178 used to removably engage either of medical component 110 or second medical component 122. Third arm 102 allows a physician with another means of positioning medical component 110 and/or second medical component 122 to perform the desired procedure. Grasping structure 178 allows third arm 102 to be introduced into or removed from the operative space at any point during the procedure. Any number of grasping mechanisms can be employed including hooks, rings, grasping jaws, etc. Instead of a third arm 102, any other accessory positioning device such as a magnetic device may be used to position medical component 110 and/or second medical component 122.

FIG. 9B illustrates a variation of a system 100 under the present invention where the medical component 110 is coupled adjacent to the arms 102 via coupling portions 180 rather than being introduced through the arms as shown in some of the previous figures. As noted above, coupling portions 180 can comprise ring or tube structures. Alternatively, the coupling portions 180 can consist of a grasping mechanism such as grasping structure 178 discussed above. In this variation, medical component 110 comprises an energy transfer region 142.

Figure 10B:
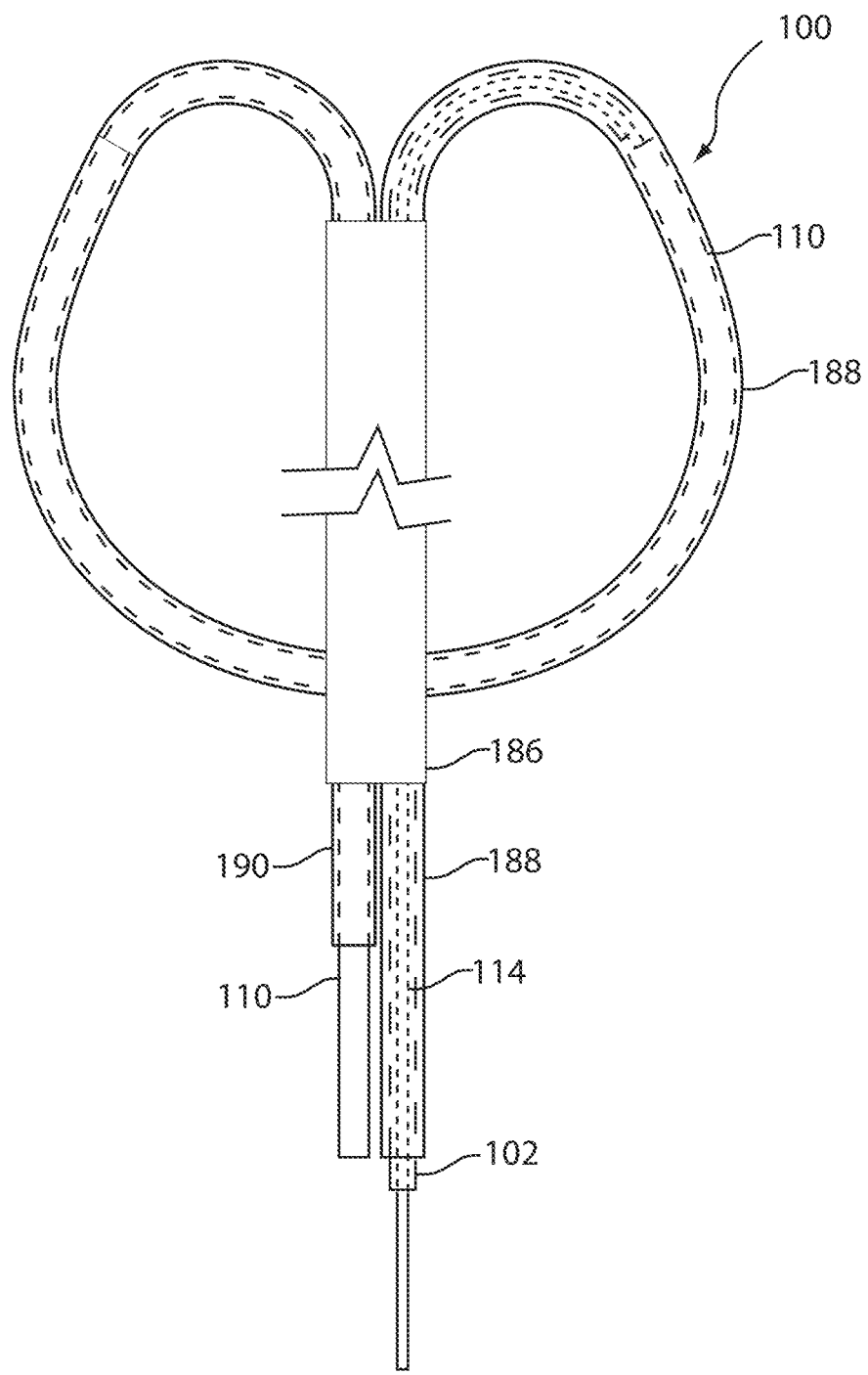

FIGS. 10A-10DA show various views of a first embodiment of a medical system comprising a hollow tube through which an elongate looped medical component is slidably introduced. FIG. 10A shows a side view of a medical system 100 comprising an introducer sheath 186. Introducer sheath 186 encloses a lumen through which an elongate functional tube 188 is introduced. Any functional tube 188 disclosed herein may comprise one or more working elements 112. In one embodiment, functional tube 188 comprises one or more mapping electrodes. In an alternate embodiment, functional tube 188 does not comprise any functional elements 112. Any functional tube 188 disclosed herein may be porous or non-porous. Functional tube 188 is looped such that the two ends of functional tube 188 pass through introducer sheath 186 and exit through the proximal end of introducer sheath 186. One or both of the two ends of functional tube 188 may be advanced and/or retracted and/or torqued or twisted to position functional tube 188 as desired in the anatomy. The looped region of functional tube 188 distal to the distal end of introducer sheath 186 may be twisted or turned or otherwise distorted. The size of the looped region of functional tube 188 distal to the distal end of introducer sheath 186 may be increased or decreased as needed. In the embodiment shown in FIG. 10A, functional tube 188 comprises an integral steering mechanism 190 integral to a portion of functional tube 188.

In one embodiment as shown in FIG. 10A, integral steering mechanism 190 is a pre-shaped, sufficiently rigid portion of functional tube 188. In another embodiment, integral steering mechanism comprises one or more displaceable elements such as pull wires, tethers, stylets, etc. Integral steering mechanism 190 may be used to further manipulate the section of functional tube 188 enclosed by integral steering mechanism 190. Functional tube 188 encloses a medical component 110 comprising an active region 142. Medical component 110 is slidably located within functional tube 188. In the embodiment shown in FIG. 10A, medical component 110 comprises a tether 114. Medical component 110 may be pulled and/or pushed and/or torqued or twisted to position medical component 110 relative to functional tube 188. In one embodiment, manipulation of medical component 110 leads to a change in the position and/or orientation of one or more portions of functional tube 188. In another embodiment, manipulation of medical component 110 does not change the position and/or orientation of one or more portions of functional tube 188. Medical system 100 further comprises an arm 102 located within functional tube 188. Arm 102 comprises a lumen that encloses tether 114 of medical component 110. Arm 102 is slidably positioned relative to tether 114. Arm 102 may be advanced and/or retracted and/or torqued or twisted to position functional tube 188 as desired in the anatomy. Further, arm 102 may comprise a steering modality to further position functional tube 188. Examples of such steering modalities are disclosed elsewhere in the specification. In one embodiment, medical component 110 is a microwave ablation catheter and functional tube 188 is designed such that microwave energy passes through functional tube 188 to ablate surrounding anatomical regions. In this embodiment, working elements 112 on functional tube 188 are designed such that they do not substantially interfere with the microwave energy emitted by medical component 110. In the embodiment in FIG. 10A, one or more regions of medical component 110 may be positioned in the anatomy by one or more of: pulling or releasing tether 114; pulling and/or pushing and/or torquing or twisting medical component 110; advancing and/or retracting and/or torquing or twisting one or both of the two ends of functional tube 188; engaging integral steering mechanism 190; engaging a steering mechanism on arm 102; advancing and/or withdrawing and/or torquing or twisting arm 102 and advancing and/or withdrawing and/or torquing or twisting introducer sheath 186. One or more regions of medical component 110 may be repositioned as needed to access and treat one or more anatomical regions. In one embodiment shown in FIG. 10B, integral steering mechanism 190 and arm 102 are manipulated such that a portion of functional tube 188 extends in the proximal direction proximal to the distal end of introducer sheath 186. In FIG. 10B, a portion of functional tube 188 lies adjacent to or in contact with a portion of introducer sheath 186 proximal to the distal end of introducer sheath 186.

FIG. 10C shows a cross sectional view through the medical system of FIG. 10A through plane 10C-10C. FIG. 10C shows introducer sheath 186 enclosing two segments of functional tube 188. One of the segments of functional tube 188 comprises integral steering mechanism 190 in the form of a sufficiently stiff, bent or pre-shaped region of functional tube 188. This segment of functional tube 188 encloses medical component 110. The other of the segments of functional tube 188 encloses arm 102 which in turn encloses tether 114. FIG. 10D shows a cross sectional view through the medical system of FIG. 10A through plane 10D-10D. FIG. 10DA shows a cross sectional view through the medical system of FIG. 10A through plane 10DA-10DA.

FIGS. 10E-10HA show various views of a second embodiment of a medical system comprising a hollow tube through which an elongate looped medical component is slidably introduced. In FIG. 10E, introducer sheath 186 encloses a lumen through which an elongate functional tube 188 is introduced. Functional tube 188 is looped such that the one end of functional tube 188 passes through introducer sheath 186 and exits through the proximal end of introducer sheath 186. The other end of functional tube 188 terminates outside introducer sheath 186 and is located adjacent to the distal end of introducer sheath 186. The end of functional tube 188 passing through introducer sheath 186 may be advanced and/or retracted and/or torqued or twisted to position functional tube 188 as desired in the anatomy. The looped region of functional tube 188 distal to the distal end of introducer sheath 186 may be twisted or turned or otherwise distorted.

The size of the looped region of functional tube 188 distal to the distal end of introducer sheath 186 may be increased or decreased as needed. In the embodiment shown in FIG. 10E, a first arm 102 comprising a steering mechanism is slidably positioned over a portion of functional tube 188 distal to the distal end of introducer sheath 186. First arm 102 may be pre-shaped and have sufficient rigidity to manipulate a portion of functional tube 188. In another embodiment, first arm 102 comprises one or more displaceable steering elements such as pull wires, tethers, stylets, etc. First arm 102 may be used to further manipulate the section of functional tube 188 enclosed by first arm 102. Functional tube 188 encloses a medical component 110 comprising an active region 142. Medical component 110 is slidably located within functional tube 188. In the embodiment shown in FIG. 10E, medical component 110 comprises a tether 114.

Medical component 110 may be pulled and/or pushed and/or torqued or twisted to position medical component 110 relative to functional tube 188. In one embodiment, manipulation of medical component 110 leads to a change in the position and/or orientation of one or more portions of functional tube 188. In another embodiment, manipulation of medical component 110 does not change the position and/or orientation of one or more portions of functional tube 188. Medical system 100 further comprises a second arm 102 located within functional tube 188. Second arm 102 comprises a lumen that encloses tether 114 of medical component 110. Second arm 102 is slidably positioned relative to tether 114. Second arm 102 may be advanced and/or retracted and/or torqued or twisted to position functional tube 188 as desired in the anatomy. Further, second arm 102 may comprise a steering modality to further position functional tube 188. Examples of such steering modalities are disclosed elsewhere in the specification.

Figure 10F:
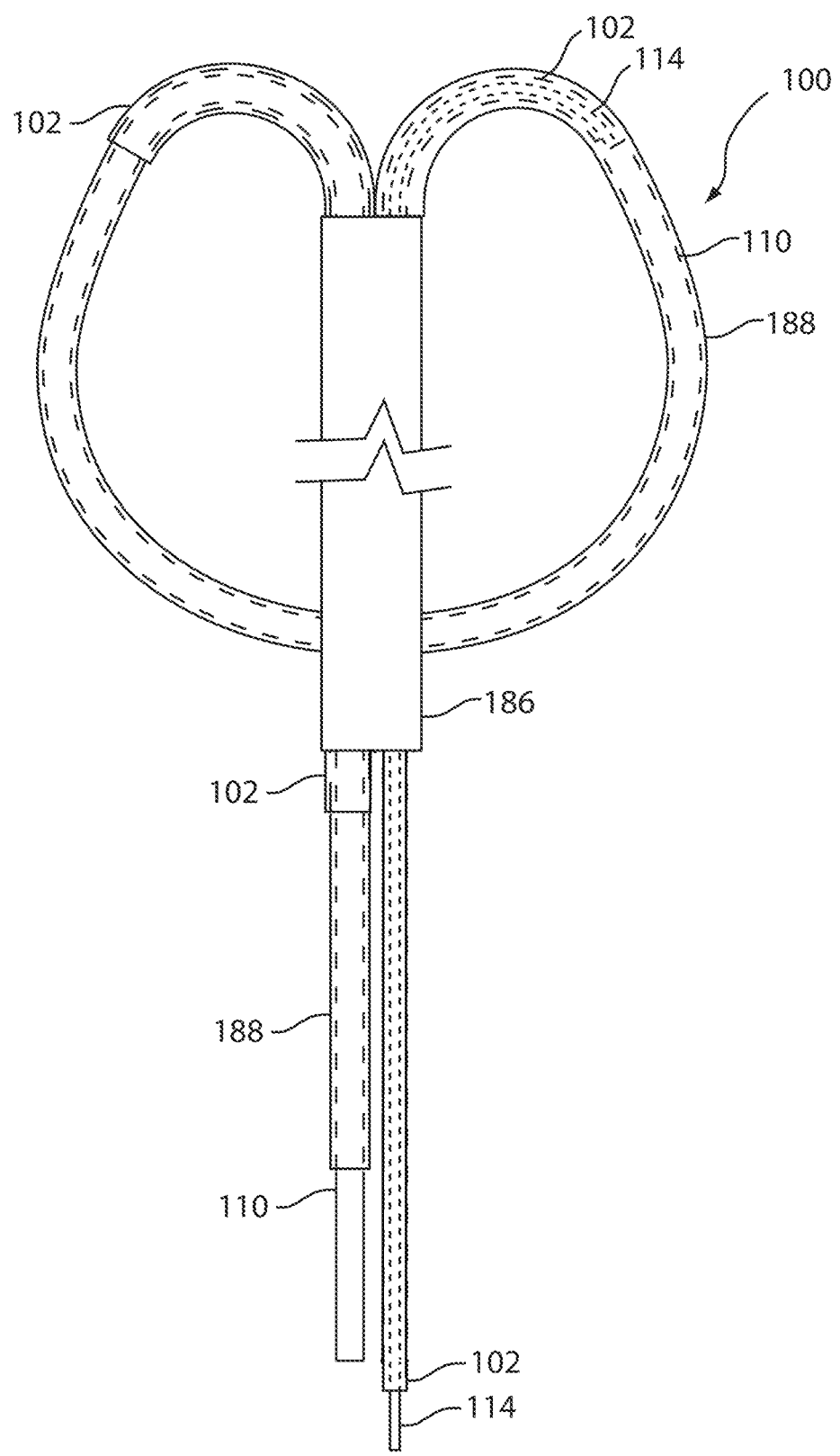

In one embodiment, medical component 110 is a microwave ablation catheter and functional tube 188 is designed such that microwave energy passes through functional tube 188 to ablate surrounding anatomical regions. In this embodiment, working elements 112 on functional tube 188 are designed such that they do not substantially interfere with the microwave energy emitted by medical component 110. In the embodiment in FIG. 10E, one or more regions of medical component 110 may be positioned in the anatomy by one or more of: pulling or releasing tether 114; pulling and/or pushing and/or torquing or twisting medical component 110; advancing and/or retracting and/or torquing or twisting one end of functional tube 188; engaging a steering modality on first arm 102 and/or second arm 102; advancing and/or withdrawing and/or torquing or twisting first arm 102 and/or second arm 102 and advancing and/or withdrawing and/or torquing or twisting introducer sheath 186. One or more regions of medical component 110 may be repositioned as needed to access and treat one or more anatomical regions. In one embodiment shown in FIG. 10F, first arm 102 and second arm 102 are manipulated such that a portion of functional tube 188 extends in the proximal direction proximal to the distal end of introducer sheath 186. In FIG. 10F, a portion of functional tube 188 lies adjacent to or in contact with a portion of introducer sheath 186 proximal to the distal end of introducer sheath 186. FIG. 10G shows a cross sectional view through the medical system of FIG. 10E through plane 10G-10G. FIG. 10G shows two portions of functional tube 188. One of the portions of functional tube 188 is enclosed within first arm 102. This segment of functional tube 188 encloses medical component 110. The other of the segments of functional tube 188 encloses second arm 102 which in turn encloses tether 114. FIG. 10H shows a cross sectional view through the medical system of FIG. 10A through plane 10H-10H. In FIG. 4C, only one segment of functional tube 188 is seen enclosed within introducer sheath 186. FIG. 10HA shows a cross sectional view through the medical system 100 of FIG. 10A through plane 10HA-10HA.

Figures 10I, 10K, 10L:
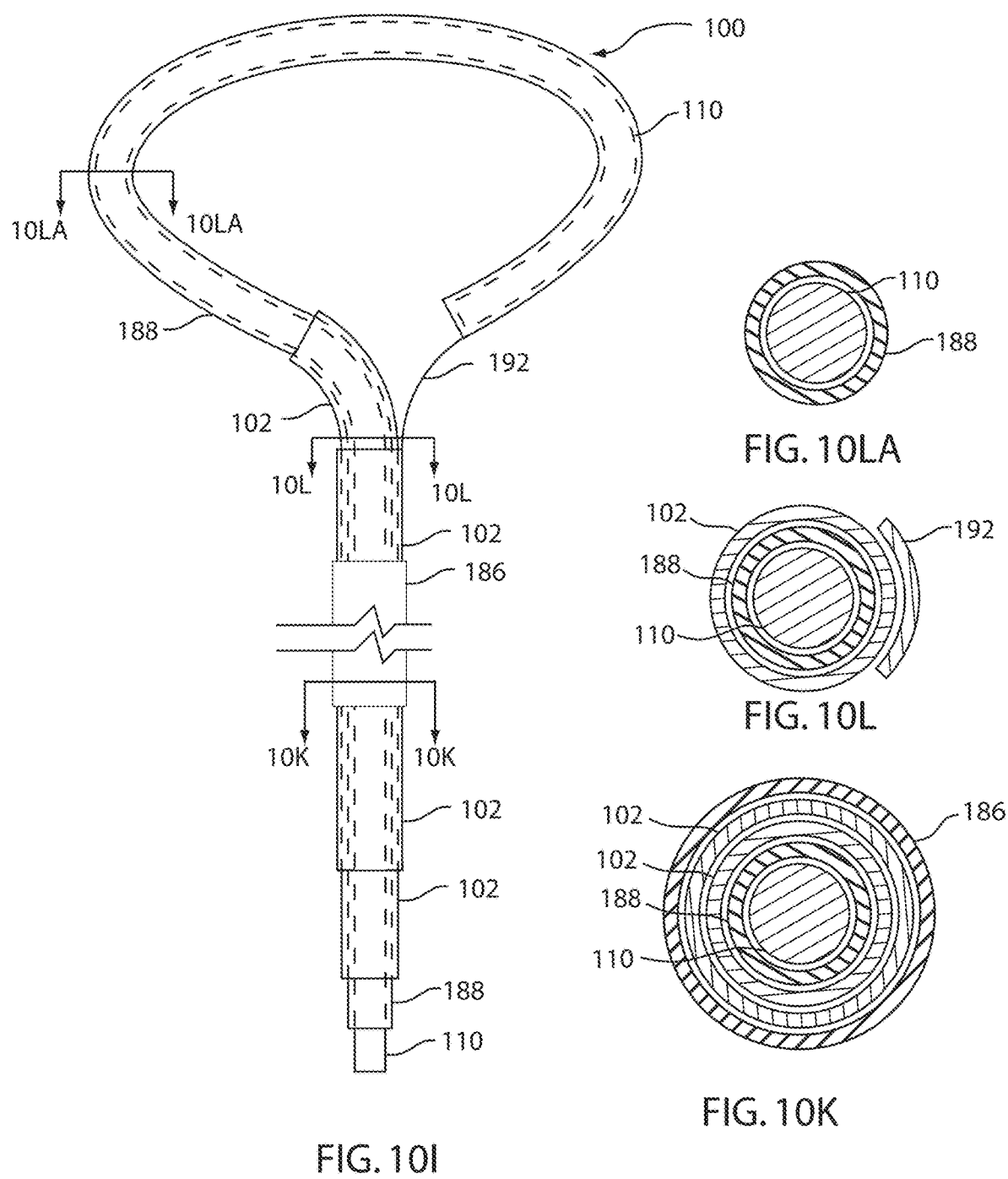
FIGS. 10I-10LA show various views of a third embodiment of a medical system comprising a hollow tube through which an elongate looped medical component is slidably introduced.

FIGS. 10I-10LA show various views of a third embodiment of a medical system comprising a hollow tube through which an elongate looped medical component is slidably introduced. In FIG. 10I, introducer sheath 186 encloses a lumen through which an elongate functional tube 188 is introduced. Functional tube 188 is looped such that the one end of functional tube 188 passes through introducer sheath 186 and exits through the proximal end of introducer sheath 186. The other end of functional tube 188 terminates outside introducer sheath 186 and is located distal to the distal end of introducer sheath 186. The end of functional tube 188 passing through introducer sheath 186 may be advanced and/or retracted and/or torqued or twisted to position functional tube 188 as desired in the anatomy.

The looped region of functional tube 188 distal to the distal end of introducer sheath 186 may be twisted or turned or otherwise distorted. The size of the looped region of functional tube 188 distal to the distal end of introducer sheath 186 may be increased or decreased as needed. In the embodiment shown in FIG. 10I, a first arm 102 comprising a steering mechanism is slidably positioned over a portion of functional tube 188 distal to the distal end of introducer sheath 186. First arm 102 may be pre-shaped and have sufficient rigidity to manipulate a portion of functional tube 188. In another embodiment, first arm 102 comprises one or more displaceable steering elements such as pull wires, tethers, stylets, etc. First arm 102 may be used to further manipulate the section of functional tube 188 enclosed by first arm 102. Functional tube 188 encloses a medical component 110 comprising an active region 142. Medical component 110 is slidably located within functional tube 188. Medical component 110 may be pulled and/or pushed and/or torqued or twisted to position medical component 110 relative to functional tube 188. In one embodiment, manipulation of medical component 110 leads to a change in the position and/or orientation of one or more portions of functional tube 188. In another embodiment, manipulation of medical component 110 does not change the position and/or orientation of one or more portions of functional tube 188.

Medical system 100 further comprises a second arm 102 that encloses first arm 102. Second arm 102 comprises a lumen that encloses first arm 102 which in turn encloses functional tube 188 which in turn encloses medical component 110. Second arm 102 is slidably positioned relative to first arm 102. A distal region of second arm 102 is connected to the distal end of functional tube 188 by a flexible connector 192. Second arm 102 may be advanced and/or retracted and/or torqued or twisted to position functional tube 188 as desired in the anatomy. Further, second arm 102 may comprise a steering modality to further position functional tube 188. Examples of such steering modalities are disclosed elsewhere in the specification. In one embodiment, medical component 110 is a microwave ablation catheter and functional tube 188 is designed such that microwave energy passes through functional tube 188 to ablate surrounding anatomical regions. In this embodiment, working elements 112 on functional tube 188 are designed such that they do not substantially interfere with the microwave energy emitted by medical component 110.

Figure 10J:
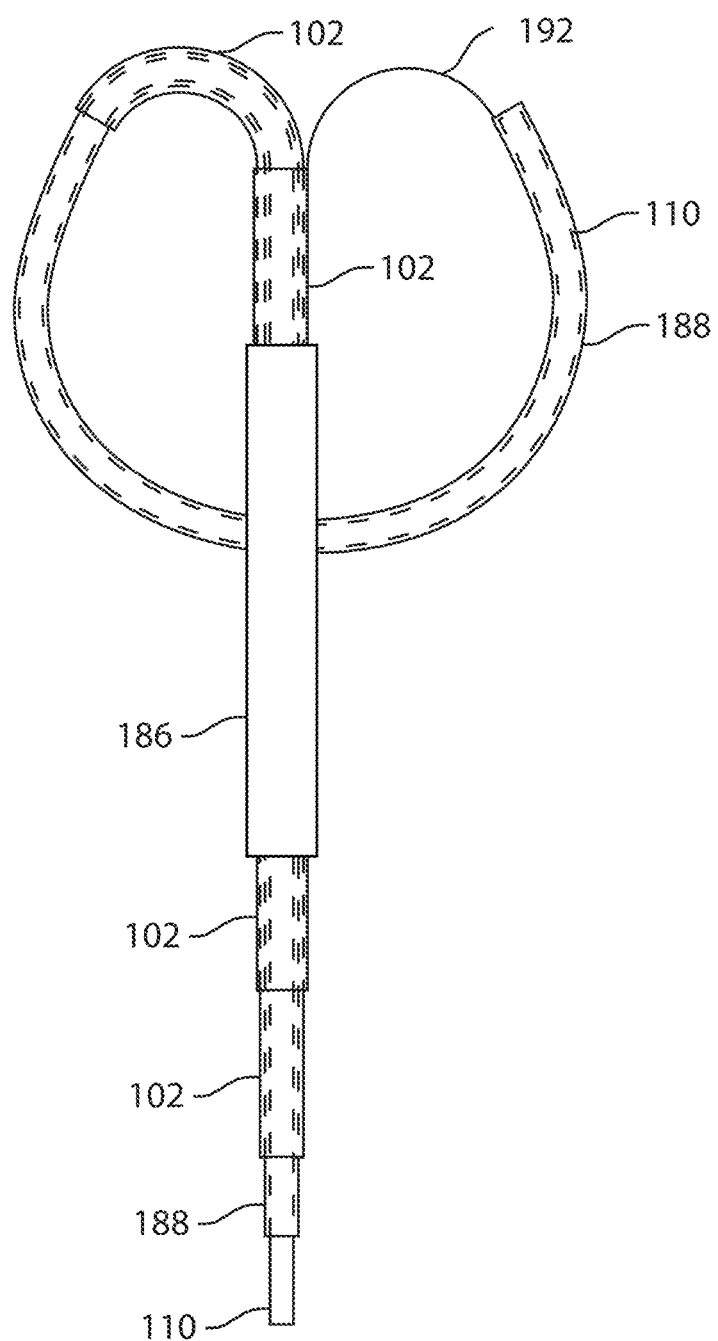

In the embodiment in FIG. 10I, one or more regions of medical component 110 may be positioned in the anatomy by one or more of: pulling and/or pushing and/or torquing or twisting medical component 110; advancing and/or retracting and/or torquing or twisting one end of functional tube 188; engaging a steering modality on first arm 102 and/or second arm 102; advancing and/or withdrawing and/or torquing or twisting first arm 102 and/or second arm 102 and advancing and/or withdrawing and/or torquing or twisting introducer sheath 186. One or more regions of medical component 110 may be repositioned as needed to access and treat one or more anatomical regions. In one embodiment shown in FIG. 10J, first arm 102 and second arm 102 are manipulated such that a portion of functional tube 188 extends in the proximal direction proximal to the distal end of introducer sheath 186. In FIG. 10J, a portion of functional tube 188 lies adjacent to or in contact with a portion of introducer sheath 186 proximal to the distal end of introducer sheath 186. FIG. 10K shows a cross sectional view through the medical system of FIG. 10I through plane 10K-10K. FIG. 10K shows introducer sheath 186 enclosing two arms 102 that in turn enclose functional tube 188 which in turn encloses medical component 110. FIG. 10L shows a cross sectional view through the medical system of FIG. 10I through plane 10L-10L. FIG. 10LA shows a cross sectional view through the medical system of FIG. 10I through plane 10LA-10LA.

Several embodiments described herein have a looped medical system 100 comprising two arms 102 and an elongate device or devices that connect the distal regions of arms 102. For example, FIG. 4A shows a looped medical system 100 comprising arms 102 and a single elongate medical component 110 that connects the distal regions of arms 102. FIG. 5A shows a looped medical system 100 comprising arms 102 and a combination of elongate medical component 110 and second medical component 122 that connects the distal regions of arms 102. In such looped medical system 100 embodiments, the looped medical system 100 may be introduced into the target anatomical site as a pre-assembled system. Such a pre-assembled medical system 100 may be collapsible and flexible for introduction through narrow lumens and cavities. In an alternate method embodiment, two arms 102 are introduced in the body. Thereafter, the distal regions of arms 102 are connected by one or more elongate devices to create a looped medical system 100 in the body.

In another method embodiment, a looped access is created between 2 openings in the body using a looped auxiliary device. Thereafter, the looped auxiliary device is used to create looped medical system 100 in the body such that arms 102 exit the body through the 2 openings. In one method embodiment of using a looped auxiliary device to create looped medical system 100 in the body, a looped access is created between 2 openings in the body using the looped auxiliary device. Thereafter, arms 102 are introduced through the 2 openings over the looped auxiliary device. Thereafter, arms 102 are navigated to the target anatomy. Thereafter, looped auxiliary device is exchanged for medical component 110 or a combination of medical component 110 and second medical component 122. To illustrate this example, consider the location of medical system 100 in medical FIG. 7A. Medical system 100 can be deployed in this position by creating a looped access between 2 openings to the femoral vein using the looped auxiliary device. Thereafter, arms 102 are introduced through the 2 femoral vein openings over the looped auxiliary device. Arms 102 are navigated through the inferior vena cava and the right atrium to the left atrium through a previously created trans-septal puncture. Thereafter, looped auxiliary device is exchanged for medical component 110 or a combination of medical component 110 and second medical component 122.

Any of the embodiments of medical system 100 described herein that comprise more than one arm 102 (e.g. medical system 100 in FIG. 4A) may be modified such that a single arm 102 is used to introduce medical component 110 and other components of medical system 100 disclosed herein. In one such embodiment, a medical component 110 is disposed within an arm 102 such that two elongate regions of medical component 110 are enclosed within arm 102 and a looped portion of medical component 110 extends beyond the distal end of arm 102. In another such embodiment, a medical component 110 is disposed within an arm 102 such that one of the elongate regions of medical component 110 is enclosed within arm 102 and the other of the elongate regions of medical component 110 is located outside arm 102. The two elongate regions of a looped medical component 110 may be present in a single lumen or in two separate lumens or compartments of arm 102. For example, the medical system 100 in FIG. 4F may be redesigned such that a single arm 102 is used to introduce entire medical component 110 including tether 114 into the anatomy. In another example, the medical system 100 of FIG. 4G may be modified such that both medical components 110 are introduced through a single arm 102. Two medical components 110 of FIG. 4G may be located within a single lumen or in two separate lumens or compartments of arm 102.

Further, any of the embodiments of medical system 100 described herein that comprise a single arm 102 (e.g. medical system 100 in FIG. 1AA) may be modified such that more than one arm 102 is used to introduce medical component 110 and other components of medical system 100 disclosed herein. In one such embodiment, an additional arm 102 mechanically cooperating with a first arm 102 is used to manipulate the position and/or the orientation of one or more regions of a medical component 110.

Embodiments of medical system 100 herein may provide many degrees of freedom to position medical component 110 and/or working element 112 in any number of positions or profiles from a linear shape to simple two dimensional curves to complex three dimensional profiles that conform to a targeted region of tissue.

Any of devices disclosed herein such as medical component 110 or arm 102 may comprise one or more of any of the steering mechanisms disclosed herein. Such steering mechanisms may be designed such that they do not interfere with the working of medical component 110. For example, in embodiments wherein medical component 110 emits microwave energy, medical component 110 may comprise one or more pull wires or other steering mechanisms made of non-metallic materials such as plastic or polymer materials.

Any of the devices (e.g. medical component 110 or an arm 102) or components (e.g. a tether 114) disclosed herein may have additional features that enable the user to obtain information about one or more of: position and/or orientation of one or more components of medical system 100, contact and/or proximity of one or more components of medical system 100 to anatomical regions, images of anatomical regions, real-time information of tissue properties (e.g. temperature, electrical activity, viability, echogenicity, etc.), a physiological parameter of the patient's body, presence of one or more devices, feedback of the success or efficacy of a procedure and risky situations arising from too much force or pressure on the anatomy. In one embodiment, a component of medical system 100 comprises a force sensor to measure forces transmitted along the shaft or the one or more components of medical system 100. This may be used to determine tissue contact by the one or more components. In another embodiment, a component of medical system 100 comprises a temperature sensing modality such as a thermocouple. In another embodiment, a component of medical system 100 comprises a pressure sensor. In another embodiment, a component of medical system 100 comprises an impedance sensor. Such an impedance sensor can be used to determine the success of efficacy of an ablation procedure. In another embodiment, a component of medical system 100 comprises an embedded intra-cardiac echography probe. In another embodiment, a component of medical system 100 comprises an embedded imaging probe capable of imaging in the non-visible electromagnetic spectrum. In an embodiment, a device or component disclosed herein comprises one or more electrodes. In one such embodiment, a device or component disclosed herein comprises multiple electrodes wherein at least two of the multiple electrodes differ in their design. In another such embodiment, a device or component disclosed herein comprises multiple electrodes wherein at least three of the multiple electrodes differ in their design.

Any of the devices or components herein may comprise a position feedback mechanism to determine the position of the device or components inside the anatomy. In one embodiment, the position feedback mechanism is a means for introducing a dye (e.g. a visually detectable dye) or a contrast agent (e.g. a radiopaque or ultrasound contrast agent) inside the anatomy. In another embodiment, the position feedback mechanism comprises one or more electrodes. In another embodiment, the position feedback mechanism comprises one or more distance markers located on an outer surface of the device or component. In one such embodiment, a medical component 110 introduceable through an arm 102 comprises one or more distance markers on the proximal region of medical component 110. In clinical use, the distance markers lie outside the body of the patient. The relative distance between the distance markers and a proximal portion of arm 102 enables the user to determine the relative distance between the distal ends of arm 102 and medical component 110. This in turn may be used to determine the degree of deployment of the distal region of medical component 110 relative to arm 102.

Any of the devices and methods disclosed herein may be used for electrophysiological isolation of the pulmonary veins (PVs) to treat atrial fibrillation. This may be done by creating one or more lesions around the pulmonary vein ostia. In one such embodiment, an anchoring mechanism is used to reversibly anchor to a region inside or around the pulmonary vein ostia. Thereafter, a medical system 100 mechanically coupled to the anchoring mechanism is used to create a series of lesions around one or more pulmonary vein ostia. The anchoring mechanism may be one or more of: anchoring balloons that may be anchored inside the pulmonary veins, guidewires that are inserted inside the pulmonary veins, magnetic devices, devices comprising a means for applying a vacuum, etc. The medical system 100 may be pivoted around such an anchoring mechanism.

Several embodiments of user interfaces may be designed to manipulate one or more regions of medical system 100 in the anatomy. In one embodiment, the user interface is a haptic system. The haptic system may have one or more of: force-feedback ability, ability to apply vibrations to the user and ability to apply one or more motions to the user. In another embodiment, the user interface comprises a joystick. The joystick may have a force feedback capability. The joystick may be configured to have one, two, three or more planes of motion. In a particular embodiment, the planes of motion of the joystick correspond to the planes of steering of one of arms 102. In one embodiment, medical system 100 comprises 2 joysticks—each joystick controlling the movement of the distal portion of an arm 102. The joystick(s) may be mounted on a console. The console may contain additional features such as displays for fluoroscopy, displays for pre-procedure imaging results, results of a real-time diagnostic modality, displays of the medical system 100 position, etc.

In one embodiment, the user interface is similar to the Sensei™ System made by Hansen Medical, Mountain View, CA In this embodiment, the user interface of medical system 100 comprises one or two robotic controllers along with several displays. The displays may display one or more of the following: fluoroscopic images, EKG data, X-ray images, intra-cardiac ultrasound images, external ultrasound images, pre-procedure electrophysiology maps, pre-procedure anatomical maps created from pre-procedure imaging, etc. Such a medical system 100 can be designed to introduce a user selected catheter into the anatomy as disclosed elsewhere in this document. The user selected catheter may be a catheter or device for accessing, diagnosing or treating the heart. Examples of such catheters include, but are not limited to ablation catheters, mapping catheters, pacing catheters, ultrasound imaging catheters (ICE catheters), guidewires, sheaths, needles, prosthetic valve delivery catheters, pacing leads and angioplasty catheters.

In another embodiment, the user interface is similar to the da Vinci® Surgical System made by Intuitive Surgical, Sunnyvale, CA In this embodiment, the user interface of medical system 100 comprises one, two or more robotic controllers along with several displays. The displays may display one or more of the following: endoscopic images, fluoroscopic images, EKG data, X-ray images, intra-cardiac ultrasound images, external ultrasound images, pre-procedure electrophysiology maps, pre-procedure anatomical maps created from pre-procedure imaging, etc. Such a medical system 100 comprising a robotic user interface can be used to treat a variety of internal organs including, but not limited to stomach, gall bladder, colon, rectum, urinary bladder, uterus and other regions of the female reproductive tract, regions of the male reproductive tract, esophagus, heart, lungs, liver, spleen, small intestine, and other pleural, visceral or peritoneal organs. The procedures may be performed on the surface of such organs, inside lumens or cavities of such organs or within an interior portion of such organs.

Any of the intra-cardiac procedures disclosed herein may be performed in conjunction with an accessory device placed inside the esophagus or on the external surface of the heart or the pericardium. Such accessory devices may be selected from the group including, but not limited to: imaging devices such as Intracardiac Echocardiography (ICE) probes, temperature sensing devices, shields for shielding microwave energy and components of a surgical navigation system.

MRI imaging may be used along with any of the devices disclosed herein to visualize one or both of: portions of the devices disclosed herein and portions of the anatomy. One of more components of the devices disclosed herein may be made of non-ferrous or non-ferromagnetic materials.

It is important to note that the embodiments shown herein may be designed to be used in the left atrium of the heart to perform one or more diagnostic procedures (e.g. electrophysiology mapping procedures), one or more treatment procedures (e.g. ablation procedures) and combinations thereof. In such designs, one of arms 102 may be translated relative to the other of arms 102. This allows the user to change the relative positions of regions of arms 102. Also, in such designs, one or more arms 102 may have multiplanar steering ability. The multiplanar steering may be used to deflect or steer the distal region of arms 102 in multiple planes without torquing arms 102. Arms 102 may be introduced in the heart using an auxiliary device loop such that each arm 102 is introduced through a single femoral puncture. Thereafter, auxiliary device loop may be exchanged for medical component 110 to create the looped medical system 100 inside the body. Embodiments of medical system 100 comprising arms 102 and medical component 110 may be sufficiently flexible and have a sufficiently low profile to enable a user to introduce the medical system 100 through the vasculature. For example, medical system 100 may be introduced through the femoral vein into the right atrium and thereafter through a trans-septal puncture into the left atrium. Medical system 100 can be used to treat various tissue regions of the heart including, but not limited to right atrium, left atrium, right ventricles, left ventricles, ostia of pulmonary veins and other vasculature connected to the heart and valves. In embodiments where medical component 110 is the only device between two arms 102 in the heart, medical component 110 may comprise an electrical working element. Examples of such electrical working elements include, but are not limited to linear or non-linear ablation electrode(s) or antenna(s), linear or non-linear mapping electrode(s) or antenna(s), linear or non-linear pacing electrode(s) or antenna(s) and linear or non-linear electrosurgical cutting elements. In embodiments where medical component 110 is used to introduce second medical component 110 between two arms 102 in the heart, second medical component may comprise an electrical working element. Examples of such electrical working elements include, but are not limited to linear or non-linear ablation electrode(s) or antenna(s), linear or non-linear mapping electrode(s) or antenna(s), linear or non-linear pacing electrode(s) or antenna(s) and linear or non-linear electrosurgical cutting elements. In the embodiments where electrical working elements are used for ablation, mapping or pacing, physical motion of a component of medical system 100 may not be necessary for the medical action. For example, medical system 100 may be used to position an ablation antenna of medical component 110 adjacent to a target tissue in the heart and thereafter ablate the target tissue without moving any of arms 102 and medical component 110.

The region of medical system 100 extending between the distal regions of arms 102 may or may not have a uniform cross sectional profile throughout the region of medical system 100 extending between the distal regions of arms 102. For example, FIG. 4A shows a medical system 100 comprising a medical component 110 extending between the distal regions of arms 102 such that the region of medical component 110 extending between the distal regions of arms 102 has a substantially uniform cross sectional profile. FIG. 6K shows a medical system 100 comprising a medical component 110 extending between the distal regions of arms 102 such that the region of medical component 110 extending between the distal regions of arms 102 has a non-uniform cross sectional profile. As shown in FIG. 6K, the cross section of the region of medical component 110 adjacent to the distal region of one of arms 102 is larger than the cross section of the region of medical component 110 adjacent to the distal region of the other of arms 102.

In one embodiment, medical component 110 or one or more devices introduced by medical component 110 are magnetically enabled devices capable of being magnetically navigated in the anatomy. Such magnetic navigation may be used to further aid the precise positioning and orientation of medical component 110 or one or more devices introduced by medical component 110. In one embodiment, the distal region of medical component 110 such as an arm 102 or one or more devices introduced by medical component 110 are capable of being magnetically navigated by a magnetic navigation system such as the Stereotaxis Magnetic Navigation System made by Stereotaxis Inc., St. Louis, MO One or more movements of such devices can be computer controlled.

One or more arms 102 disclosed herein may be controlled robotically by a user. For example, one or more arms 102 may be Artisan™ Control Catheters controlled by the Sensei™ Robotic Catheter System made by Hansen Medical, Mountain View, CA.

Any of the steering mechanisms disclosed herein may be designed such that a distal end of the steered device replicates a user motion applied to the proximal region of the device. In another embodiment, any of the steering mechanisms herein may be designed such that a distal end of the steered device replicates the mirror image of a user motion applied to the proximal region of the device.

Several examples or embodiments of the invention have been discussed herein, but various modifications, additions and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. If the various steps of a method are disclosed in a particular order, the various steps may be carried out in any other order unless doing so would render the method embodiment unsuitable for its intended use. Various reasonable modifications, additions and deletions of the described examples or embodiments are to be considered equivalents of the described examples or embodiments.

We claim:

1. A microwave emitting device coupleable to a microwave energy source for delivering energy from the energy source, the microwave emitting device comprising:
a transmission line having an outer conductor;
an antenna configured to be coupled to the energy source, the antenna having a proximal end, a distal end and an antenna axis, wherein the antenna generates a microwave field upon application of energy from the energy source, where the antenna comprises an inner conductor, a radiating element coupled to the inner conductor, and a shaping element coupled to the outer conductor;

at least one electrode positioned along the antenna, wherein the at least one electrode is exposed to the microwave field and is electrically isolated from the antenna; and a conductive wire electrically coupled to the at least one electrode, wherein the conductive wire is electrically isolated from the antenna, wherein a first portion of the conductive wire exposed to the microwave field emitted by the antenna is helically disposed about the antenna axis.

2. The microwave emitting device of claim 1, wherein the shaping element is configured to shape the microwave field emitted by radiating element.

3. The microwave emitting device of claim 1, wherein the at least one electrode is spaced entirely between the proximal end and the distal end of the antenna.

4. The microwave emitting device of claim 1, wherein the at least one electrode is coupleable to a second power supply.

5. The microwave emitting device of claim 1, wherein every section of the first portion of the wire is non-parallel to the axis of the antenna.

6. The microwave emitting device of claim 1, wherein the at least one electrode is located externally over the antenna.

7. The microwave emitting device of claim 1, wherein the first portion of the conductive wire is shaped in a helix having an axis and is disposed such that the axis is parallel to the antenna axis.

8. The microwave emitting device of claim 1, wherein the first portion of the conductive wire covers at least one turn around the antenna.

9. The microwave emitting device of claim 1, wherein the first portion of the conductive wire is symmetrically disposed around the antenna.

10. The microwave emitting device of claim 1, wherein the antenna generates a radially symmetric microwave field.

11. The microwave emitting device of claim 1, wherein an arrangement of the conductive wire relative to the antenna and the at least one electrode produces a symmetrical microwave field.

12. The microwave emitting device of claim 1, wherein a majority of the microwave field is located distal to a distal end of the transmission line.

13. The microwave emitting device of claim 1, wherein a second portion of the conductive wire is located distal to the distal end of the antenna.

14. The microwave emitting device of claim 1, wherein a second portion of the conductive wire is located proximal to the proximal end of the antenna.

15. The microwave emitting device of claim 1, wherein the at least one electrode and the conductive wire are fixed relative to the antenna.

16. The microwave emitting device of claim 1, wherein the antenna comprises an antenna dielectric, wherein at least one portion of the conductive wire is located inside the antenna dielectric.

17. The microwave emitting device of claim 1, wherein the at least one electrode comprises a plurality of electrodes located along the antenna.

18. The microwave emitting device of claim 17, wherein the plurality of electrodes are spaced apart from each other along the antenna axis.

19. The microwave emitting device of claim 1, wherein the electrode and the conductive wire are located on a device having a lumen and the antenna is slidably located in the lumen.

* * * * *